US012636048B2

(12) United States Patent
Dorman

(10) Patent No.: US 12,636,048 B2
(45) Date of Patent: May 26, 2026

(54) ATTACHMENT APPARATUS TO SECURE A MEDICAL ALIGNMENT DEVICE TO ALIGN A TOOL

(71) Applicant: Circinus Medical Technology LLC, Concord, MA (US)

(72) Inventor: John Kyle Dorman, Midland, TX (US)

(73) Assignee: Circinus Medical Technology LLC, Concord, MA (US)

( * ) Notice: Subject to any disclaimer, the term of this patent is extended or adjusted under 35 U.S.C. 154(b) by 657 days.

(21) Appl. No.: 17/970,378

(22) Filed: Oct. 20, 2022

(65) Prior Publication Data

US 2023/0131831 A1     Apr. 27, 2023

Related U.S. Application Data

(60) Provisional application No. 63/271,080, filed on Oct. 22, 2021.

(51) Int. Cl.
   *A61B 17/70*        (2006.01)
   *A45C 11/00*        (2006.01)
   (Continued)

(52) U.S. Cl.
   CPC .......... *A61B 17/7092* (2013.01); *A61B 34/10* (2016.02); *A45C 11/003* (2025.01);
   (Continued)

(58) Field of Classification Search
   CPC ......... A61B 34/20; A61B 34/25; A61B 34/10; A61B 34/30; A61B 2034/107;
   (Continued)

(56) References Cited

U.S. PATENT DOCUMENTS

| | | |
|---|---|---|
| D323,504 S | 1/1992 | Langton |
| 5,143,076 A | 9/1992 | Hardy et al. |

(Continued)

FOREIGN PATENT DOCUMENTS

| | | |
|---|---|---|
| CN | 101198958 A | 6/2008 |
| CN | 101528122 A | 9/2009 |

(Continued)

OTHER PUBLICATIONS

International Search Report and Written Opinion in PCT/US2024/041823 dated Jan. 13, 2025.

(Continued)

*Primary Examiner* — Marcela I. Shirsat
(74) *Attorney, Agent, or Firm* — Foley & Lardner LLP

(57)     ABSTRACT

An apparatus is disclosed for use with an electronic device for alignment of a medical tool for positioning a surgical hardware device. The apparatus includes a case to secure the electronic device such that the electronic device is secured to the case and does not move relative to the case. The case includes an opening to couple with at least a portion of the medical tool. The electronic device is secured relative to the medical tool through the coupling of the case to the at least the portion of the medical tool. The electronic device simulates a three-dimensional position of the surgical hardware device in a body using a diagnostic representation of at least a portion of the body, and the electronic device is secured in the case and coupled to the medical tool assists with the alignment of the medical.

10 Claims, 36 Drawing Sheets

(51) Int. Cl.

| | |
|---|---|
| *A61B 17/00* | (2006.01) |
| *A61B 17/17* | (2006.01) |
| *A61B 34/00* | (2016.01) |
| *A61B 34/10* | (2016.01) |
| *A61B 34/20* | (2016.01) |
| *A61B 90/00* | (2016.01) |

(52) U.S. Cl.
CPC . *A61B 2017/00477* (2013.01); *A61B 17/1757* (2013.01); *A61B 2034/104* (2016.02); *A61B 2034/105* (2016.02); *A61B 2034/107* (2016.02); *A61B 34/20* (2016.02); *A61B 2034/2048* (2016.02); *A61B 34/25* (2016.02); *A61B 2090/372* (2016.02)

(58) Field of Classification Search
CPC ........ A61B 2034/104; A61B 2034/105; A61B 2034/2048; A61B 90/00; A61B 2090/365; A61B 2090/372; A61B 17/1757; A61B 17/7092; A61B 2017/00477; G06T 19/20; A45C 11/002; A45C 11/00; A45C 11/001; A45C 11/003; A45C 15/00; A45C 2200/00; A45C 2200/15; A45C 2013/025; A45C 13/02; H04M 1/0283; H04M 1/0279; H04M 1/0281; H04M 1/724092; H04M 1/04; H04M 1/72412; H04M 1/0203; G06F 1/16; G06F 1/1613; G06F 1/1629; G06F 1/163; G06F 1/1633; G06F 1/1637; G06F 1/1656; G06F 1/1628; G06F 1/1632; G06F 2200/1633; H04B 1/3883; H04B 1/3888
USPC .......................... 600/424, 427; 606/130, 104
See application file for complete search history.

(56) References Cited

U.S. PATENT DOCUMENTS

| | | | |
|---|---|---|---|
| 5,603,318 | A | 2/1997 | Heilbrun et al. |
| 5,824,085 | A | 10/1998 | Sahay et al. |
| 5,880,976 | A | 3/1999 | DiGioia III et al. |
| 6,129,670 | A | 10/2000 | Burdette et al. |
| 6,139,544 | A | 10/2000 | Mikus et al. |
| 6,246,474 | B1 | 6/2001 | Cerni et al. |
| 6,511,236 | B1 | 1/2003 | Webjorn et al. |
| 6,638,281 | B2 | 10/2003 | Gorek |
| 7,158,376 | B2 * | 1/2007 | Richardson ........... G06F 1/1626 |
| | | | 361/679.56 |
| RE40,176 | E | 3/2008 | Peshkin et al. |
| 7,611,522 | B2 | 11/2009 | Gorek |
| 8,086,077 | B2 | 12/2011 | Eichhorn |
| 8,442,621 | B2 | 5/2013 | Gorek et al. |
| 9,038,971 | B1 | 5/2015 | Guthrie |
| 9,119,572 | B2 | 9/2015 | Gorek et al. |
| 9,216,048 | B2 | 12/2015 | Markey et al. |
| D772,859 | S | 11/2016 | Alesi et al. |
| 9,585,700 | B2 | 3/2017 | Wehrle et al. |
| 9,687,306 | B2 | 6/2017 | Markey et al. |
| 9,975,497 | B2 | 5/2018 | Kim |
| 10,064,687 | B2 | 9/2018 | Haimerl et al. |
| 10,123,840 | B2 | 11/2018 | Dorman |
| 10,335,237 | B2 | 7/2019 | Christian et al. |
| 10,342,619 | B2 | 7/2019 | Bracke et al. |
| 10,561,466 | B2 | 2/2020 | Hedblom et al. |
| 10,602,114 | B2 | 3/2020 | Casas |
| 10,603,116 | B2 | 3/2020 | Markey et al. |
| 10,650,594 | B2 | 5/2020 | Jones et al. |
| 10,864,023 | B2 | 12/2020 | Pak et al. |
| 10,908,771 | B2 | 2/2021 | Berquam et al. |
| 10,952,775 | B1 | 3/2021 | Drain |
| 11,000,335 | B2 | 5/2021 | Dorman |
| 11,020,016 | B2 | 6/2021 | Wallace et al. |
| 11,191,592 | B2 | 12/2021 | Gorek et al. |
| 11,484,381 | B2 | 11/2022 | Pak et al. |
| 11,737,828 | B2 | 8/2023 | Dorman |
| 11,826,111 | B2 | 11/2023 | Mahfouz |
| 11,832,886 | B2 | 12/2023 | Dorman |
| 12,063,433 | B2 | 8/2024 | Dorman |
| 12,064,186 | B2 | 8/2024 | Dorman |
| 12,096,993 | B2 | 9/2024 | Toporek et al. |
| 12,213,740 | B2 | 2/2025 | Dorman |
| 12,400,355 | B2 | 8/2025 | Dorman |
| 12,433,690 | B2 | 10/2025 | Dorman |
| 12,440,279 | B2 | 10/2025 | Dorman |
| 2002/0035323 | A1 | 3/2002 | Saha et al. |
| 2002/0077540 | A1 | 6/2002 | Kienzle, III |
| 2002/0120252 | A1 | 8/2002 | Brock et al. |
| 2002/0140694 | A1 | 10/2002 | Sauer et al. |
| 2003/0181919 | A1 | 9/2003 | Gorek |
| 2003/0199882 | A1 | 10/2003 | Gorek |
| 2003/0236548 | A1 | 12/2003 | Hovanes et al. |
| 2004/0068187 | A1 | 4/2004 | Krause et al. |
| 2005/0113846 | A1 | 5/2005 | Carson |
| 2005/0192575 | A1 | 9/2005 | Pacheco |
| 2005/0236545 | A1 | 10/2005 | Seil et al. |
| 2006/0004322 | A1 | 1/2006 | Uesugi et al. |
| 2007/0262223 | A1 | 11/2007 | Wang et al. |
| 2007/0276397 | A1 | 11/2007 | Tacheco |
| 2008/0057889 | A1 | 3/2008 | Jan |
| 2008/0086160 | A1 | 4/2008 | Mastri et al. |
| 2008/0200927 | A1 | 8/2008 | Hartmann et al. |
| 2009/0090757 | A1 | 4/2009 | Kim et al. |
| 2009/0157083 | A1 | 6/2009 | Park et al. |
| 2009/0163901 | A1 | 6/2009 | Fisher et al. |
| 2009/0270868 | A1 | 10/2009 | Park et al. |
| 2009/0292201 | A1 | 11/2009 | Kruecker |
| 2009/0292279 | A1 | 11/2009 | Bliweis et al. |
| 2009/0311655 | A1 | 12/2009 | Karkanias et al. |
| 2010/0100081 | A1 | 4/2010 | Tuma et al. |
| 2010/0153081 | A1 | 6/2010 | Bellettre et al. |
| 2010/0198402 | A1 | 8/2010 | Greer et al. |
| 2010/0210939 | A1 | 8/2010 | Hartmann et al. |
| 2010/0274256 | A1 | 10/2010 | Ritchey et al. |
| 2011/0098721 | A1 | 4/2011 | Tran et al. |
| 2011/0214279 | A1 | 9/2011 | Park et al. |
| 2011/0268248 | A1 | 11/2011 | Simon et al. |
| 2012/0116203 | A1 | 5/2012 | Vancraen et al. |
| 2012/0150243 | A9 | 6/2012 | Crawford et al. |
| 2012/0232834 | A1 | 9/2012 | Roche et al. |
| 2012/0319859 | A1 | 12/2012 | Taub et al. |
| 2013/0060146 | A1 | 3/2013 | Yang et al. |
| 2013/0085344 | A1 | 4/2013 | Merkl et al. |
| 2013/0095855 | A1 | 4/2013 | Bort |
| 2013/0114866 | A1 | 5/2013 | Kasodekar et al. |
| 2013/0245461 | A1 | 9/2013 | Maier-Hein et al. |
| 2013/0253599 | A1 | 9/2013 | Gorek et al. |
| 2014/0148808 | A1 | 5/2014 | Inkpen et al. |
| 2014/0257319 | A1 | 9/2014 | Polster |
| 2015/0010220 | A1 | 1/2015 | Teichman et al. |
| 2016/0022374 | A1 * | 1/2016 | Haider ................. A61B 17/142 |
| | | | 606/96 |
| 2016/0106202 | A1 | 4/2016 | Ford |
| 2016/0235481 | A1 | 8/2016 | Dorman |
| 2016/0250040 | A1 | 9/2016 | Hermle et al. |
| 2016/0324580 | A1 | 11/2016 | Esterberg |
| 2016/0373647 | A1 | 12/2016 | Morate et al. |
| 2017/0007328 | A1 | 1/2017 | Cattin et al. |
| 2017/0027651 | A1 | 2/2017 | Esterberg |
| 2017/0035517 | A1 | 2/2017 | Geri et al. |
| 2017/0071673 | A1 | 3/2017 | Ferro et al. |
| 2017/0135706 | A1 | 5/2017 | Frey et al. |
| 2017/0172696 | A1 | 6/2017 | Saget et al. |
| 2017/0202633 | A1 | 7/2017 | Liu |
| 2017/0221244 | A1 | 8/2017 | Hiraga et al. |
| 2017/0245947 | A1 | 8/2017 | Bozung et al. |
| 2017/0304011 | A1 | 10/2017 | Markey et al. |
| 2017/0333134 | A1 | 11/2017 | Wollowick et al. |
| 2017/0367771 | A1 | 12/2017 | Tako et al. |
| 2018/0000380 | A1 | 1/2018 | Stein et al. |
| 2018/0008358 | A1 | 1/2018 | Kostrzewski et al. |
| 2018/0092699 | A1 | 4/2018 | Finley et al. |
| 2018/0140362 | A1 | 5/2018 | Cal et al. |

(56) References Cited

U.S. PATENT DOCUMENTS

| | | | |
|---|---|---|---|
| 2018/0303559 A1 | 10/2018 | Shepherd et al. | |
| 2018/0310956 A1 | 11/2018 | Polster | |
| 2018/0325618 A1 | 11/2018 | Justin et al. | |
| 2019/0029757 A1 | 1/2019 | Roh et al. | |
| 2019/0046278 A1 | 2/2019 | Steinle et al. | |
| 2019/0060000 A1 | 2/2019 | Dorman | |
| 2019/0090959 A1 | 3/2019 | Haider et al. | |
| 2019/0223962 A1 | 7/2019 | Roldan et al. | |
| 2019/0231432 A1 | 8/2019 | Amanatullah | |
| 2019/0254754 A1 | 8/2019 | Johnson et al. | |
| 2019/0321109 A1 | 10/2019 | Frasier et al. | |
| 2019/0336179 A1 | 11/2019 | Pak et al. | |
| 2019/0357809 A1 | 11/2019 | Borja | |
| 2019/0388173 A1 | 12/2019 | Pak et al. | |
| 2020/0051274 A1 | 2/2020 | Siemionow et al. | |
| 2020/0111213 A1 | 4/2020 | Chacon et al. | |
| 2020/0197191 A1 | 6/2020 | Akhlaghpour et al. | |
| 2020/0229869 A1 | 7/2020 | Dorman | |
| 2020/0236799 A1* | 7/2020 | Roth | F16B 2/12 |
| 2020/0237255 A1 | 7/2020 | Silverstein et al. | |
| 2020/0237446 A1 | 7/2020 | Drain | |
| 2020/0305980 A1 | 10/2020 | Lang | |
| 2020/0305985 A1 | 10/2020 | Tolkowsky | |
| 2021/0038340 A1 | 2/2021 | Itkowitz et al. | |
| 2021/0100536 A1 | 4/2021 | Spindle | |
| 2021/0186617 A1 | 6/2021 | Gorek et al. | |
| 2021/0228279 A1 | 7/2021 | Dorman | |
| 2022/0192756 A1 | 6/2022 | Dorman | |
| 2022/0201199 A1 | 6/2022 | Dorman | |
| 2022/0237817 A1 | 7/2022 | Dorman | |
| 2022/0241018 A1 | 8/2022 | Dorman | |
| 2022/0351410 A1 | 11/2022 | Siemionow et al. | |
| 2023/0036038 A1 | 2/2023 | Finley et al. | |
| 2023/0054394 A1 | 2/2023 | Luo et al. | |
| 2023/0172631 A1 | 6/2023 | Richter et al. | |
| 2023/0346481 A1 | 11/2023 | Dorman | |
| 2024/0090950 A1 | 3/2024 | Dorman | |
| 2024/0197411 A1 | 6/2024 | Dorman | |
| 2024/0406547 A1 | 12/2024 | Dorman | |
| 2024/0407847 A1 | 12/2024 | Dorman | |
| 2025/0049514 A1 | 2/2025 | Dorman | |
| 2025/0160959 A1 | 5/2025 | Dorman | |

FOREIGN PATENT DOCUMENTS

| | | | |
|---|---|---|---|
| CN | 101721231 A | 6/2010 | |
| CN | 101984931 A | 3/2011 | |
| CN | 103519895 A | 1/2014 | |
| EP | 2 901 957 A1 | 8/2015 | |
| KR | 101478522 B1 | 1/2015 | |
| KR | 101901521 B1 | 9/2018 | |
| WO | WO-2013/020026 | 2/2013 | |
| WO | WO-2014/025305 A1 | 2/2014 | |
| WO | WO-2014/063181 A1 | 5/2014 | |
| WO | WO-2015/168781 | 11/2015 | |
| WO | WO-2016/007936 | 1/2016 | |
| WO | WO-2016/131016 A2 | 8/2016 | |
| WO | WO-2017/167799 A1 | 10/2017 | |
| WO | WO-2018/200767 A1 | 11/2018 | |
| WO | WO-2019/036524 A1 | 2/2019 | |
| WO | WO-2020/105049 A1 | 5/2020 | |
| WO | WO-2020/214645 A1 | 10/2020 | |
| WO | WO-2020/214744 A1 | 10/2020 | |
| WO | WO-2020/216934 A1 | 10/2020 | |
| WO | WO-2022/109185 A1 | 5/2022 | |

OTHER PUBLICATIONS

U.S. Appl. No. 16/639,107, filed Feb. 13, 2020, System and Method Using Augmented Reality With Shape Alignment for Medical Device Placement in Bone.
U.S. Appl. No. 17/233,301, filed Apr. 16, 2021, System and Method for Medical Device Placement in Bone.
U.S. Appl. No. 17/604,359, filed Oct. 15, 2021, Attachment Apparatus to Secure a Medical Alignnient Device to Align a Tool.
U.S. Appl. No. 17/604,362, filed Oct. 15, 2021, Orientation Calibration System for Image Capture.
U.S. Appl. No. 17/530,311, filed Nov. 18, 2021, Systems and Methods for Artificial Intelligence Based Image Analysis for Placement of Surgical Appliance.
U.S. Appl. No. 17/591,478, filed Feb. 2, 2022, Systems and Methods for Simulating Three-Dimensional Orientations of Surgical Hardware Devices About an Insertion Point of an Anatomy.
U.S. Appl. No. 18/513,155, filed Nov. 17, 2023, CIRCINUS MEDICAL TECHNOLOGY LLC.
U.S. Appl. No. 18/553,025, filed Sep. 28, 2023, CIRCINUS MEDICAL TECHNOLOGY LLC.
U.S. Appl. No. 18/554,969, filed Oct. 11, 2023, CIRCINUS MEDICAL TECHNOLOGY LLC.
Crescendo CR-30 phone holder. Amazon datasheet [online]. Crescendo, first available on Nov. 18, 2017. [Retrieved on Jun. 13, 2024]; Retrieved from the Internet. <URL: https://a.co/d/fyEOcbM>.
U.S. Appl. No. 16/639,107, filed Feb. 13, 2020, System and Method Using Augmented Reality With Shape Alignment for Medical Device Placement.
U.S. Appl. No. 17/604,359, filed Oct. 15, 2021, Attachment Apparatus to Secure a Medical Alignment Device to Align a Tool.
U.S. Appl. No. 18/553,025, filed Sep. 28, 2023, System and Method for Simulating an Orientation of a Medical Device at an Insertion Point.
U.S. Appl. No. 18/350,672, filed Jul. 11, 2023, System and Method for Medical Device Placement.
U.S. Appl. No. 18/554,969, filed Oct. 11, 2023, System and Method for LIDAR-Based Anatomical Mapping.
A. Elmi-Terander et al., "Surgical Navigation Technology Based on Augmented Reality and Integrated 3D Intraoperative Imaging: A Spine Cadaveric Feasibility and Accuracy Study", Spine 41.21 (2016): E1303-E1311.
M. Herold, "Using Deep Convolutional Networks to Regress a C-arm's Position from a single X-ray Image", Diss. 2020.
G. Wells et al., "Vision-based robot positioning using neural networks", Image and Vision Computing, 14 (1996) 715-732.
Julian Horsey, "Ozaki iCoat Finger Case Makes Draw Something Even More Fun", Apr. 20, 2012, pp. 1-11, XP093028330, Retrieved from the Internet: URL:https://www.geeky-gadgets.com/ozaki-icoat-finger-case-makes-draw-someting-even-more-fun-20-04-2012/ [retrieved on Mar. 2, 2023].
International Pat. Appl. No. PCT PCT/US2021/059965, International Search Report and Written Opinion dated Feb. 3, 2022, 7 pgs.
International Pat. Appl. No. PCT/US2020/028220, International Search Report and Written Opinion, dated Aug. 14, 2020, 22 pgs.
International Pat. Appl. No. PCT/US2020/028375, International Search Report and Written Opinion dated Jul. 21, 2020, 10 pgs.
International Patent Appl. No. PCT/US2022/022204, International Search Report and Written Opinion dated Jun. 10, 2022, 18 pgs.
International Preliminary Report on Patentability for PCT Application No. PCT/US16/17897 dated Aug. 15, 2017, 9 pages.
International Preliminary Report on Patentability, International Patent Appl. No. PCT/US2018/046786, dated Feb. 27, 2020, 7 pages.
International Search Report and Written Opinion in corresponding international application No. PCT/US2016/017897, mailed Aug. 24, 2016, 13 pages.
International Search Report and Written Opinion in PCT/US18/46786, dated Dec. 13, 2018, 10 pgs.
International Search Report and Written Opinion issued in PCT/US2022/014988 Dtd Apr. 6, 2022, 17 pages.
Merloz et al., "Pedicle Screw Placement Using Image Guided Techniques." Clinical Orthopaedics and Related Research, No. 354, pp. 39-48, 1998, entire document [online] URL=<https://journals.lww.com/clinorthop/Fulltext/1998/09000/Pedicle_Screw_Placement_Using_Image_Guided.6.aspx>.
U.S. Appl. No. 17/604,359, filed Oct. 15, 2021, Attachnient Apparatus to Secure a Medical Alignment Device to Align a Tool.
International Search Report and Written Opinion for International Patent Application PCT/US2022/024683 dated Jun. 21, 2022.

(56) References Cited

OTHER PUBLICATIONS

International Search Report and Written Opinion on PCT/US2022/047306 Dated Mar. 28, 2023.

Extended European Search Report on EP 22788881.5 dtd Jan. 21, 2025 (12 pgs.).

U.S. Appl. No. 17/233,301, filed Apr. 16, 2021, System and Method for Medical Device Placement.

Harrison, Peter, Simpler Line Follower Sensors, Micromouse Online, Apr. 15, 2011, https://web.archive.org/web/20120422001123 /https://micromouseonline.com/2011/04/15/simpler-line-follower-sensors/. (Year: 2011), 3 pgs.

NumPy—Data Types, tutorialspoint, https://web.archive.org/web/20181126133733/https://www.tutorialspoint.com/numpy/numpy_data_type.htm. 2018 (Year: 2018), 8 pgs.

Anonymous "Dash Smart Instrument Technologies" Dec. 31, 2014, 243 pages, XP093247752, manualslib.de [retrieved on Feb. 7, 2025] URL: https://www.manualslib.de/download/708399/Brainlab-Dash-Smart-Instrument.html.

Partial Supplementary European Search Report on EP 22884487.4 dated Sep. 25, 2025.

* cited by examiner

Lateral view
250

Posterior View
270

332 - Gyroscope

334 - IMU

336 - Accelerometer

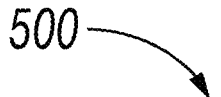
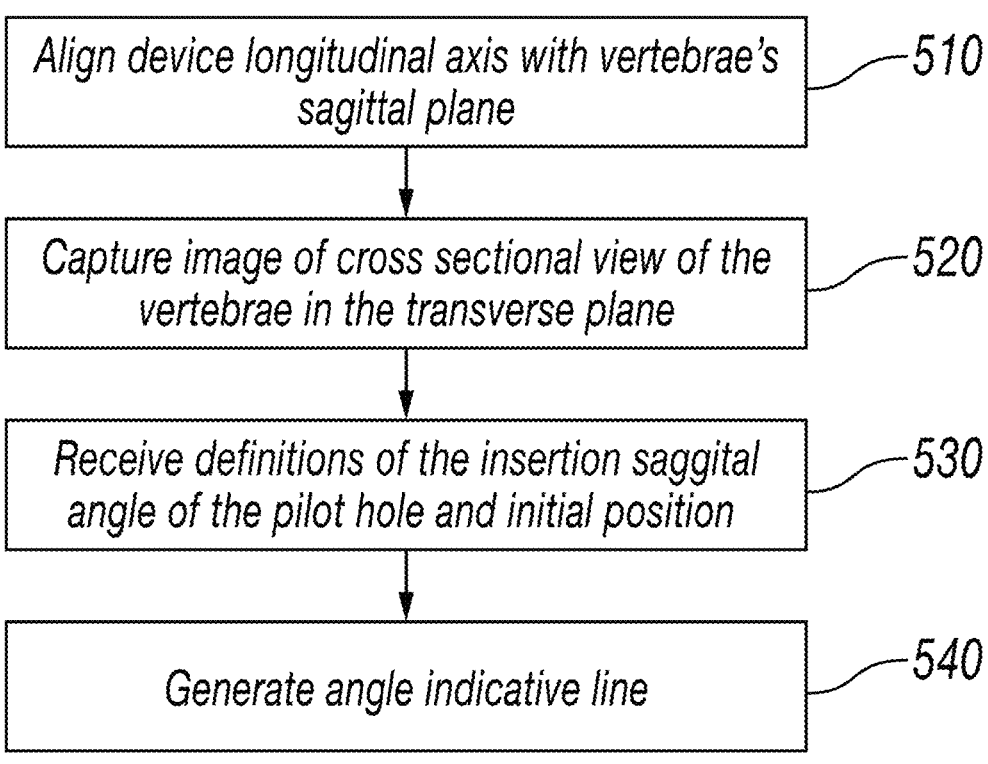
Align device longitudinal axis with vertebrae's sagittal plane —510
Capture image of cross sectional view of the vertebrae in the transverse plane —520
Receive definitions of the insertion saggital angle of the pilot hole and initial position —530
Generate angle indicative line —540
*FIG. 5B*

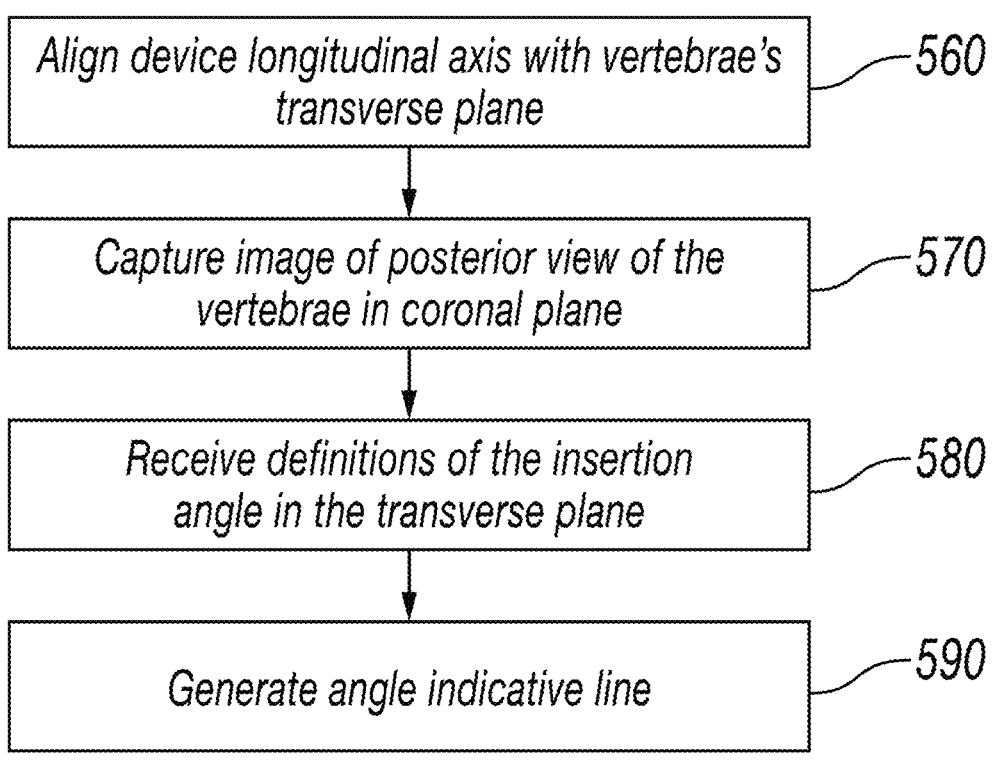
*FIG. 5C*

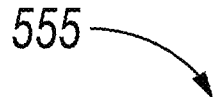
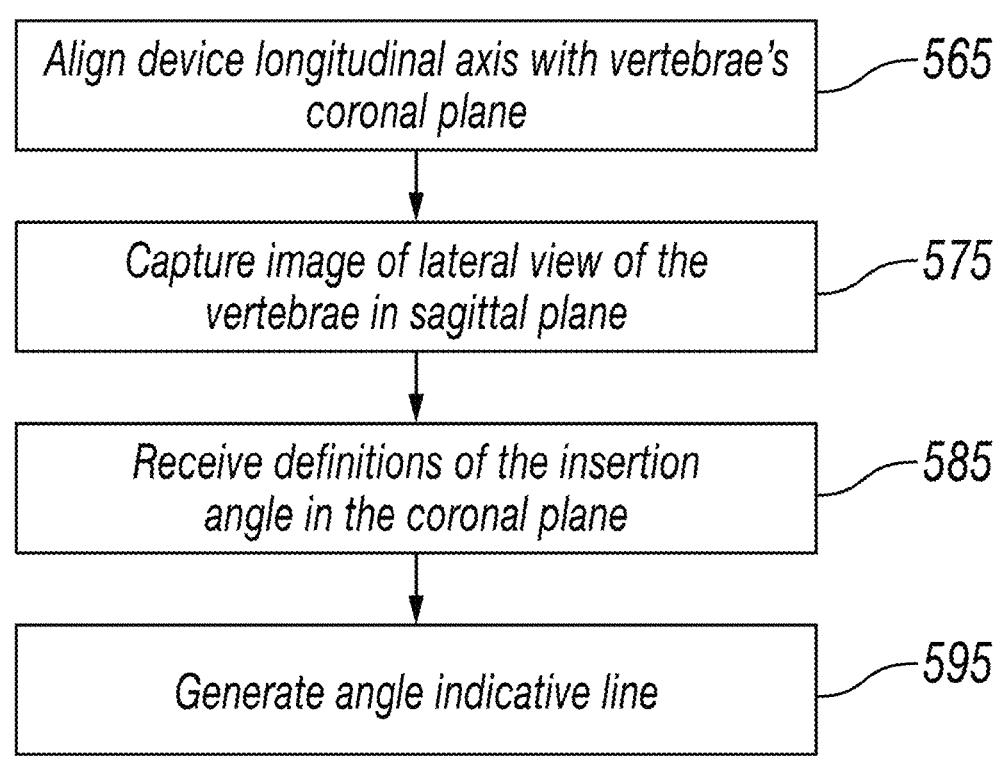
*FIG. 5D*

633

635

632

634

642

644

Entry Point          Trajectory

Back     Draw     Nav     R L / L R 700
704
701

701
799

789

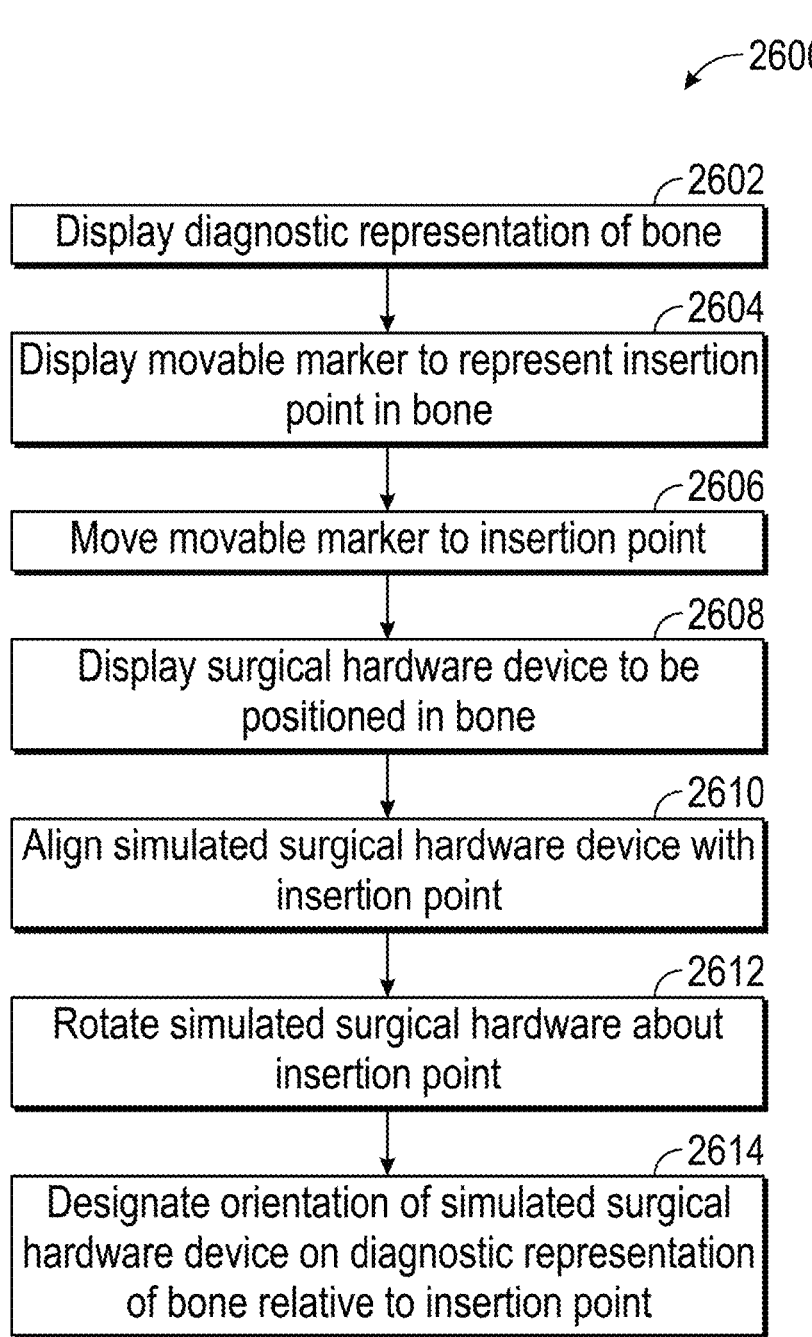

2600

2602
Display diagnostic representation of bone

2604
Display movable marker to represent insertion point in bone

2606
Move movable marker to insertion point

2608
Display surgical hardware device to be positioned in bone

2610
Align simulated surgical hardware device with insertion point

2612
Rotate simulated surgical hardware about insertion point

2614
Designate orientation of simulated surgical hardware device on diagnostic representation of bone relative to insertion point

ATTACHMENT APPARATUS TO SECURE A MEDICAL ALIGNMENT DEVICE TO ALIGN A TOOL

CROSS-REFERENCE TO RELATED APPLICATION AND CLAIM OF PRIORITY

This application claims priority to and the benefit from U.S. Provisional Patent Application No. 63/271,080, titled "Attachment Apparatus To Secure A Medical Alignment Device To Align A Tool," filed Oct. 22, 2021, the entire disclosure of which is hereby incorporated herein by reference for any and all purposes.

TECHNICAL FIELD

This disclosure generally relates to medical devices and systems. For example, this disclosure generally relates to an attachment apparatus for an electronic alignment device that facilitates the aligning and orientation of tools, devices, apparatus, such as, for example, surgical equipment and surgical tools. In one example, the surgical tools to be aligned may include tools used in connection with installing or inserting a medical device or apparatus in a body. In one implementation, the surgical tools or equipment is used to create a pilot hole in a vertebra for receiving a pedicle screw at a precise orientation, such as a transverse angle, sagittal angle, or any other angle, including a three-dimensional alignment angle or insertion angle.

BACKGROUND

Patients who undergo certain procedures, such as a spinal fusion, may have pedicle screws placed into their vertebrae. The pedicle screws are typically implanted into the vertebrae through the pedicles of the vertebrae. Once a pilot hole is created through the cortex of the bone, a probe is used to create the path through which the pedicle screw will be placed into the vertebrae. Placing the pedicle screw at the correct angle helps to assure a mechanically sound construct and to avoid injury to surrounding structures such as the spinal cord, nerve roots, and blood vessels. The orientation of the screw can be determined, for example and in certain situations, in two planes: (1) the transverse plane, which is parallel to the ground if the person is standing upright, and (2) the sagittal plane, which divides a person into left and right halves.

Surgeons use a variety of mechanisms to ensure that the pedicle screw is placed at the correct angle. However, these machines are typically costly and bulky, thereby reducing the number of available surgical suites that have suitable equipment for use in assisting a surgeon with properly placing and orienting a pedicle screw.

SUMMARY

This summary is provided to introduce a selection of embodiments and aspects that are further described below in the detailed description. This summary is not intended to identify key or essential features of the claimed subject matter, nor is it intended to be used as an aid in limiting the scope of the claimed subject matter.

In a first general aspect, an apparatus for use with an electronic device for alignment of a medical tool for positioning a surgical hardware device. The apparatus includes a case configured to secure the electronic device such that the electronic device is secured to the case and does not move relative to the case. The case includes an opening configured to couple with at least a portion of the medical tool. The electronic device is secured relative to the medical tool through the coupling of the case to the at least the portion of the medical tool, the medical tool positioned at a known angle to the case in at least one plane. The electronic device is configured to simulate a three-dimensional position of the surgical hardware device in a body using a diagnostic representation of at least a portion of the body. The electronic device is secured in the case and coupled to the medical tool assists with the alignment of the medical.

In another general aspect, an attachment apparatus is provided to secure a medical alignment device to align a tool. The attachment apparatus includes a base wall configured to provide a base alignment surface adjacent a first portion of the medical alignment device, wherein the medical alignment device is operable to provide a three-dimensional alignment of the tool at a desired insertion angle. The attachment apparatus includes a first side wall providing a side alignment surface adjacent a second portion of the medical alignment device. The attachment apparatus includes an alignment support positioned relative to the base wall and configured to align with a portion of the tool, wherein the medical alignment device provides a notification when the medical alignment device aligned with the tool is provided at the three-dimensional alignment of the insertion angle.

In another general aspect, a system for aligning a medical tool to a desired orientation relative to a patient is provided. The system includes a medical alignment device having an orientation sensor and a processor configured to simulate a positioning of the medical tool using at least one image of at least a portion of a body of the patient to determine a desired alignment angle of the medical tool relative to the body, determine an orientation of the medical alignment device using the orientation sensor, and output a notification when the orientation of the medical alignment device is such that the medical alignment device is positioned at or about the desired alignment angle of the medical tool relative to the body, wherein the notification includes one or more of a sound, a vibration, or a graphical indicator. The system further includes an attachment apparatus to secure the medical alignment device and to align the medical tool. The attachment apparatus includes a base wall configured to provide a base alignment surface adjacent a first portion of the medical alignment device, a first side wall providing a side alignment surface adjacent a second portion of the medical alignment device, and an alignment support positioned relative to the base wall and configured to align with a portion of the medical tool. The medical alignment device provides the notification when the medical alignment device aligned with the medical tool is provided at the desired alignment angle.

BRIEF DESCRIPTION OF THE DRAWINGS

For a more complete understanding of various embodiments and implementations described herein, and the advantages thereof, reference is now made to the following brief description, taken in connection with the accompanying drawings, detailed description, and disclosure, wherein like reference numerals represent like parts, and in which:

FIGS. 5B, 5C, and 5D illustrate example flowcharts for methods for indicating the sagittal angle, transverse angle, and coronal angle, respectively, in accordance with one or more embodiments of the present disclosure;

FIGS. 6A-6D illustrate example user interfaces for a computer-implemented program to perform the methods shown in FIGS. 5A-5D, wherein FIG. 6A illustrates an interface for selecting vertebra of a patient, FIG. 6B illustrates aligning the longitudinal axis of the apparatus with the sagittal plane, FIG. 6C illustrates defining a pedicle screw's position and its sagittal angle, and FIG. 6D illustrates generating an angle-indicative line for showing the angle between the longitudinal axis of the apparatus and the sagittal plane;

FIG. 28 illustrates an example flowchart for a method of determining an orientation of an instrument for inserting a medical device in a bone by rotating the orientation about an insertion point;

Like elements are indicated with like reference numerals.

DETAILED DESCRIPTION

Figure 1:
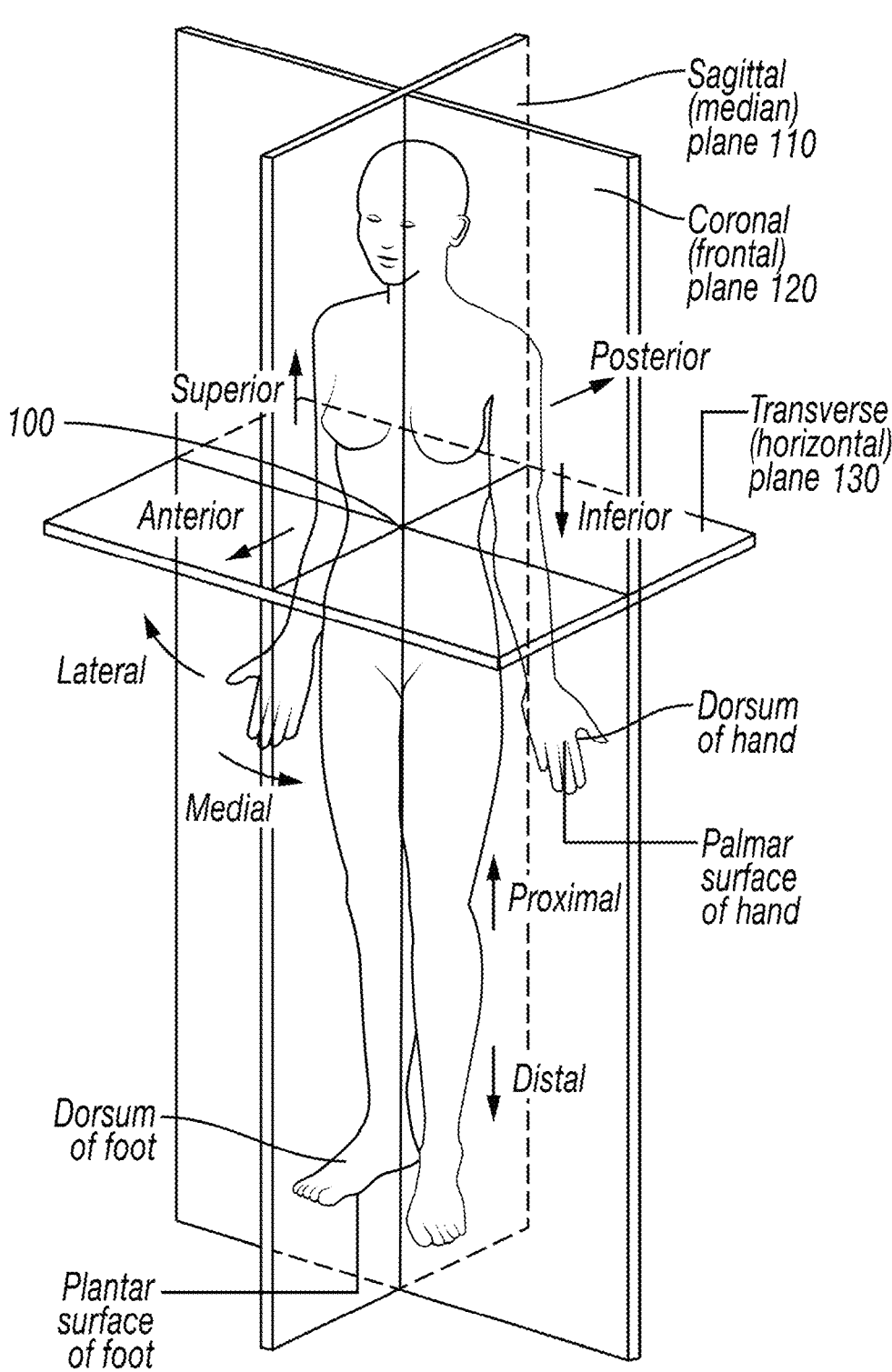
FIG. 1 illustrates definitions of a sagittal plane, a frontal plane, and a transverse plane relative to a patient's body.

In the following detailed description and the attached drawings and appendices, numerous specific details are set forth to provide a thorough understanding of the present disclosure. However, those skilled in the art will appreciate that the present disclosure may be practiced, in some instances, without such specific details. In other instances, well-known elements have been illustrated in schematic or block diagram form in order not to obscure the present disclosure in unnecessary detail. Additionally, for the most part, specific details, and the like, have been omitted inasmuch as such details are not considered necessary to obtain a complete understanding of the present disclosure, and are considered to be within the understanding of persons of ordinary skill in the relevant art.

It is further noted that, unless indicated otherwise, all functions described herein may be performed in hardware or as software instructions for enabling a computer, radio or other device to perform predetermined operations, where the software instructions are embodied on a computer readable storage medium, such as RAM, a hard drive, flash memory or other type of computer readable storage medium known to a person of ordinary skill in the art. In certain embodiments, the predetermined operations of the computer, radio or other device are performed by a processor such as a computer or an electronic data processor in accordance with code such as computer program code, software, firmware, and, in some embodiments, integrated circuitry that is coded to perform such functions. Furthermore, it should be understood that various operations described herein as being performed by a user may be operations manually performed by the user, or may be automated processes performed either with or without instruction provided by the user.

This disclosure describes an attachment apparatus to secure a device, such as a medical alignment device to align a tool. The attachment apparatus is not fully disclosed until after the medical alignment device is described. Although the medical alignment device is a term used herein, it does not have to concern a "medical" procedure and may be considered an alignment device with application to medical procedures or any situation in which a three-dimensional alignment angle is needed or desired. The alignment device is illustrated herein as a medical alignment device in the context of installing one or more pedicle screws at a desired three-dimensional alignment angle (also referred to as a three-dimensional insertion angle) in the vertebra of a patient. Thus, the present disclosure focuses primarily on a system for indicating an angle formed for drilling a pilot hole (also referred to herein as a tract) for receiving a pedicle screw. Tools used to create such a pilot hole and/or to install or screw in a pedicle screw may use such a system to ensure the correct or desired alignment/insertion angle is being provided. In certain implementations, a reference plane such as, for example, the sagittal plane may be used.

The attachment apparatus, described more fully below in connection with FIGS. 19-24, may secure an electronic alignment device, also referred to herein as a medical alignment device, and enables accurate and precise alignment between the alignment device and a tool, such as a medical tool, for performing a function, such as an operation on a patient or installing a pedicle screw. The alignment device is operable to provide accurate alignment between the medical tool and a desired orientation relative to the patient, such as, for example, an insertion of pedicle screws at the desired alignment angle or orientation. The desired angle may be a three-dimensional alignment (or insertion) angle, a transverse angle, sagittal angle, or any other angle. Certain alignments are used, in some embodiments, for the creation of pilot holes, such as pilot holes for the installation of pedicle screws.

The attachment apparatus may include structural features, such as surfaces for positioning adjacent to (or abutting with) the alignment device, and thus providing an accurate reference plane to, a surface of the electronic alignment device. The attachment apparatus may further include at least two side surfaces, or side edges, or side extrusions, for frictionally fitting side surfaces of the electronic alignment device. For example, the attachment apparatus may include two side surfaces or edges distanced less than a width of the electronic alignment device and applying a clamping force on the electronic alignment device when inserted therein. The clamping force produces a friction securing the electronic alignment device to the attachment apparatus. The attachment apparatus may align with or adjacent a tool, such as a medical tool, using an alignment support, and possibly a coupling or mating configuration.

FIG. 1 illustrates a sagittal or median plane 110, a frontal or coronal plane 120, and a horizontal or transverse plane 130 relative to a patient's body part 100 located at the intersection of the sagittal plane 110, the coronal plane 120, and the transverse plane 130. Each plane is orthogonal to each other such that if the position or orientation of an object, device, or medical hardware, such as a pedicle screw, is known in two of the orthogonal planes, the three-dimensional orientation angle of such item may be calculated or known. When discussing a vertebra (or other body parts) in the following disclosure, reference is made to the sagittal plane, coronal plane, and transverse plane. It should be understood that, when these planes are mentioned, they are not intended as a reference only to the specific sagittal, coronal, and transverse planes illustrated in FIG. 1, but rather, are intended as a reference to illustrate an orientation or location relative to the specific vertebra or body part being discussed.

Figure 2A:
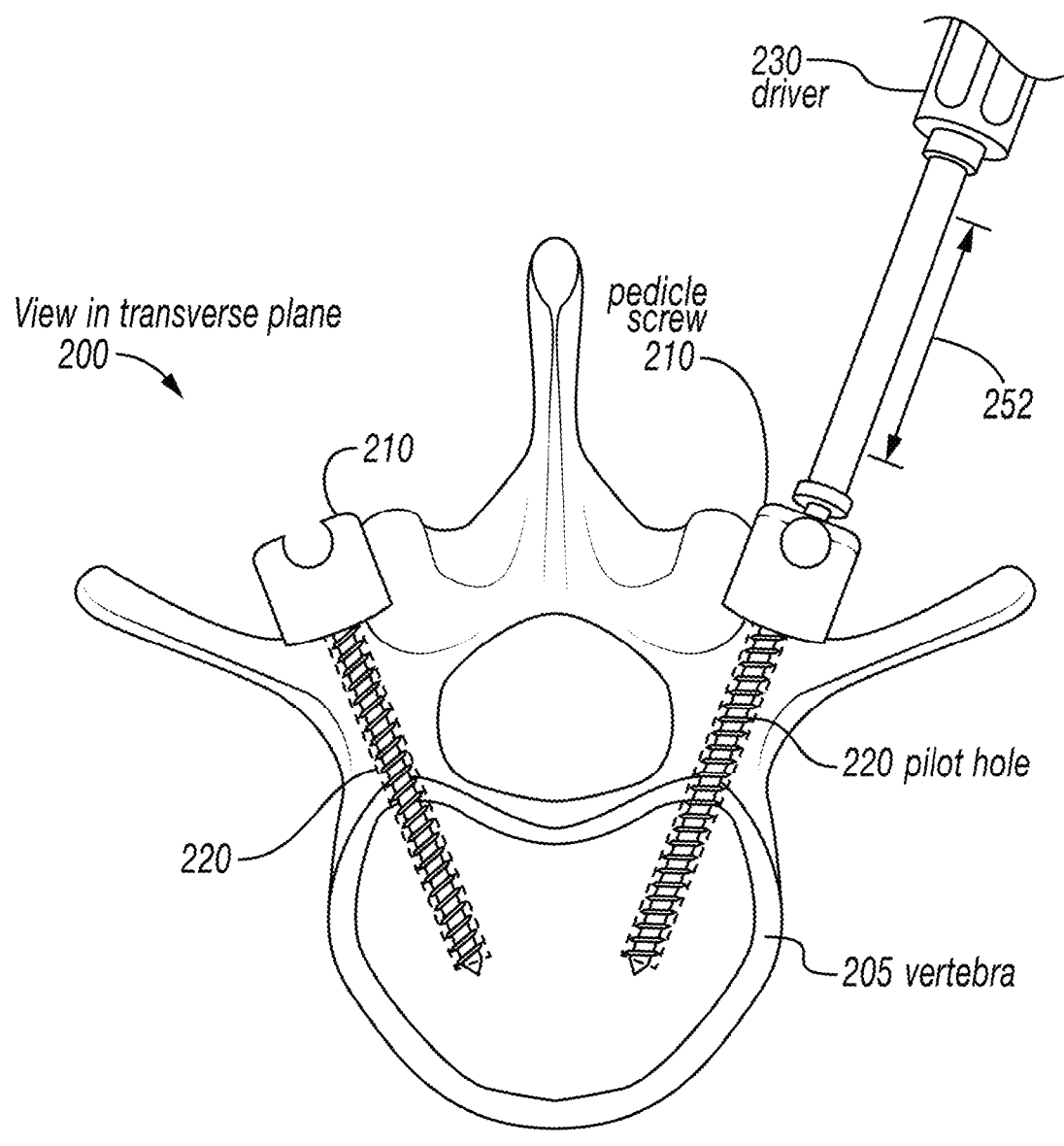
FIG. 2A illustrates a cross-sectional, axial view of a vertebra having pedicle screws installed in respective pilot holes.
Figure 2B:
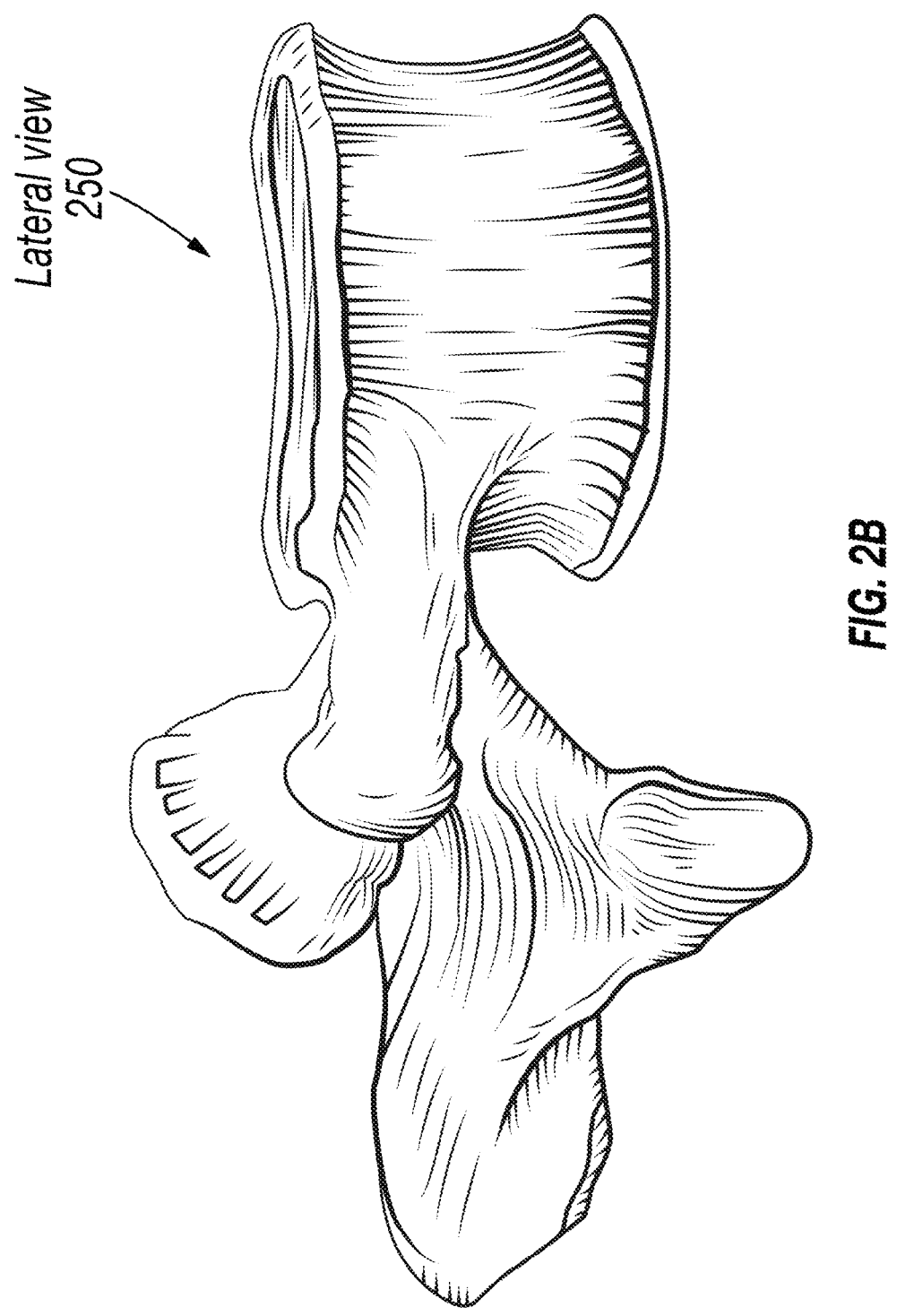
FIG. 2B illustrates an example lateral view of a vertebra for installing pedicle screws.
Figure 2C:
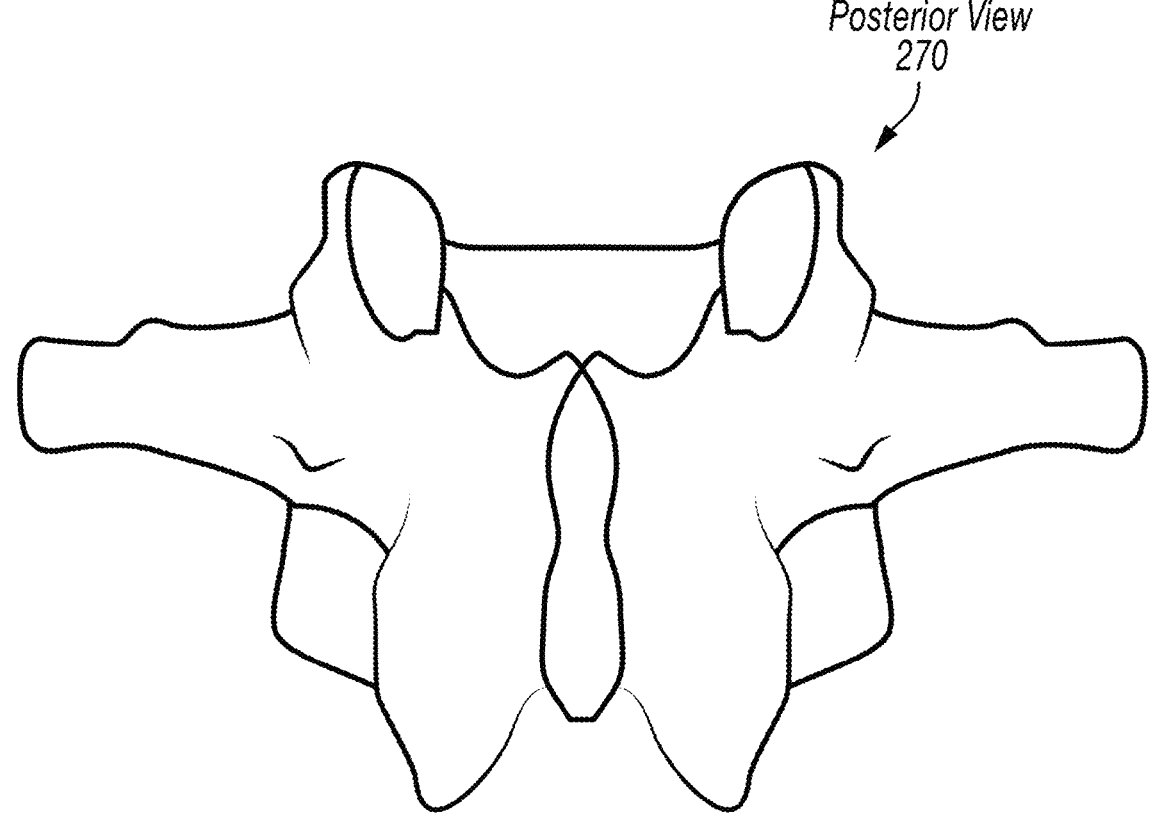
FIG. 2C illustrates an example posterior view of a vertebra for installing pedicle screws.

FIG. 2A illustrates a cross-sectional, axial view (may be referred to as a superior view) 200 of a vertebra 205 having pedicle screws 210 installed in respective pilot holes 220. A driver 230 may be used to screw the pedicle screws 210 positioned in pilot holes 220. Various shapes and types of pedicle screws 210 and driver 230 may be used. The pedicle screws 210 and driver 230 shown in FIG. 2A are for illustrative purpose only. A mating portion 252 of the driver 230, which may be referred to as a tool or a medical tool, may be provided to allow a medical alignment device in an attachment apparatus to "mate" or position adjacent such mating portion 252 to ensure that the driver 230 is installing the pedicle screw at a desired alignment angle, such as a three-dimensional alignment angle. FIG. 2B illustrates a lateral view (i.e., side view) 250 of a vertebra, which could be an orthogonal view of the vertebra 205 of FIG. 2A. FIG. 2C illustrates a posterior view 270 of a vertebra. The following discussion focuses on properly creating the pilot holes with a tool guided by the present disclosure.

Figure 3A:
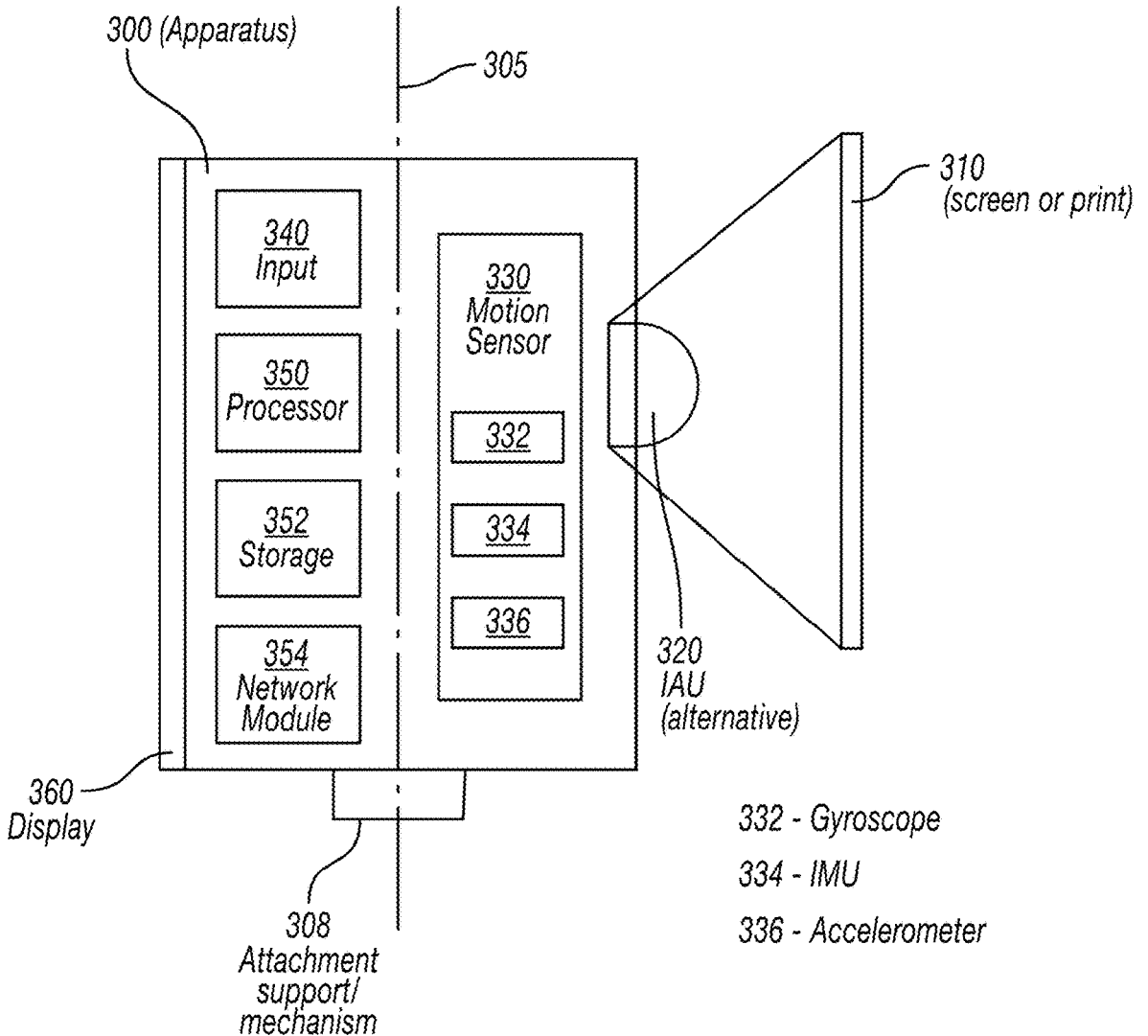
FIG. 3A presents a schematic diagram of an apparatus, which may be referred to as a medical alignment device, used in accordance with an embodiment to define and verify a three-dimensional alignment angle, which may also be referred to as an insertion angle, for use in installing devices, objects, hardware, and the like at a desired alignment angle.

FIG. 3A presents a schematic diagram of an apparatus 300, which may be referred to as a medical alignment device or alignment device, used in accordance with an embodiment to define and verify an angle, such as a three-dimensional alignment angle, for use in installing devices, objects, hardware, and the like, such as to align a pilot hole, or tract, such as the pilot hole 220 of FIG. 2. The apparatus 300 has an axis 305 (such as, for example, a longitudinal axis) that is used in some embodiments to align the apparatus 300 for image capture. The apparatus 300 includes an image acquisition unit 320 (or camera) for capturing an image 310 of the vertebra. In some embodiments, the image 310 may be obtained by positioning the apparatus 300 and/or image acquisition unit 320 in parallel with the transverse, sagittal, or coronal plane to obtain an image of the vertebra. These images may be diagnostic images such as, for example, CT scans, MM scans, X-rays, and the like of items of interest, such as a vertebra. In some implementations, an attachment support and/or mechanism 308 is used to align and/or secure the apparatus 300 to a tool that creates a pilot hole for example.

In some embodiments, the image acquisition unit 320 can be a camera having sufficient field of view 360 to properly align the axis 305 of the apparatus 300 with a desired plane. In some embodiments, the axis 305 is representative of a vertical line centered laterally with respect to the image being captured. For example, if the desired image is intended to capture the vertebra from a cross sectional, axial view (e.g., see FIG. 2A), the axis 305 is aligned with the sagittal plane (i.e., the plane that is sagittal to the vertebra) and the image acquisition unit 320 is positioned parallel to the transverse plane to capture the top-down view of the vertebra shown in FIG. 2A. If the desired image is intended to capture the vertebra from a side view (e.g., a lateral image of the vertebra, see FIG. 2B), the axis 305 is aligned with the transverse plane (i.e., the plane that is transverse to the vertebra) and the image acquisition unit 320 is positioned parallel to the sagittal plane. If the desired image is intended to capture the vertebra from a posterior or anterior view (see, for example, FIG. 2C), the axis 305 is aligned with the sagittal plane and the image acquisition unit 320 is positioned parallel to the coronal plane.

In some embodiments, the image 310 may be a processed diagnostic image, e.g., an image displayed on a screen, a film, or a printed photograph. In other embodiments, the image acquisition unit 320 can directly use an image taken from an external machine (not illustrated), such as a radiograph, computed tomography (CT) scanner, or a magnetic resonance imaging (MRI) machine.

The orientation apparatus 330 is operable to detect changes in movement, orientation, and position. In some embodiments, the orientation apparatus 330 includes at least one of a gyroscope 332, an inertial measurement unit 334, and an accelerometer 336, in other embodiments it may only include the gyroscope 332 with three axes of rotation to be able to determine a three-dimensional orientation of the apparatus 300. The gyroscope 332 is operable to measure at least one axis of rotation, for example, the axis parallel to the intersection of the sagittal plane and the coronal plane. In other embodiments, the gyroscope 332 includes more than one sensing axes of rotation, such as three axes of rotation, for detecting orientation and changes in orientation. The inertial measurement unit 334 can detect changes of position in one or more directions in, for example, a cardinal coordinate system. The accelerometer 336 can detect changes of speeds in one or more directions in, for example, a cardinal coordinate system. In some embodiments, data from all components of the orientation apparatus 330 are used to calculate the continuous, dynamic changes in orientation and position.

The apparatus 300 further includes, in some embodiments, an input component 340 that is operable to receive user input, such as through a keypad or touchscreen, to receive a device, such as a pedicle screw to be installed in a vertebra, insertion location and the desired angle representing an insertion direction of the pedicle screw. An example illustration of the user input component 340 is presented in accordance with FIGS. 6A-6D, as well as FIGS. 12, 13A, 13B, and 18. In some embodiments, the input component 340 can include a multi-touch screen, a computer mouse, a keyboard, a touch sensitive pad, or any other input device.

In some embodiments, the apparatus 300 further includes a processor 350. The processor 350 can be any processing unit capable of basic computation and capable of executing a program, software, firmware, or any application commonly known in the art of computer science. As to be explained, the processor 350 is operable to generate a three-dimensional alignment angle based on alignment inputs from to views orthogonal to one another, and to output an angle-indicative line representing the orientation of a device, such as a pedicle screw, pilot hole, etc. on the display showing a diagnostic image where the device, such as a pedicle screw, is to be installed. In some embodiments, the angle-indicative line provides a notation that the orientation of the apparatus 300 approximately forms the desired angle. The angle-indicative line is not limited to showing sagittal angles, but also angles in different planes, such as, for example, the coronal plane or the transverse plane.

The apparatus 300 may, in some embodiments, further include a memory storage unit 352 and network module 354. The memory storage unit 352 can be a hard drive, random access memory, solid-state memory, flash memory, or any other storage device. Memory storage unit 352 saves data related to at least an operating system, application, and patient profiles. The network module 354 allows the apparatus 300 to communicate with external equipment as well as communication networks.

In some embodiments, the apparatus 300 further includes a display 360. In some embodiments, the display 360 is a liquid crystal display that also serves as an input using a multi-touch screen. In some embodiments, the display 360 shows the angle-indicative line to a user and provides a notification when the apparatus is approximately aligned with the predefined desired angle, as determined by the gyroscope 332 or the orientation apparatus 330. For example, the notification can include a highlighted line that notifies the user the axis 305 has reached the desired angle, or is within an acceptable range of the desired angle. The apparatus 300 may provide any number of notifications to a user, including visual, auditory, and tactile, such as, for example, vibrations. The apparatus 300 will include a speaker as well as a device to impart vibrations to a user to alert or notify a user.

Figure 7:
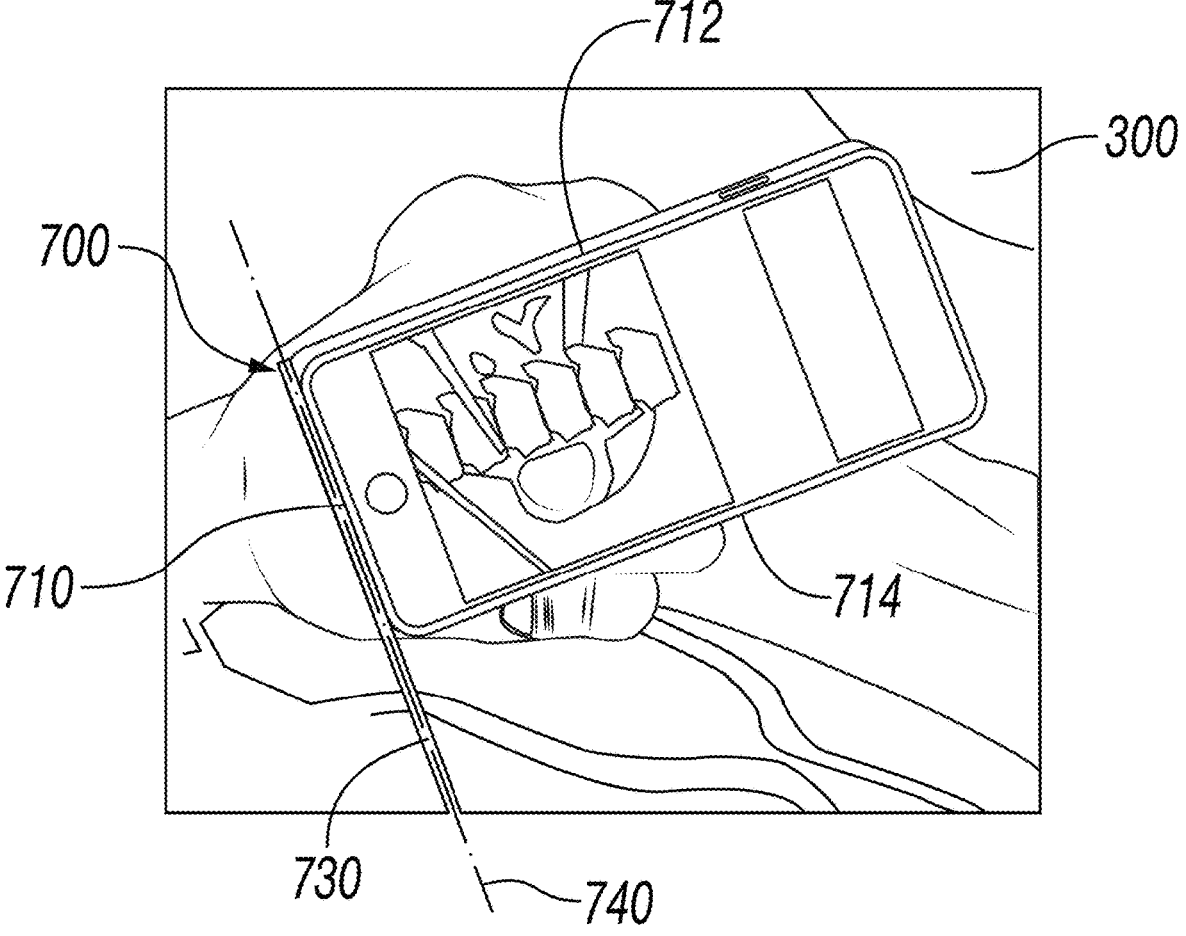
FIG. 7 illustrates an example of aligning the apparatus or medical alignment device.

Referring briefly to FIG. 7, in some implementations, the apparatus 300 (i.e., the medical alignment device) further includes an attachment support or mechanism 700 (also 308 of FIG. 3A) (i.e., the attachment apparatuses 1900 and 2200, detailed illustrated in FIGS. 19-24) that allows the medical alignment device or apparatus 300 to be attached or provided adjacent to a tool, medical hardware, or equipment (i.e., a medical tool 730). The attachment apparatus 700 may be made of plastic, stainless steel, titanium, or any other material. The attachment apparatus 700 couples to the medical alignment device or apparatus 300 to the tool 730 by, for example, providing a casing that is attached to the medical alignment device 300 and is configured to connect to or abut the medical tool 730, for example, by aligning a first surface 710 of the medical alignment device 300 to the attachment apparatus 700 and thus to the medical tool 730. For example, the attachment apparatus 700 may be aligned to a longitudinal axis 740 of the medical tool 730. As such, orientation sensors in the medical alignment device 300 are properly aligned with the longitudinal axis 740.

In other implementations, a second surface 712 and a third surface 714 of the medical alignment device 300 may be used to secure and/or align the medical alignment device 300 to the attachment apparatus 700. In some embodiments, the attachment apparatus 700 may include a magnetic attachment apparatus for coupling the medical alignment device 300 to the tool 730 or to the attachment apparatus 700. The attachment apparatus 700 allows the medical alignment device 300 to provide real-time measurement and display of the orientation of the attached or aligned medical tool 730. Two example embodiments of the attachment apparatus are illustrated in FIGS. 19-24.

Turning now to FIGS. 19-24, FIGS. 19-21 illustrate a first embodiment of the attachment apparatus 1900, respectively in a perspective view, a front view, and a cross-sectional side view. The attachment apparatus 1900 may be used in the place of the attachment support/apparatus 308 of FIG. 3A. The attachment apparatus 1900 includes a base wall 1910 providing a base alignment surface 1912 for abutting the first surface 710 of the medical alignment device 300 in FIG. 7, and a first side wall 1920 providing a side alignment surface 1922 for abutting the second surface 712 of the medical alignment device 300. The attachment apparatus 1900 may further include an alignment support 1905. The alignment support 1905 may extend from the base wall 1910 and can be configured to couple with a mating portion 252 (for example, shown in FIG. 2A) of the tool (e.g., such as the driver 230 or the medical tool 730). The alignment support 1905 and the mating portion 252 are operable to align such that a constant or known angular relationship is provided. As a consequence, the relationship or positioning relative to the medical alignment device 300 positioned in the attachment apparatus 1900 is known.

In some embodiments, the attachment apparatus 1900 further includes a second side wall 1925 providing a second side alignment surface 1927 for mating with part of the medical alignment device 300, such as the third surface 714. The second side wall 1925 and the first side wall 1920 may provide a secure fit when the medical alignment device 300 is inserted into the attachment apparatus 1900. The secure fit may be provided by a frictional force produced when the distance between the first side wall 1920 and the second side wall 1925 is slightly less than the width between the second face 712 and the third face 714 of the medical alignment device 300. This dimensional difference slightly compresses or holds the medical alignment device 300 and slightly bends the attachment apparatus 1900, thus creating a clamping force that results in the frictional force.

In some embodiments, the secure fit may be provided by one or more engagement protrusions 1940 on either one or both of the first and the second side walls 1920 and 1925. In the example as shown, the engagement protrusions 1940 may be a lip or edge that is operable to embrace or contain a thickness of the medical alignment device 300. A similar tight fit by a dimensional difference between a distance of the extrusion 1940 to the back surface 1915 and the thickness of the medical alignment device 300 can produce a frictional force securing the medical alignment device in the attachment apparatus 1900. In other examples, though not illustrated, one or more protrusions on the side walls 1920 and 1925 may fit with corresponding one or more notches (not shown) in the medical alignment device 300. Other configurations to secure the medical alignment device 300 to the attachment apparatus are possible, including a magnetic fit.

As shown, the attachment apparatus 1900 further includes a finger profile 1930 positioned adjacent the side walls 1920 and 1925 for receiving fingers of a user when held. For example, the finger profile 1930 can include one or more curved surfaces sized to fit a human finger such that the finger profile 1930 provides a greater surface of contact than a flat profile does. The finger profile 1930 may include one or more round or concave curves to receive fingers of the user to reduce slippage. In the embodiment as illustrated, each side wall 1920 and 1925 provides three curved surfaces such that the alignment apparatus 1900 may be held by engaging a thumb on one side and three other fingers on the other side. In other embodiments, each side wall 1920 and 1925 may provide more or fewer number of curved surfaces.

As shown, the alignment support 1905 can extend from and be perpendicular to the base wall 1910. In some embodiments, the alignment support 1905 may be rotatable about the base wall 1910, such as hinged for example, to provide an adjustable angular relationship between the base wall 1910 and the alignment support 1905. In some embodiments, the alignment support 1905 may be affixed onto the base well 1910 using a fastener or the like. In a different configuration, such as that shown in FIGS. 22-24, the alignment support 1905 may be parallel to the base wall 1910.

In some embodiments, to secure the medical alignment device 300, the base wall 1910 and its alignment surface 1912, and the first side wall 1920 and its alignment surface 1922 of the attachment apparatus 1900, form a matching profile (e.g., such as a rounded rectangle, a chamfered rectangle, or any shapes conforming to the shape of the medical alignment device 300). As shown, the base wall 1910 and the first side wall 1920 form a matching profile of two perpendicular sides to conform to the first surface 710 and the second surface 712 of the medical alignment device 300.

Figure 20:
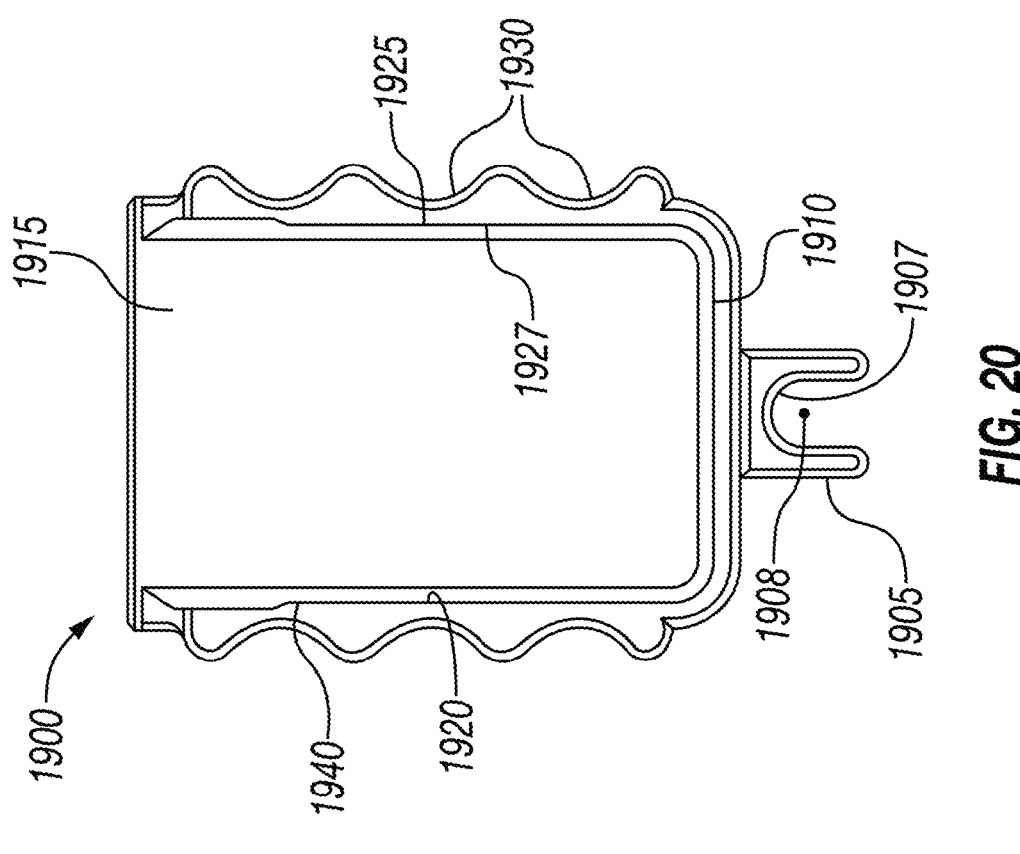
FIG. 20 illustrates a front view of the embodiment of the attachment apparatus of FIG. 19.
Figure 19:
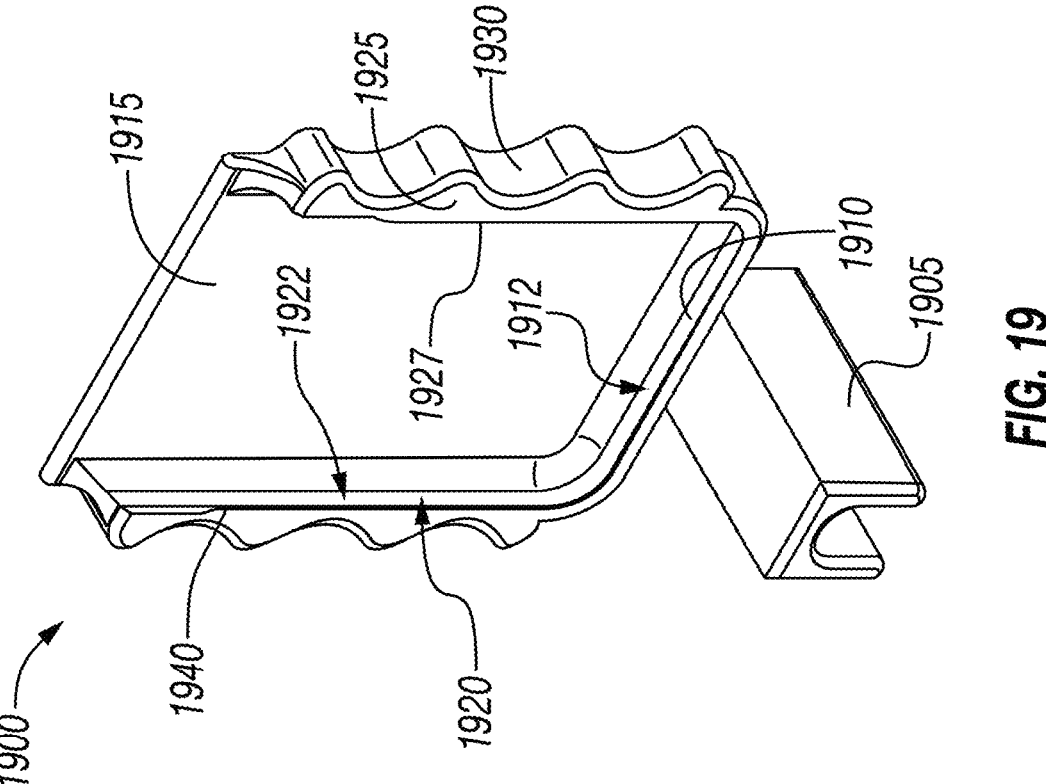
FIG. 19 illustrates a perspective view of an embodiment of the attachment apparatus.
Figure 22:
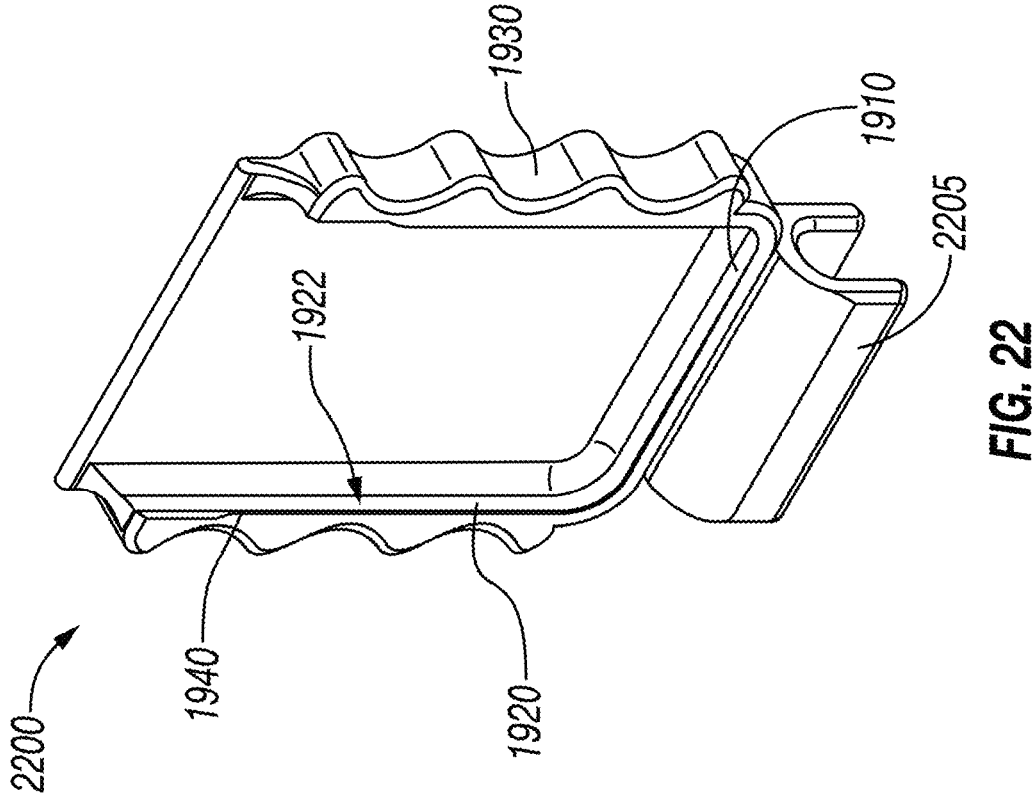
FIG. 22 illustrates a perspective view of another embodiment of the attachment apparatus.
Figure 21:
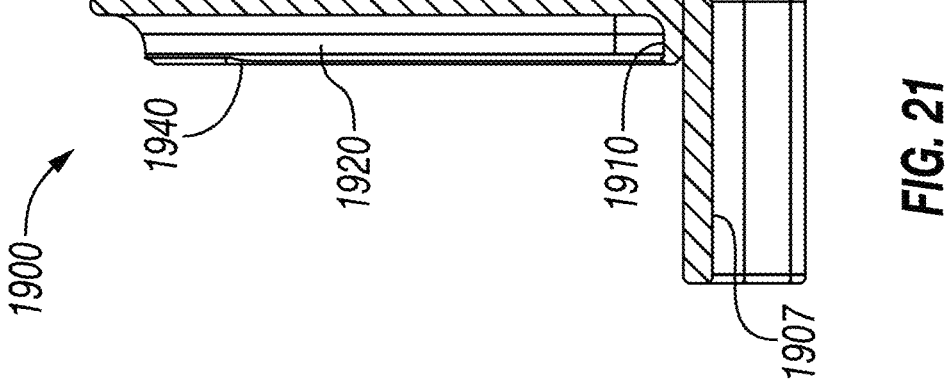
FIG. 21 illustrates a cross-sectional side view of the embodiment of the attachment apparatus of FIG. 19.
Figure 24:
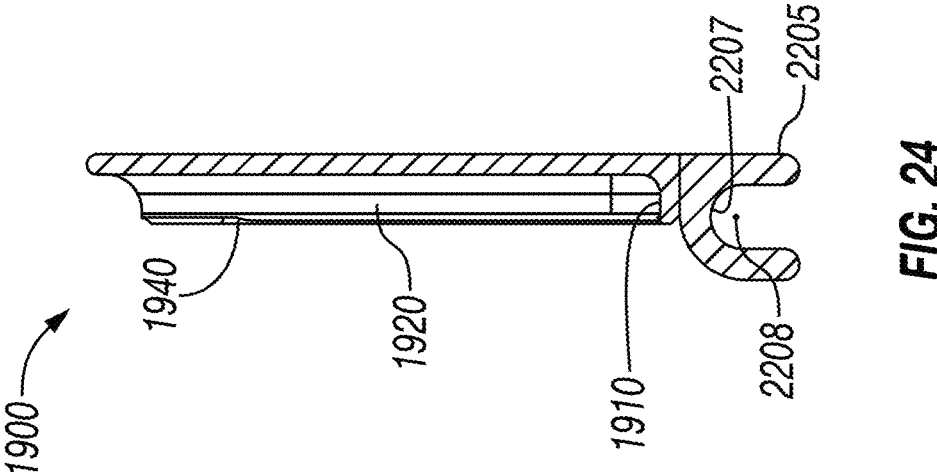
FIG. 24 illustrates a cross-sectional side view of the other embodiment of the attachment apparatus of FIG. 22.
Figure 23:
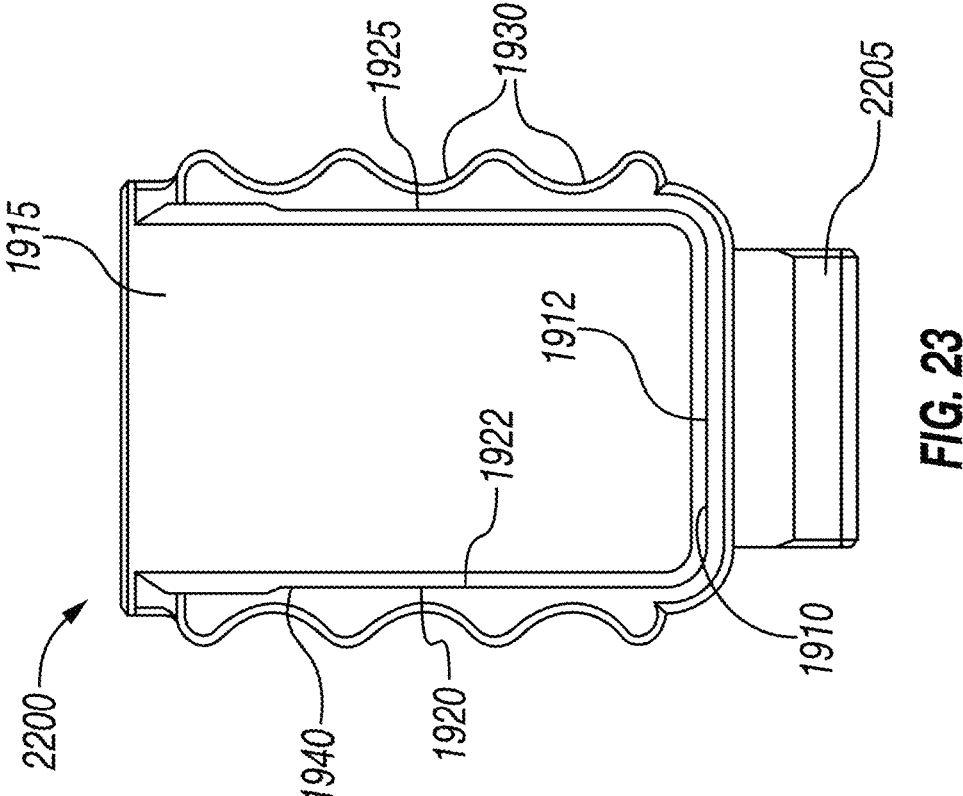
FIG. 23 illustrates a front view of the other embodiment of the attachment apparatus of FIG. 22.

In some embodiments, the mating portion 252 of the tool (such as the driver 230) is a cylindrical portion that is engageable or mateable to the alignment support 1905 of the attachment apparatus 1900 at different locations of the tool 230 along the longitudinal axis 740 of the tool 730 or the tool 230. For example, as shown in FIG. 20, the alignment support 1905 includes an inner surface 1907 (also called an alignment surface of the alignment support 1905) having a half-cylindrical profile around the axis 1908. When the alignment support 1905 is coupled to or positioned adjacent to the tool 230 or 730, the longitudinal axis of the tool 230 (or the tool 730) is aligned with the axis 1908 to provide proper alignment.

In some embodiments, the at least one of the base wall 1910 or the first side wall 1920 of the attachment apparatus 1900 is magnetically attracted to the medical alignment device 300 to secure the medical alignment device 300 thereon. For example, the first side wall 1920 may be embedded with a magnet and the medical alignment device 300 can include ferromagnetic components to interact with the embedded magnet. In other embodiments, the medical alignment device 300 itself may include one or more magnets and the attachment apparatus 1900 may be made of a ferromagnetic material.

Similar to FIGS. 19-21, FIGS. 22-24 illustrate a second embodiment of the attachment apparatus 2200, respectively in a perspective view, a front view, and a cross-sectional side view. In the second embodiment, the alignment support 2205 is parallel to the base wall 1910. The alignment support 2205 includes an inner surface 2207 (also called an alignment surface) coupleable to or aligned adjacent to the mating portion 252 of the tool 230 or the tool 730. The inner surface 2207 may have a half-cylindrical profile around the axis 2208, which is aligned with the longitudinal axis 740 when the alignment support 2205 is coupled with the mating portion 252. In certain embodiments, the inner surface 2207 of the alignment support 2205 may include an adhesive, semi-tacky material, conforming, slip-resistant material, or conforming material to allow the attachment apparatus 2200 holding the medical alignment device 300 to mate our couple more easily with the tool 230 or the tool 730 at a desired mating portion 252. The mating portion 252 of the tool 230 or the tool 730 may be coupleable to or alignable with the alignment support 2208 of the attachment apparatus 300 at different locations of the tool 730 or the tool 230 along the longitudinal axis 740.

Figure 31:
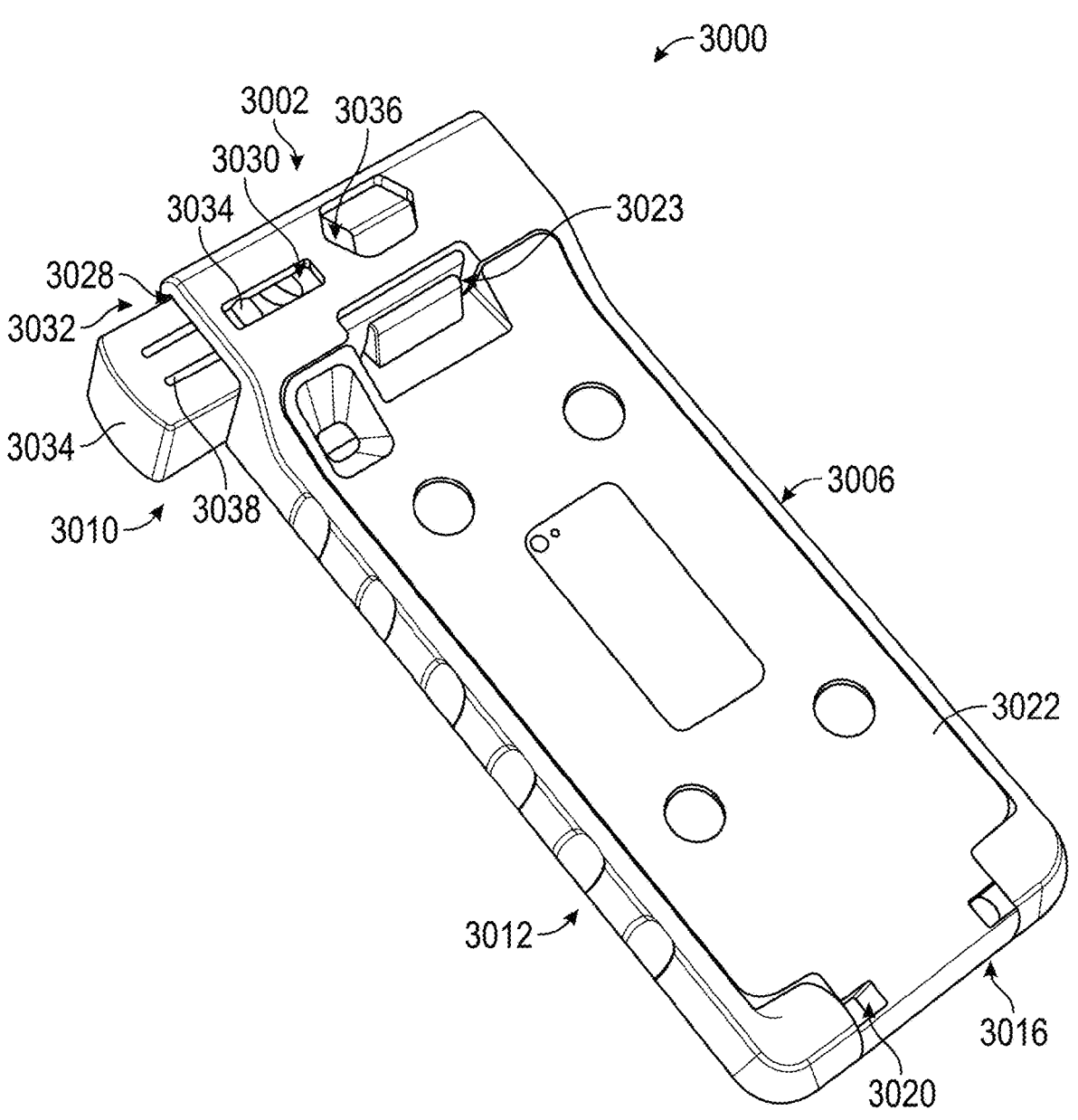
FIG. 31 illustrates a perspective view of a holder for a medical device.
Figure 32:
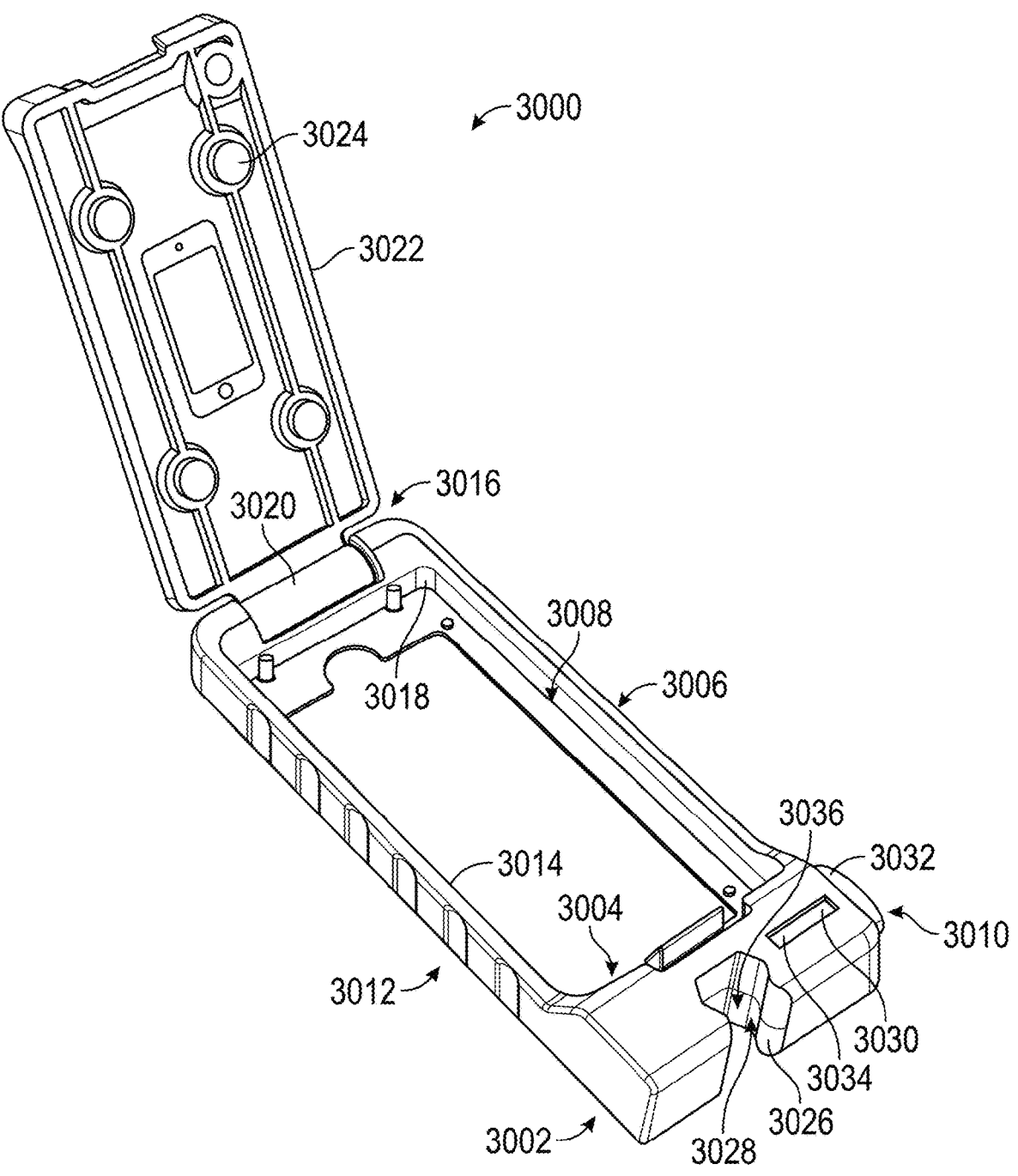
FIG. 32 illustrates a perspective view of a holder for a medical device.

Turning now to FIGS. 31 and 32, a third embodiment of an attachment apparatus 3000 (e.g., a case). The attachment apparatus 3000 includes a base wall 3002 providing a base alignment surface 3004 for abutting the first surface 710 of the medical alignment device 300 (e.g., mobile device, cellphone, smart watch, IoT device, etc.) in FIG. 7, and a first side wall 3006 providing a side alignment surface 3008 for abutting the second surface 712 of the medical alignment device 300. The attachment apparatus 3000 may further include an alignment support 3010 (e.g., a holding mechanism). The alignment support 3010 may extend along the base wall 3002 and can be configured to couple with a mating portion 252 (for example, shown in FIG. 2A) of the tool (e.g., such as the driver 230 or the medical tool 730). The alignment support 3010 and the mating portion 252 are operable to align such that a constant or known angular relationship is provided. As a consequence, the relationship or positioning relative to the medical alignment device 300 positioned in the attachment apparatus 3000 is known. For instance, the known angular relationship may be any desired angle. In various embodiments, the known, or desired angle, may be 90 degrees (i.e., the medical tool is positioned perpendicular to the case).

In some embodiments, the attachment apparatus 3000 further includes a second side wall 3012 providing a second side alignment surface 3014 for mating with part of the medical alignment device 300, such as the third surface 714. The second side wall 3012 and the first side wall 3006 may provide a secure fit when the medical alignment device 300 is inserted into the attachment apparatus 3000. The secure fit may be provided by a frictional force produced when the distance between the first side wall 3006 and the second side wall 3012 is slightly less than the width between the second face 712 and the third face 714 of the medical alignment device 300. This dimensional difference slightly compresses or holds the medical alignment device 300 and slightly bends the attachment apparatus 3000, thus creating a clamping force that results in the frictional force. The attachment apparatus 3000 may be manufactured to accommodate various sized of the medical alignment device 300. For instance, the medical alignment device 300 may be an iPod™, a phone (e.g., iPhone™ 14, iPhone™ 10, etc.), a tablet (e.g., iPad™), a smart watch (e.g., Apple Watch™ Series 8, Apple Watch™ Series 5), or any other electronic device configured for these purposes. As such, the attachment apparatus 3000 may be available in multiple sizes, sized and shaped to fit the respective medical alignment device 300. It should also be understood that the attachment apparatus 3000 can accommodate a medical alignment device 300 that includes a case.

Figure 30:
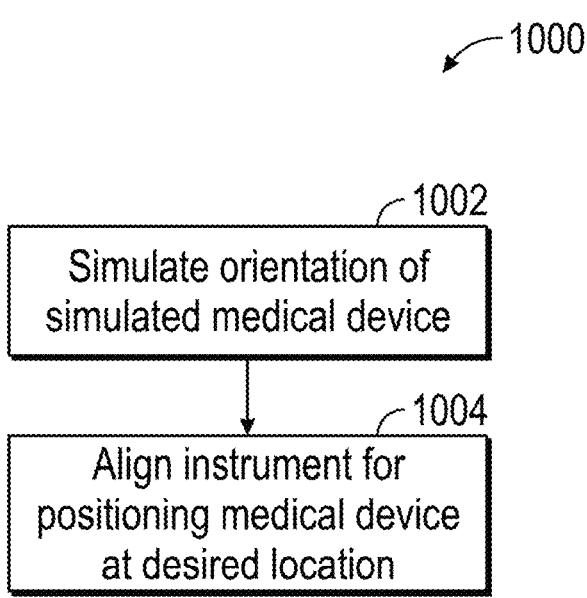
FIG. 30 illustrates an example flowchart for a method for determining orientation of an instrument for positioning a medical device in a body.

For example, the attachment apparatus may be smaller than shown in FIGS. 30-31 to accommodate a smart watch. In the following example, the distance between the first side wall 3006 and the second side wall 3012 may be smaller or reduced (e.g., from 2.8 inches to 38 mm), the distance between the top wall 3016 and the base wall 3002 may smaller or reduced (e.g., from 5.8 inches to 44 mm), and the depth of the attachment apparatus 3000 may be smaller or reduced. However, it should also be understood that retrofitted cases can be attached a medical alignment device 300 to fit within attachment apparatus 3000 without requiring a different attachment apparatus 3000 for each medical alignment device 300. Accordingly, the attachment apparatus 3000 can be a universal attachment apparatus that can accommodate a plurality of medical alignment devices 300 based on coupling or attaching a retrofitted case to the particular medical alignment devices 300 to fit within the universal attachment apparatus. Additionally, the engagement protrusions 3024 on the door 3022 may be customizable and modifiable based on the type of medical alignment devices 300 (e.g., phone, watch, tablet, etc.) such that the engagement protrusions 3024 can be adjusted or moved (e.g., removed and reattached to a different position, slid to a different positions).

The attachment apparatus 3000 further includes a top wall 3016 providing a top side alignment surface 3018 for mating with part of the medical alignment device 300. The top wall 3016 is opposite the base wall 3002 such that the top side alignment surface 3018 faces the base alignment surface 3004. The top wall 3016 may include a hinge 3020 coupled to a door 3022. The door 3022 may be configured to close the attachment apparatus 3000. For instance, the base wall 3002, the first side wall 3006, the second side wall 3012, and the top wall 3016 together form a rectangular opening to receive the medical alignment device 300. As such, and as further explained herein, the attachment apparatus 3000 is designed such that the medical alignment device 300 (e.g., an iPhone™, Apple Watch™) does not move relative to the attachment apparatus 3000 (e.g., a case). Once the medical alignment device 300 is placed into the opening (i.e., into the attachment apparatus 3000), the door 3022 may rotate about the hinge 3020 to align with the base wall 3002, the first side wall 3006, the second side wall 3012, and the top wall 3016 to cover and further secure the medical alignment device 300. The door 3022 may be locked into place, or secured to the base wall 3002, via a snap lock 3023. For instance, the snap lock 3023 may include a tongue-and-groove configuration where a flexible flange on the base wall 3002 is configured to mate with a divot on the door 3022, or vice versa.

An interactive portion of the medical alignment device 300 may remain exposed for use by an operator between the base wall 3002, the first side wall 3006, the second side wall 3012, and the top wall 3016 on a side opposite the door 3022 (e.g., a front opening, a window). As such, the door 3022 may include a diagram (e.g., an indicator) on at least one surface of the door indication the recommended orientation of the medical alignment device 300 relative to the attachment apparatus 3000. As discussed herein, the attachment apparatus 3000 may be available in multiple sizes, sized and shaped to fit the respective medical alignment device 300. Therefore, the door 3022 similarly may be designed to accommodate various features of the medical alignment device 300. For instance, the door 3022 may include more than one opening corresponding to a camera lens, a flash, etc.

In some embodiments, the secure fit may be provided by one or more engagement protrusions 3024 on the door 3022. In the example as shown, the engagement protrusions 3024 may be a tab (e.g., foam, sponge, rubber, etc.), a spring, etc. that is operable to embrace the medical alignment device 300. A similar tight fit by a dimensional difference between a distance of the engagement protrusions 3024 and the medical alignment device 300 can produce a frictional force securing the medical alignment device in the attachment apparatus 3000. The friction fit beneficially allows minimal movement between the medical alignment device 300 and the attachment apparatus 3000 for precise navigation/alignment of the medical alignment device 300 and the tool relative to a body of the patient. As illustrated, there may be one or more (e.g., four) of the engagement protrusions 3024. The engagement protrusions 3024 may be even spaced along the door 3022. In other embodiments, the engagement protrusions 3024 may be omitted. Other configurations to secure the medical alignment device 300 to the attachment apparatus are possible, including a magnetic fit. For example, one or more magnetics may be placed on the door 3022 to customizably fit any medical alignment device 300.

In some embodiments, to secure the medical alignment device 300, the base wall 3002 and its alignment surface 3004, and the first side wall 3006 and its alignment surface 3008 of the attachment apparatus 3000, form a matching profile (e.g., such as a rounded rectangle, a chamfered rectangle, or any shapes conforming to the shape of the medical alignment device 300). This provides a reproducible orientation of the medical alignment device 300 every time it is placed in the attachment apparatus 3000. As shown, the base wall 3002 and the first side wall 3006 form a matching profile of two perpendicular sides to conform to the first surface 710 and the second surface 712 of the medical alignment device 300.

Referring now again to the alignment support 3010, the alignment support 3010 may extend along the base wall 3002 and can be configured to couple with a mating portion 252 (for example, shown in FIG. 2A) of the tool (e.g., such as the driver 230 or the medical tool 730). The alignment support 3010 includes an inner alignment surface 3026 having a generally half-cylindrical profile around the axis 740. The inner alignment surface 3026 defines an opening configured to receive the tool such that a cylindrical portion (e.g., the mating portion 252) of the tool (such as the driver 230) is engageable or mateable to the alignment support 3010 at the inner alignment surface 3026 of the attachment apparatus 3000 at different locations of the tool 230 along the longitudinal axis 740 of the tool 730 or the tool 230. In other words, the tool may move along the longitudinal axis within the opening defined by the inner alignment surface 3026. When the alignment support 3010 is coupled to or positioned adjacent to the tool 230 or 730, the longitudinal axis of the tool 230 (or the tool 730) is aligned with the axis of the alignment surface 3014 to provide proper alignment.

The alignment support 3010 further includes a channel 3028 (e.g., an opening, a cavity, etc.). The channel 3028 extends along the base wall 3002. The channel may include a slot 3030. The slot 3030 may be an elongated opening disposed on a side of the channel 3028.

The alignment support 3010 further includes a holding mechanism 3032. The holding mechanism is configured to be received by the channel 3028. The holding mechanism 3032 may be slidably coupled to the channel 3028. For instance, the holding mechanism may be configured to move across a lateral axis, perpendicular to the longitudinal axis. In other words, the alignment support 3010 is configured to move along a plane parallel to a plane of the base wall 3002. The holding mechanism may further be configured to be received by the opening defined by the alignment surface and to secure the case to the medical tool, wherein the medical tool is positioned perpendicular to the case. For instance, the holding mechanism 3032 is configured to apply a force to the medical tool against the case to secure the medical tool relative to the case via at least one of a magnetic fit and a mechanical friction fit, as is explained further herein.

The holding mechanism 3032 includes a main body 3034 movably coupled to the attachment apparatus 3000. The main body 3034 includes a main body opening 3036 disposed on the main body 3034 such that the main body opening 3036 aligns with the opening defined by the inner alignment surface 3026 on the alignment apparatus 3000 when the main body 3034 is moved from a first position to a second position. The first position is illustrated in FIG. 31 and the second position is illustrated in FIG. 32. When the main body 3034 is in the second position (i.e., when the main body opening 3036 and the inner alignment surface 3026 are aligned), the medical device is configured to be placed in the corresponding opening.

The holding mechanism 3032 may include a biasing member (not shown). The biasing member is configured to apply a force to the main body 3034 such that the main body 3034 is biased toward the first position. As such, the holding mechanism 3032 may be a spring-biased plunger, wherein the spring-biased plunger is configured to apply a force to the medical tool against the case to secure the medical tool relative to the case. For instance, a user may press the main body 3034 (e.g., the spring-biased plunger) to move to the second position, insert the tool, and release the main body 3034 to allow the main body 3034 to move back to the first position and apply the corresponding force.

The main body 3034 may include a notch 3034 (e.g., a protrusion). The notch 3034 is configured to be received by the slot 3030 (e.g., the elongated opening of the case). The relationship between the notch 3034 and the slot 3030 prevents the main body from vacating the opening. In various embodiment, the main body 3034 may include at least one slot 3038 disposed on the main body 3034. The at least one slot 3038 corresponding with a protrusion on an inner surface of the opening wherein the protrusion is received by the slot and configured to facilitate alignment of the main body within the case as the main body moves within the opening.

The alignment apparatus 3000 may further include a sanitary drape. In various embodiment, the medical alignment device 300 is cover by the sanitary draft prior to use. For instance, the sanitary drape is configured to enclose the medical alignment device 300 and fit between the medical alignment device 300 and the alignment apparatus 3000 (e.g., the case, between the base wall 3002, the first side wall 3006, the second side wall 3012, and the top wall 3016).

Returning to FIG. 3B, a schematic diagram of an axial view of a vertebra defining an alignment or insertion angle for a pilot hole in the vertebra in this plane for insertion or installation of a pedicle screw is provided. This view or diagnostic image of the vertebra may be electronically transmitted to the medical alignment device 300, or the view or image may be captured from a monitor or display of a diagnostic image using the image acquisition unit 320 of the medical alignment device 300 (sometimes referred to as apparatus 300). A sagittal angle 370 may be defined for the pilot hole 220 in the vertebra 205 that starts at the initial position 375, which may be referred to as the insertion location. The display 360 shows the field of view of the view captured by the image acquisition unit 320, assuming that was how the image was acquired, and allows a user to align the axis 305 of the apparatus 300 with the desired plane (e.g., the sagittal plane). In the embodiment shown in FIG. 3B, the sagittal angle 370 is the angle between the central axis 365 of the pilot hole 220 and the sagittal plane.

Figure 3B:
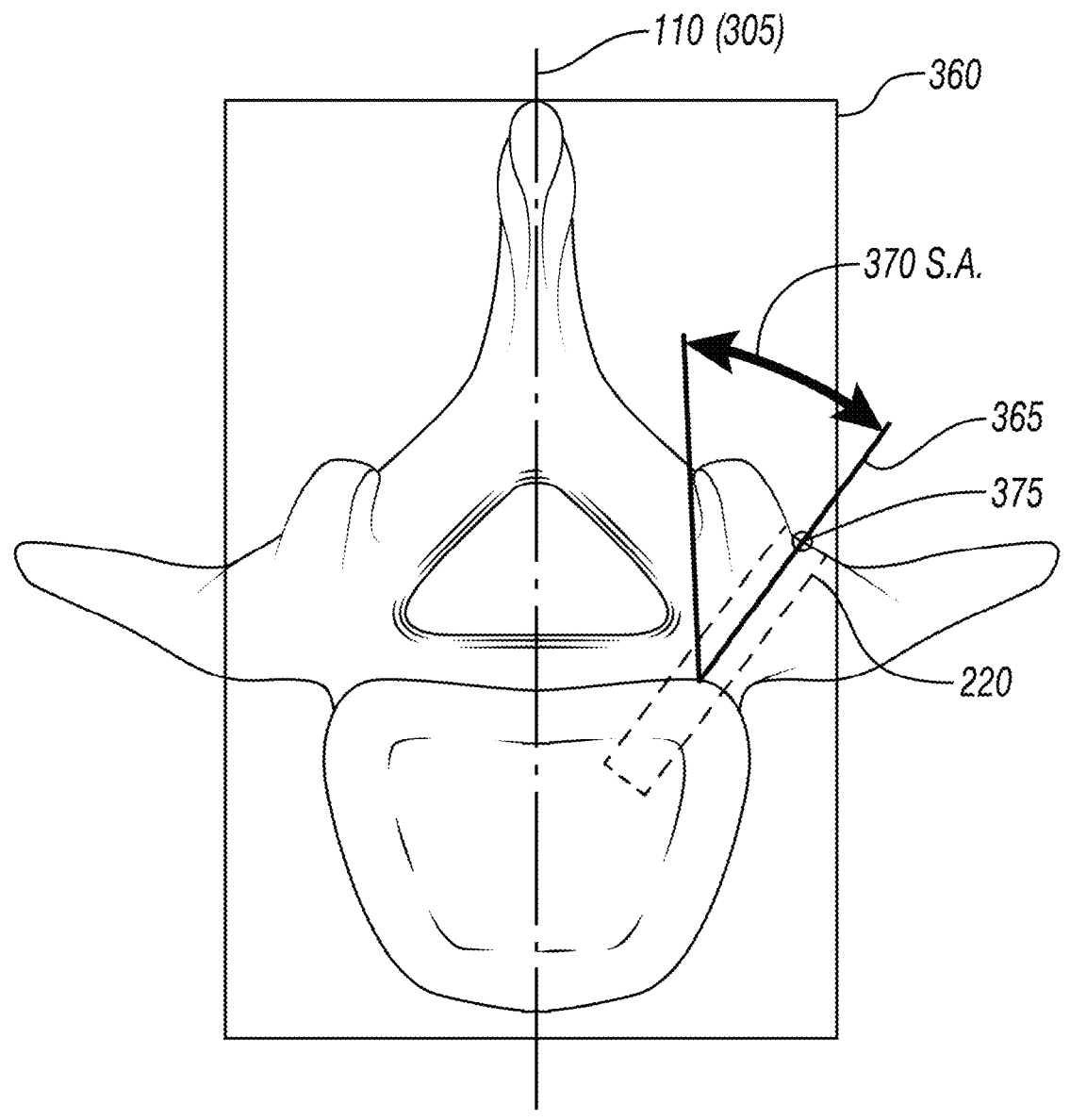
FIG. 3B illustrates a schematic diagram of an axial view of a vertebra for defining an alignment or insertion angle for a pilot hole in the vertebra in this plane.
Figures 4A, 4B:
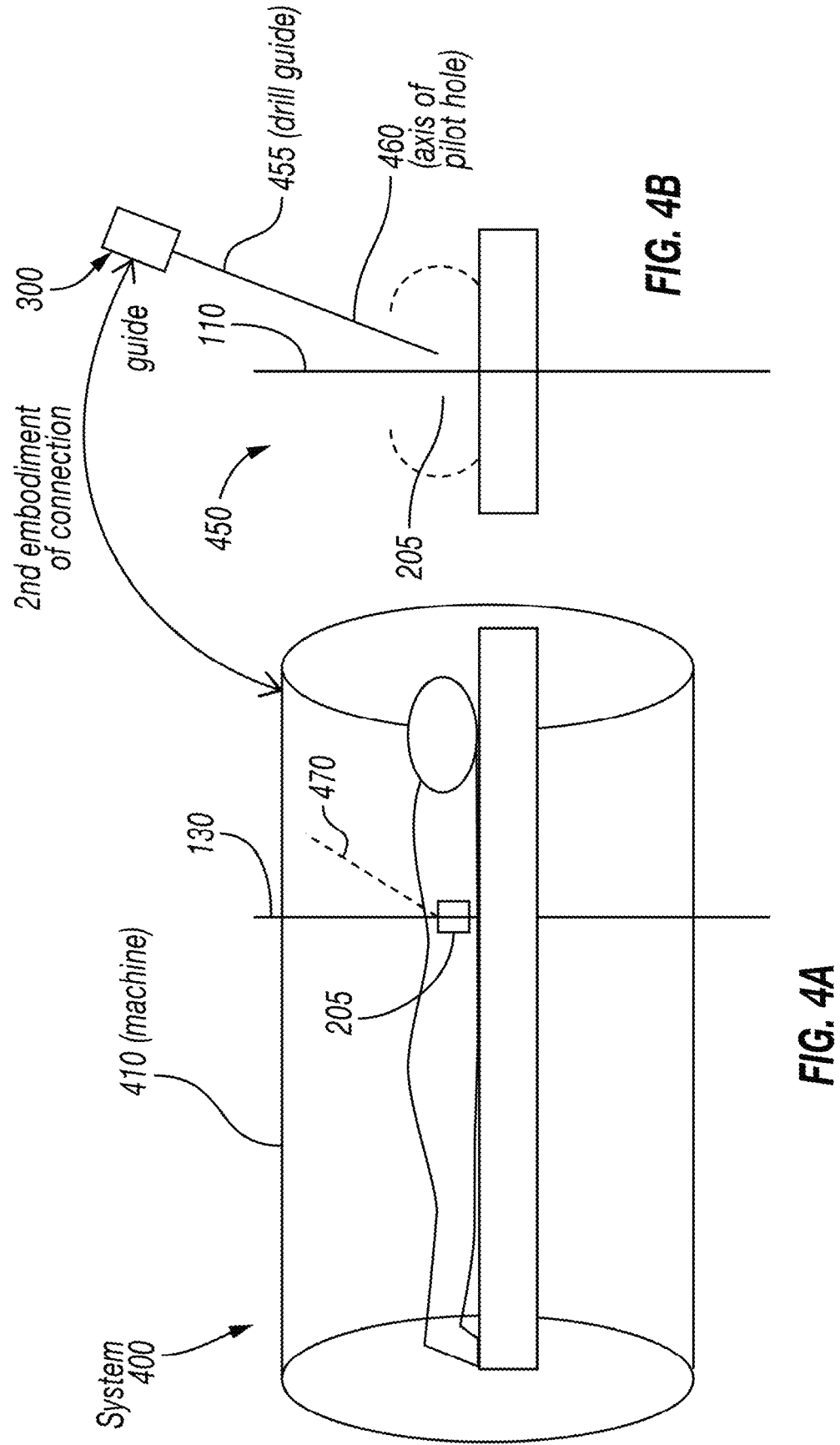
FIG. 4A illustrates a schematic side view of a medical operation system used in some embodiments for defining the sagittal angle of a pilot hole to be made in a vertebra.
FIG. 4B illustrates a schematic front view of a medical operation system used in some embodiments for defining the sagittal angle of a vertebra.

FIG. 4A illustrates a schematic side view of a medical operation system 400 used in some embodiments for defining the sagittal angle 370 of a pilot hole to be made in a vertebra which may be used in some embodiments for defining the sagittal angle 370 of the vertebra shown in FIGS. 3A and 3B. The medical operation system 400 includes a machine 410 for capturing a cross-sectional view of the vertebra 205. The machine 410 may be, for example, a CT scanner or MM machine. The patient exits the machine 410 after the image is taken, as shown in FIG. 4B.

FIG. 4B illustrates a schematic front view 450 of the medical operation system 400 taken in the transverse plane for defining the sagittal angle 370 of the vertebra 205. The front view axis 460 (and correspondingly, the side view axis 470) of the pilot hole should be precisely defined for the drilling guide 455. In some embodiments, the apparatus 300 may be attached to the drilling guide 455 with the attachment support/mechanism 308. Defining and verifying the sagittal angle 370 may be performed at the apparatus 300, as explained in connection with the method illustrated in FIG. 5B.

Figure 5A:
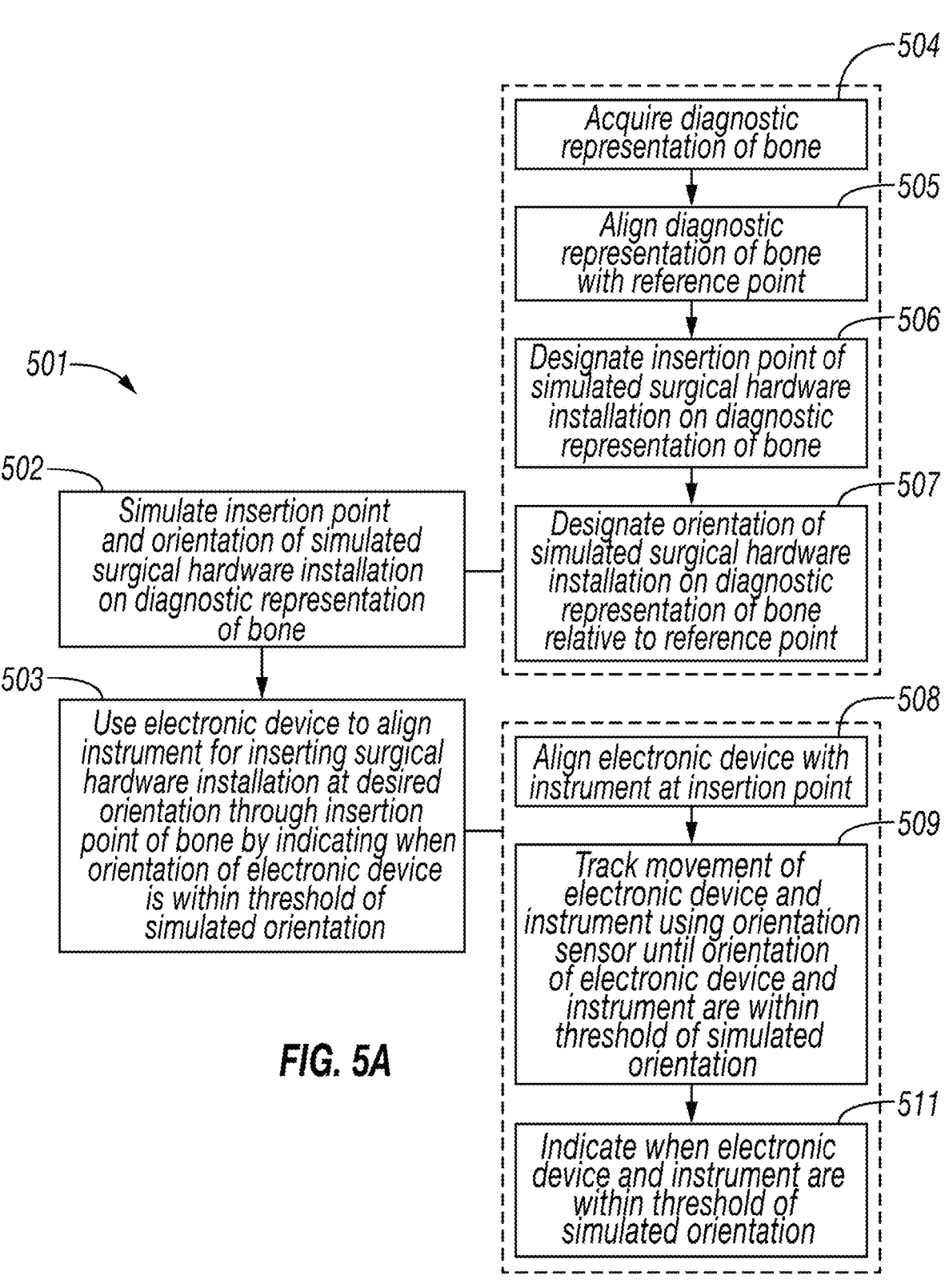
FIG. 5A illustrates an example flowchart for a method of determining an orientation of an instrument for inserting a medical device in a bone, in accordance with one or more embodiments of the present disclosure.

First, however, an example method of determining an orientation of an instrument for inserting a medical device in a bone is now described with reference to the flowchart 501 of FIG. 5A. A diagnostic image is obtained at the apparatus 300 and displayed. An insertion point and a desired orientation of a simulated surgical hardware installation are simulated and displayed on a diagnostic representation of a bone at block 502 and the desired alignment orientation is stored. Proceeding to block 503, the apparatus or medical alignment device 300 with orientation sensor, such as gyroscope 332, is used to align a tool, such as a medical tool, drill or the like for inserting or installing the surgical hardware at the desired alignment orientation from block 502 and through the insertion point of the bone by indicating when an orientation of the medical alignment device 300 is within a threshold of the simulated orientation with the desired alignment angle.

Simulating the insertion point and the orientation of the simulated surgical hardware installation on the diagnostic representation of the bone includes acquiring the diagnostic representation of the bone at block 504, aligning the diagnostic representation of the bone with a reference point at block 505, designating the insertion point of the simulated surgical hardware installation on the diagnostic representation of the bone at block 506, and designating the orientation of the simulated surgical hardware installation on the diagnostic representation of the bone relative to the reference point at block 507.

If block 502 is repeated using a second diagnostic representation of the bone that is orthogonal to the first diagnostic representation, the same steps 504 through 507 may be repeated on the second diagnostic representation with the location of the simulated surgical hardware constrained to the selections or settings made when the insertion point and orientation were selected in the first diagnostic representation. Once this is done, a three-dimensional alignment angle may be calculated or determined. This may be done by the apparatus or medical alignment device 300.

Using the electronic device, which may be the apparatus or medical alignment device 300, to align the instrument or tool for inserting the surgical hardware installation at the desired orientation through the insertion point includes aligning the electronic device with the instrument or tool at the insertion point in block 508, tracking movement or orientation of the electronic device and the instrument or tool using an orientation sensor, such as gyroscope 332, of the electronic device until the orientation of the electronic device and the instrument are within the threshold of the simulated orientation at block 509, and indicating when the electronic device and the instrument are within the threshold of the simulated orientation at block 511. The indication may be visual, auditory, or tactile. The orientation of the electronic device, and hence the alignment of the instrument or tool, may be a two-dimensional alignment angle, in certain implementations, or a three-dimensional alignment angle. FIG. 7 illustrates an example application of the alignment of block 508.

FIGS. 5B, 5C, and 5D illustrate example flowcharts for methods for indicating or determining a desired alignment angle, which also may be referred to as an insertion angle, in the: (i) sagittal plane, which may be referred to as the sagittal angle, (ii) the transverse plane, which may be referred to as the transverse angle, and (iii) the coronal plane, which may be referred to as the coronal angle, respectively, in accordance with one or more embodiments of the present disclosure. Each of these methods may be thought of as generating or determining a two-dimensional alignment angle in their respective plane.

FIG. 5B illustrates an example flowchart 500 of a method for indicating the sagittal angle 370. The method of the flowchart 500 is for verifying any insertion angle 370 of the pilot hole 220 in the sagittal plane 110 for receiving a pedicle screw 210 in the vertebra 205. At 510, the axis 305 of the apparatus 300 is aligned or is oriented with the sagittal plane of an image of the vertebra, in this embodiment. In some embodiments, a user may hold the apparatus 300 and rotate the apparatus 300 to match a marking indicating the axis 305 with features of the vertebra 205 that indicate the sagittal plane. In some embodiments, the marking may be displayed on the screen as the user aligns the device. In other embodiments, the image of the vertebra (or other desired object or bone) is a diagnostic image that is displayed on the apparatus 300, which may be a medical alignment device 300, and is already oriented in some manner to the sagittal plane.

At 520, the image of the cross-sectional view is captured in the transverse plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent or transmitted to the apparatus 300 via a wired or wireless connection to be displayed on the apparatus 300 such that no physical representation (e.g., films, photos, monitors) may be needed for this step.

At 530, definitions of the insertion sagittal angle 370 of the pilot hole 220 and the initial position 375, also referred to as the insertion location, of the pilot hole 220 are provided or specified by a user. This input operation may be performed using various input devices of the apparatus 300, including a computer mouse, a keyboard, a touchscreen, or the like. In one embodiment, a multi-touch screen (e.g., the display 360) is used for both displaying the image and receiving the definition input from a user. Example illustrations of this input are provided in FIGS. 6A-6D, where the insertion location or initial position 375 of the pilot hole 220 for the installation of a pedicle screw are established by locating (or simulating) graphically the insertion location on the displayed diagnostic image, and the applicable alignment angle for the displayed plane may defined by moving or locating (or simulating) the desired position of the alignment angle of the pilot hole/pedicle screw.

At 540, an angle-indicative line is generated by a processor and displayed on the display 360 along with the diagnostic image. The angle-indicative line can rotate in response to the apparatus 300 rotation and provides a notification when the orientation or position of the apparatus 300 approximately forms the insertion sagittal angle 370 between the apparatus 300 longitudinal axis 305 and the sagittal plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of apparatus 300 to generate the current orientation of the apparatus 300. This current orientation may be compared to the desired insertion angle (or alignment angle) discussed above in connection with 530 to determine whether or not alignment exists or the extent of alignment, and this may be compared or shown graphically.

The indicative line may generate notations in various forms, including a visual alert such as highlighting the angle-indicative line, an audio alert such as providing a continuous sound with variable frequency indicative of the proximity between the current angle and the desired angle, and a small vibration that allows the user to notice the angular change. It should be appreciated that any audio alert may be used, such as a single sound or series of sounds when the desired angle is reached. Likewise, a single vibration or a series of vibrations may be emitted when the desired angle is reached. In some implementations, the flowchart 500 illustrated in FIG. 5B may be applicable for generating indication angles in the transverse plane or the coronal plane for indicating a respective transverse angle or a coronal angle.

FIG. 5C illustrates a flowchart 550 of an implementation for indicating a transverse angle, which is an angle with respect to the transverse plane of the vertebra. The method of the flowchart 550 is for verifying any pedicle screw insertion angle in the transverse plane of the vertebra 205. At 560, the axis 305 of the apparatus 300 is aligned with the transverse plane. In some embodiments, a user may hold the apparatus 300 and rotate the apparatus 300 to match a marking indicating the axis 305 with features of the vertebra 205 that indicate the transverse plane. In some embodiments, the marking may be displayed on the screen as the user aligns the device.

At 570, an image of the posterior view is captured or provided in the coronal plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 580, definitions of the insertion angle in the transverse plane 130, and the initial position 375 of the pilot hole are provided by a user, as similar to the sagittal angle defined at 530.

At 590, an angle-indicative line for the corresponding transverse angle is generated by a processor and displayed on the display 360. The angle-indicative line can rotate in response to the apparatus 300 rotation and provides a notification when the apparatus 300 approximately forms the insertion transverse angle, as defined in step 580, between the apparatus 300 longitudinal axis 305 and the transverse plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of the apparatus.

FIG. 5D illustrates a flowchart 555 of another implementation for indicating a coronal angle. The method of the flowchart 555 is for verifying any insertion angle of a pedicle screw 210 in the vertebra 205 in the coronal plane 120. At 565, the axis 305 of the apparatus 300 is aligned with the coronal plane. In some embodiments, a user may hold the apparatus 300 and rotate the apparatus 300 to match a marking indicating the axis 305 with features of the vertebra 205 that indicate the coronal plane. In some embodiments, the marking may be displayed on the screen as the user aligns the device.

At 575, the image of the lateral view is captured in the sagittal plane. In one embodiment, the apparatus 300 includes a smart phone, a tablet computer, a laptop computer, or any portable computational device including those that include a camera for capturing a representation of the posterior view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 585, respective definitions of the insertion angle in the coronal plane 120, and the initial position 375 of the pilot hole are provided by a user, as similar to the sagittal angle defined at 530.

At 595, an angle-indicative line for one of the corresponding coronal angle is generated by a processor and displayed on the display 360. The angle-indicative line can rotate in response to the apparatus 300 orientation and provides a notification when the apparatus 300 approximately forms the insertion coronal angle between the apparatus 300 longitudinal axis 305 and the coronal plane. In some implementations, the angle-indicative line is a rotating line generated in the display 360 that allows a user to monitor the change of orientation of the apparatus 300. The orientation monitoring is performed with an orientation apparatus 330 of the apparatus 300. More specifically, in some embodiments, a gyroscope 332 that includes at least one axis of rotation may provide the function of monitoring the apparatus's orientation or position.

Figure 6A:
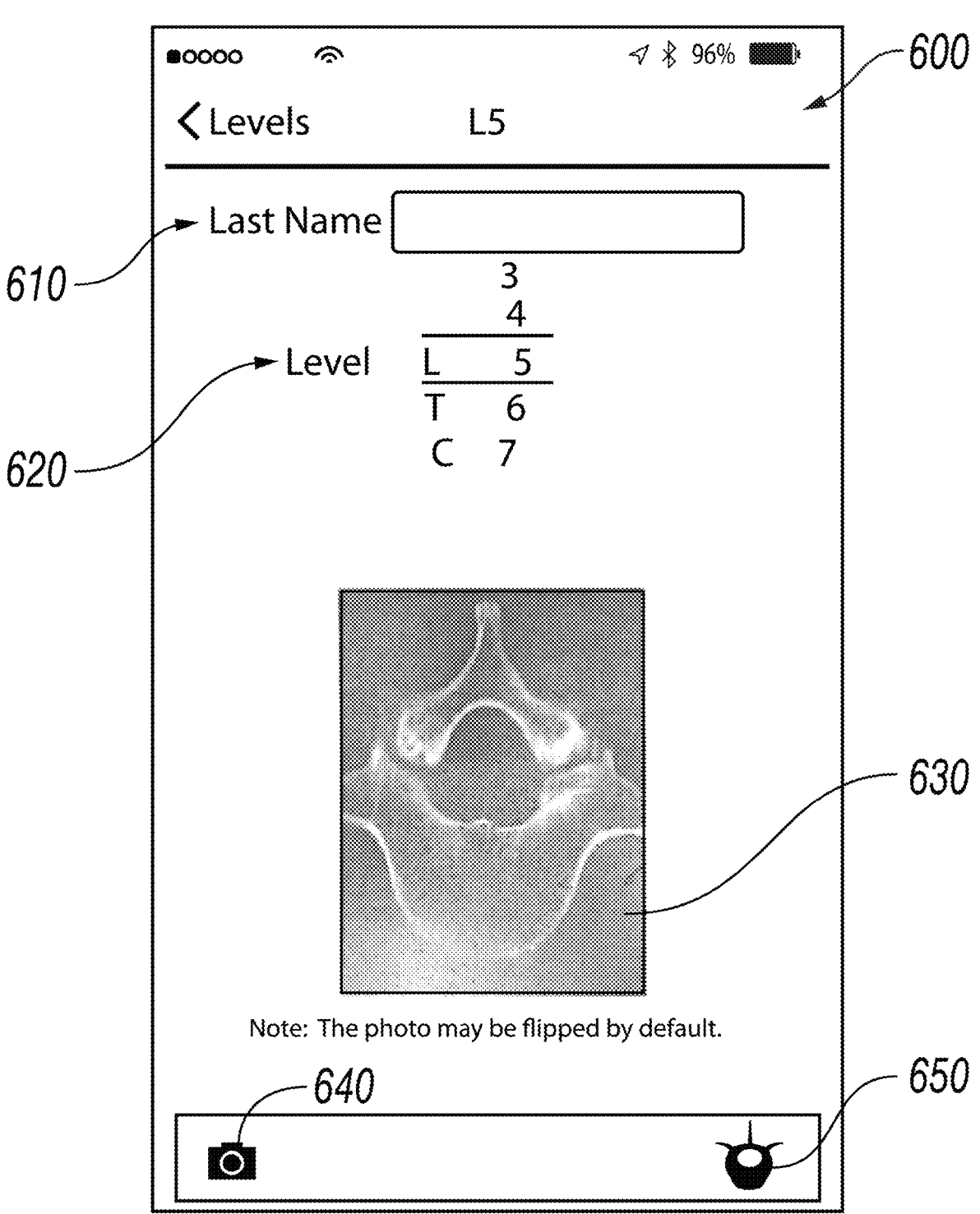
Figure 6B:
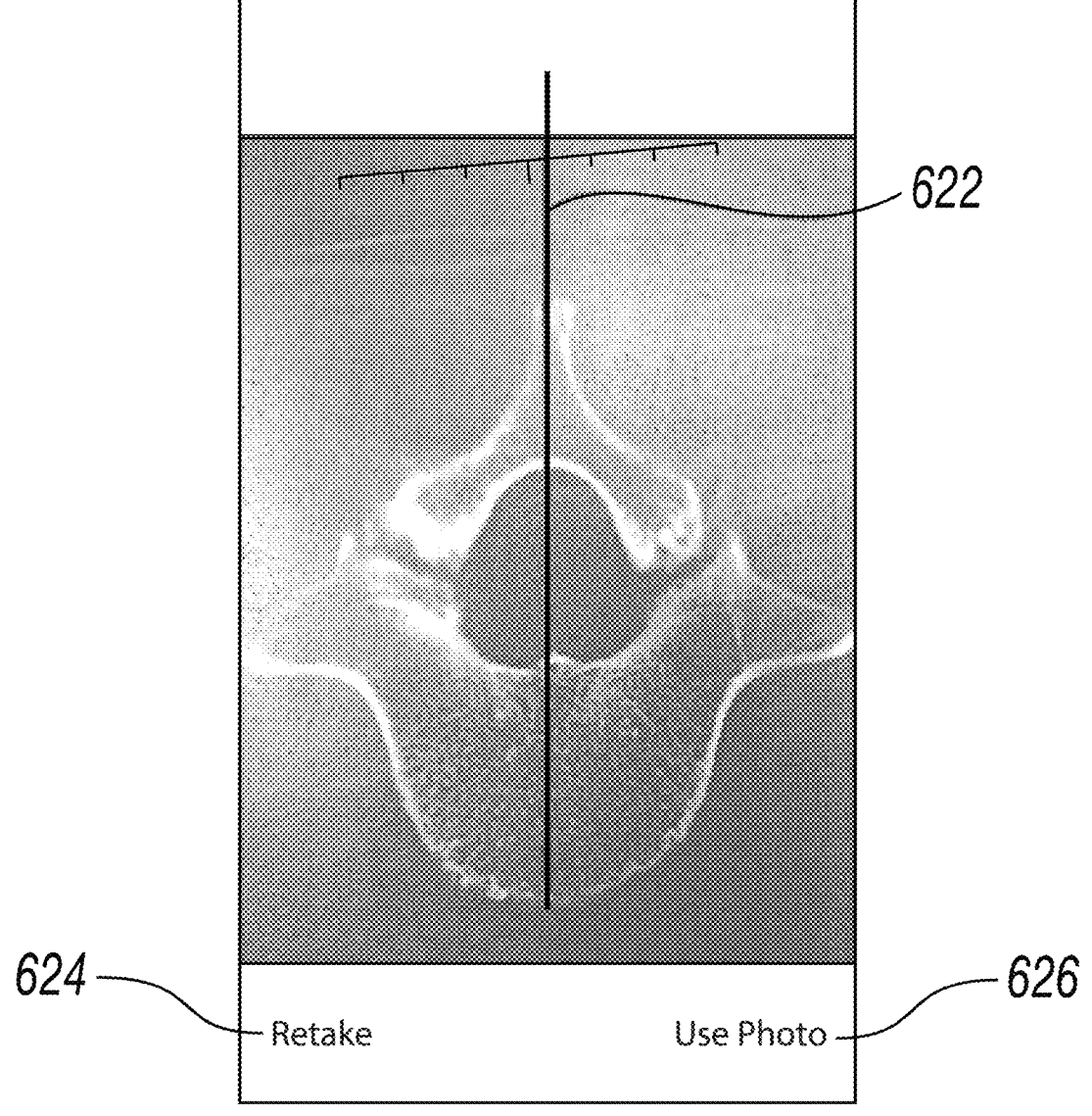
Figure 6C:
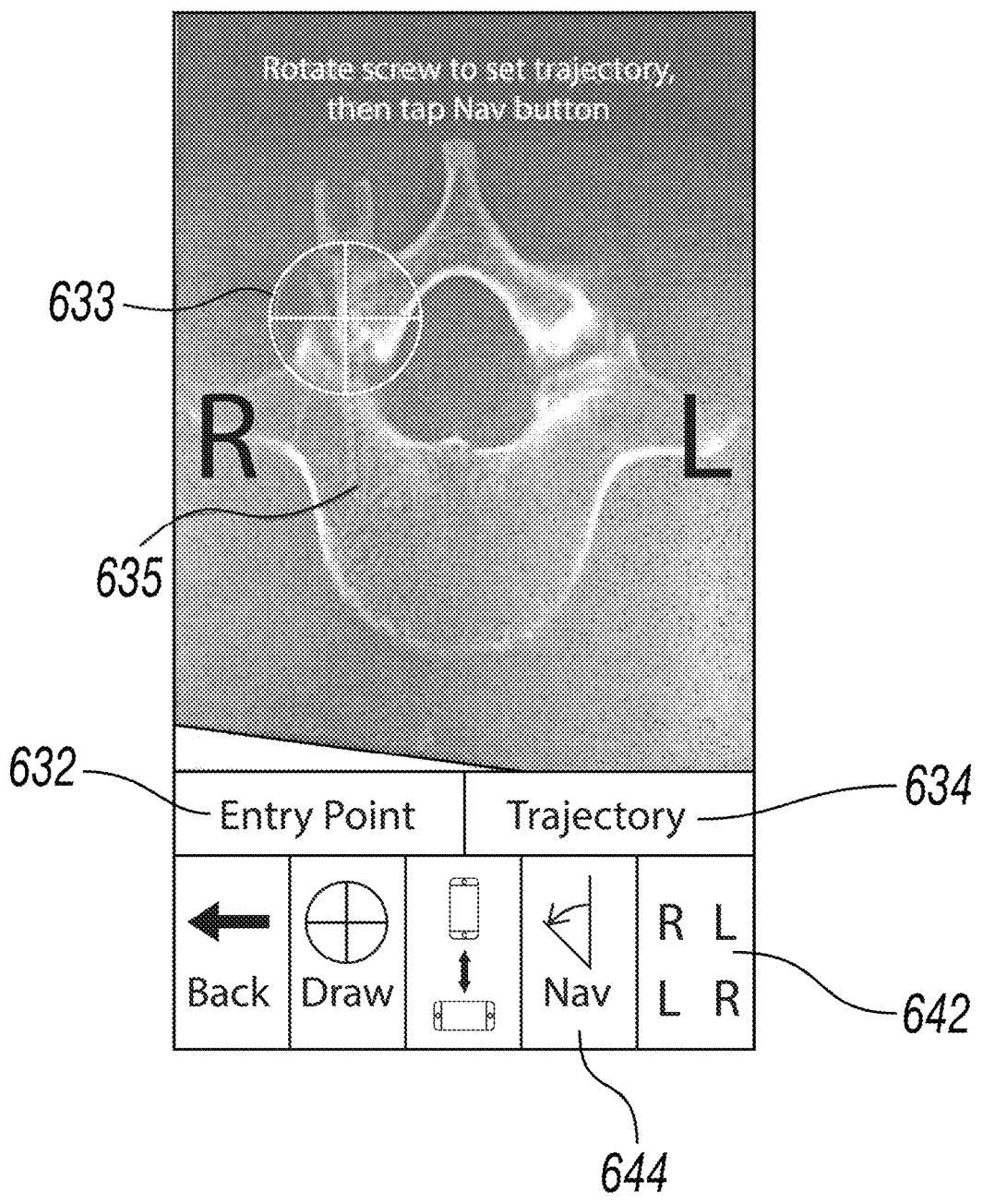
Figure 6D:
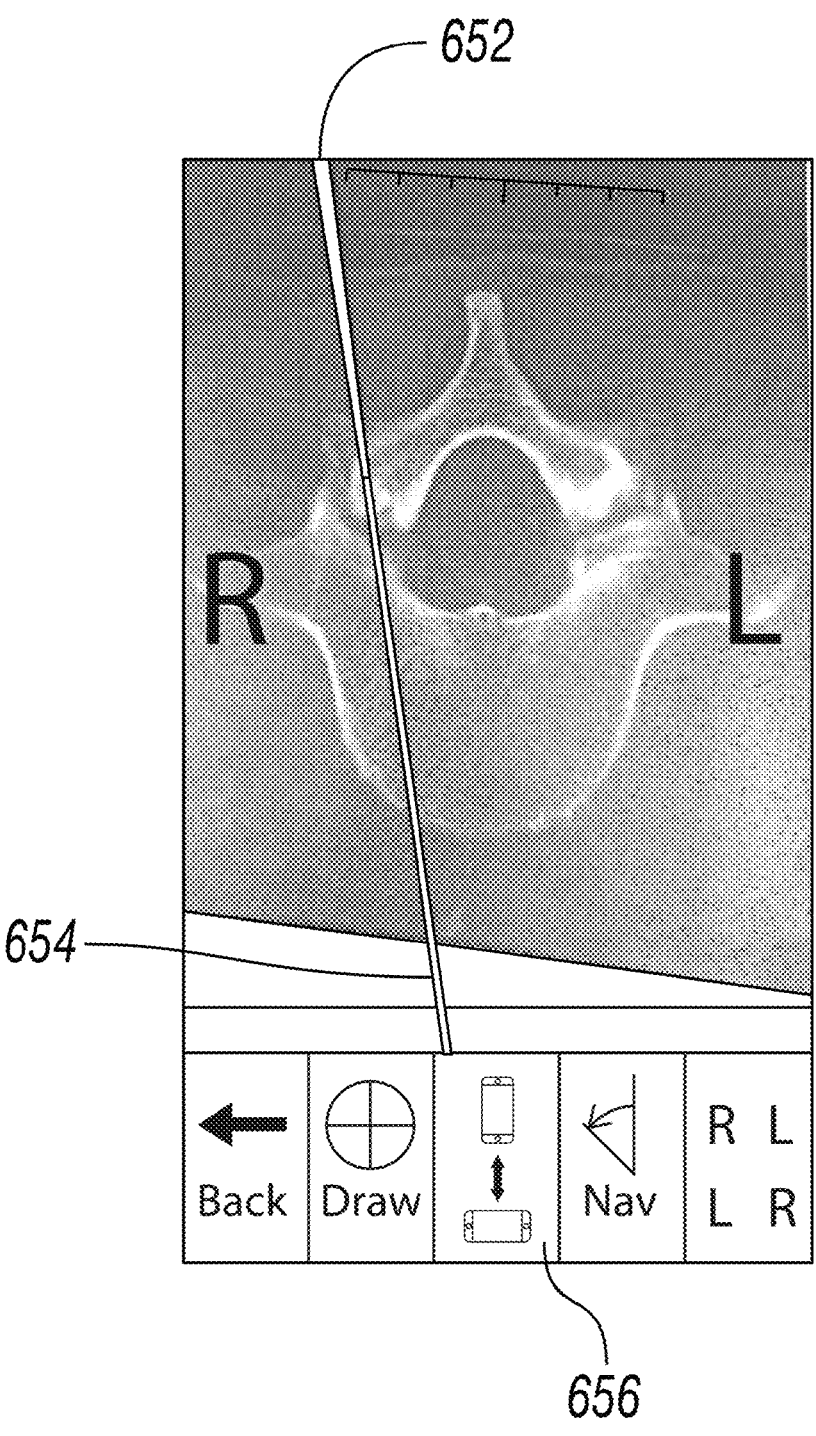

FIGS. 6A-6D illustrate examples of user interfaces for controlling a computer implemented program to perform the methods shown in FIG. 5A-5D. FIG. 6A illustrates an interface 600 for selecting vertebra of a patient, FIG. 6B illustrates displaying a diagnostic image and aligning (or confirming the alignment) the axis 305 of the apparatus 300 with the sagittal plane of the image, FIG. 6C illustrates defining a pedicle screw's position, including its insertion location or entry point at the cross hair, and its sagittal angle 370 on the diagnostic image, and FIG. 6D illustrates generating an angle-indicative line 652 for showing the angle between the longitudinal axis of the apparatus and the sagittal plane. In some embodiments, the angle-indicative line may represent a virtual gear shift pedicle probe, or other instrument for aligning a pedicle screw or pilot hole. When the virtual gear shift or angle is properly aligned, the virtual gear shift may change colors, or may change length or width. The angle-indicative line can rotate or reorient in response to the apparatus 300 rotation or reorientation, and provides a notification when the apparatus 300 approximately forms the desired alignment angle in this view between the apparatus 300 longitudinal axis 305 and the desired alignment angle.

In FIG. 6A, the patient's profile may be selected or added by typing the last name of the patient in the window 610.

The corresponding vertebra for the desired angle is selected in the window 620. The camera button 640 allows a user to take a picture of a diagnostic image of the actual vertebra or to receive such a diagnostic image. The diagnostic image or picture is shown in the window 630. The button 650 allows the user to move onto the next step. As previously discussed, the picture at the vertebra may be provided without use of the camera or camera button 640.

For example, by using a camera of a mobile device, a user can take a picture of an axial view (either CT or MRI) in the transverse plane 130, of the desired vertebral body 205. Use the line 622 to line up the vertebral body so that it is proximately vertical for aligning with the sagittal plane (or other desired plane), as shown in FIG. 6B. A retake button 624 allows the user to go back to the previous steps to retake the image to ensure the alignment is proper. The button 626 allows the user to select the current photo to be used in the following operations.

After selecting button 626, the user may be returned to the detail view as shown in FIG. 6C. The photo may, in some embodiments, be automatically flipped to approximate its position during surgery. Button 642 may be selected to flip the orientation of the photo. For example, the RL button 642 can be used to flip the picture (and pedicle screw) depending on whether the surgeon is placing the screw while looking towards the patient's head (e.g., in the longitudinal axis toward the cephalad direction) or towards their feet (e.g., in the longitudinal axis toward the caudal or caudad direction).

The user next selects the optimal pedicle screw position by selecting the navigation button 644 to move the simulated pedicle screw to a desired location by moving the crosshairs 633 to the cortical entry point of the screw, for example, by tapping the entry point button 632 to confirm, and then tapping the trajectory button 634 and rotate the screw to its desired position 635. The crosshairs 633 specify the insertion location, such as the initial position 375 of FIG. 3B.

Tap the Nav button 644 and a virtual gear shift probe 652 (which may represent any tool or axis, such as a drill or pilot hole longitudinal axis) appears on the screen. The gear shift probe's orientation matches the orientation of the apparatus 300, which will include orientation circuitry, such as a gyroscope to determine the orientation of apparatus 300. In some embodiments, once the angle of the gear shift probe 652 is about 20 degrees within the selected trajectory, the gear shift probe 652 will turn yellow, at 5 degrees, it will turn green, and when the alignment is within 1 degree of the target angle, a green line 654 will extend outward and the pedicle screw will disappear to signify that the apparatus 300 is properly aligned.

In some embodiments, the device or apparatus 300 can be placed in a sterile bag and then be placed against the gear shift probe as it is being used to create the path for the pedicle screw. As provided herein, the apparatus 300 may be positioned in an attachment apparatus, such as those shown in FIGS. 19-24, so that the apparatus 300 may be conveniently aligned or abutted with a tool, such as the gear shift probe, drill, and the like.

Some gear shift probes may be too short to allow the device (apparatus 300) to be placed against them lengthwise. If this is the case, tap the 90 degree button 656 and the screen will be rotated so the short edge of the device can be placed against the gear shift probe.

Other implementations of the disclosed system and method are possible. For example, the apparatus 300 may also use a second or more views to define various angles not limited within the sagittal plane. For example, and in accordance with the foregoing disclosure, images of the vertebra may be captured from two orthogonal planes, such as through superior, lateral, posterior, anterior views, and various combinations thereof, to provide multiple reference points so that three-dimensional representations of the alignment angles can be presented.

In addition, different mobile computer devices may be used or modified into the apparatus 300 by equipping corresponding image acquisition units, input terminals, and motion or orientation sensing units. In some embodiments, the apparatus 300 includes a smart phone or another electronic device having a gyroscope. In addition, other motion or orientation sensors may be included such as the inertial measurement unit 334, and the accelerometers 336. The apparatus 300 may also be attached onto various medical devices or equipment for guiding insertion angles that require high precision and ease of use. The smartphone may be an iPhone for example. Also, in some application, the mobile computer device may be an iPod™ Touch, iPad™, Android phone, Android tablet, Windows Phone, Windows tablet, or Blackberry phone. Also, in some applications, the mobile computer device may be an Apple TV in combination with an Apple TV remote, or a Nintendo Wii in combination with a Nintendo Wii remote. Indeed, the mobile computer device may be any combination of electronic devices where the orientation sensor (such as a gyroscope) is in one electronic device and the processor is in another electronic device.

In some embodiments, axis other than the device's longitudinal axis may be used. Axes can be defined by a portion of the device (e.g., an edge or surface of the device). More than one orientation apparatus 330 may be used at the same time, if desired. Surgical apparatus may include pedicle screws, gear shift probes, and other medical devices.

It should be appreciated that the various methods and techniques described above may be utilized with a virtual reality or augmented reality device, either on its own or in conjunction with another electronic device such as a smartphone or computer. The determination of the insertion point or pilot hole and the proper angle for the surgical tool used to attach or install the pedicle screw or other medical device may proceed in any of the fashions as described above, and then the virtual reality or augmented reality device may be used to display the proper insertion point or pilot hole and proper angle for the surgical tool to a physician.

In the case of a virtual reality device, the simulation of a tool or axis at a desired three-dimensional alignment angle or other alignment angle may be displayed to the surgeon or user in an immersive three-dimensional fashion so that the surgeon can view the bone or tools used in a procedure as it will appear during a surgery. In addition, the planning of the insertion point or pilot hole and the proper angle for the surgical tool may be conducted with the aid of the virtual reality device.

In the case of an augmented reality device, during the actual surgery, virtual visual indicia may be displayed superimposed over the real bone, illustrating to the physician precisely where to insert the surgical tool and at precisely which angle the surgical tool should be inserted and operated.

An augmented reality or virtual reality based system 700 for use in assisting of the determination of the proper insertion point and proper angle for a surgical tool to be used to install a pedicle screw is now described with reference to FIG. 8. The system 700 includes an electronic computing device 702, such as a smartphone, tablet, desktop based personal computer, or laptop based personal computer. A virtual reality based or augmented reality based device 704, such as a wearable headset, wearable goggles, three dimensional projector, or holoprojector, may be capable of wired or wireless communication with the electronic computing device 702.

Figure 9:
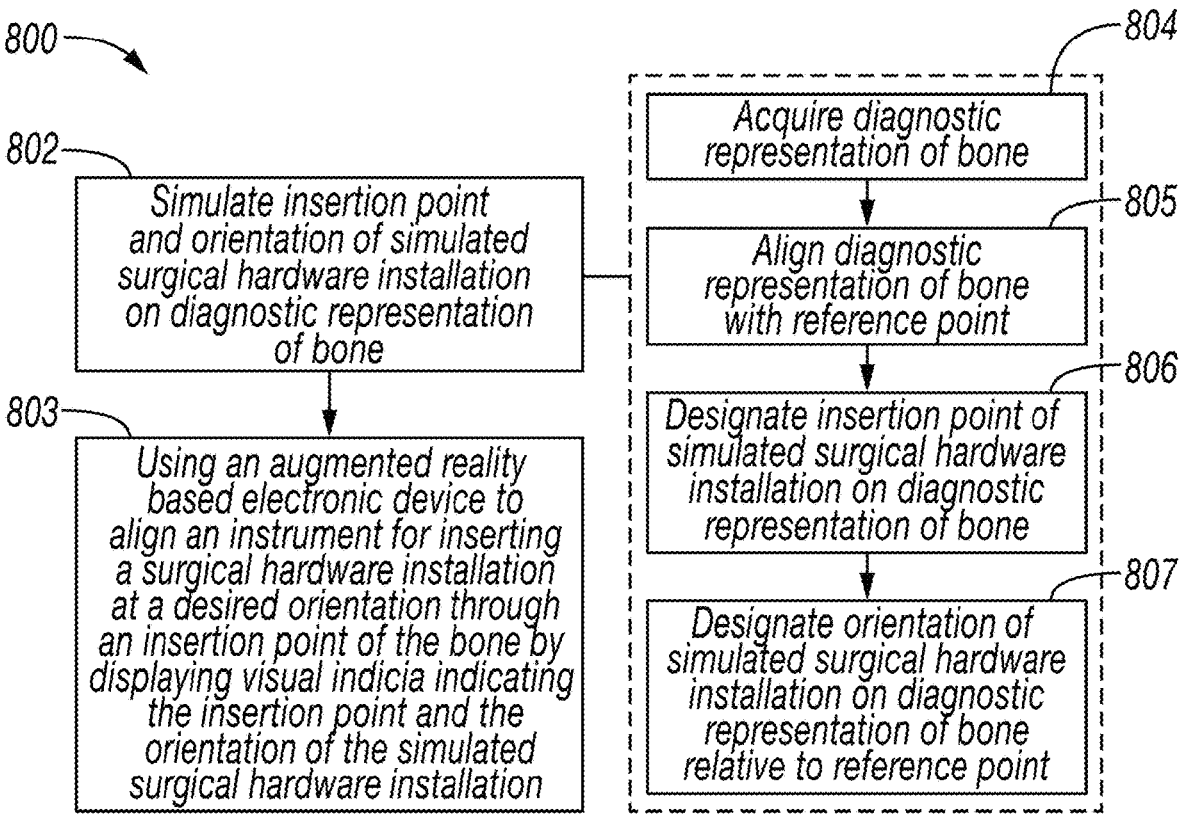
FIG. 9 illustrates an example flowchart for a method of determining and displaying an orientation of an instrument for inserting a medical device in a bone, using an augmented reality device, in accordance with one or more embodiments of the present disclosure.

Operation of the system 700 is now described with reference to the flowchart 800 shown in FIG. 9. Operation begins with the electronic computing device 702 simulating an insertion point and orientation of a surgical hardware installation on a diagnostic representation of the bone onto which it is to be installed (Block 802). This operation can proceed in any of the ways described above, although it should be understood that the virtual reality based or augmented reality based device 704 may be used as a display during this process. It should further be appreciated that the virtual reality or augmented reality based device 704 may have a camera associated therewith used to image the real world and provide it to the user when operating in an augmented reality mode (Block 803).

One way to proceed with this simulation begins with acquiring a diagnostic representation of the bone (Block 804). This may be performed using an image capturing device associated with the electronic computing device 702, such as a two dimensional or three dimensional camera, or this may be performed using a standalone image capturing device and then receiving the image data from that device at the electronic computing device 702. Still further, this may be performed using a medical imaging device, such as a CT scan or MM scan, and then receiving that image data at the electronic computing device 702, which may serve as apparatus 300.

Thereafter, the diagnostic representation of the bone is aligned with a suitable reference point (Block 805). Then, an insertion point of for a simulated surgical hardware installation is designated on the diagnostic representation of bone (Block 806). Next, an orientation of the simulated surgical hardware installation on the diagnostic representation of bone relative to reference point is determined (Block 807). This orientation is determined in three dimensions, and can be referenced to suitable planes of the body as defined by typical medical terminology and known to those of skill in the art.

Figure 10:
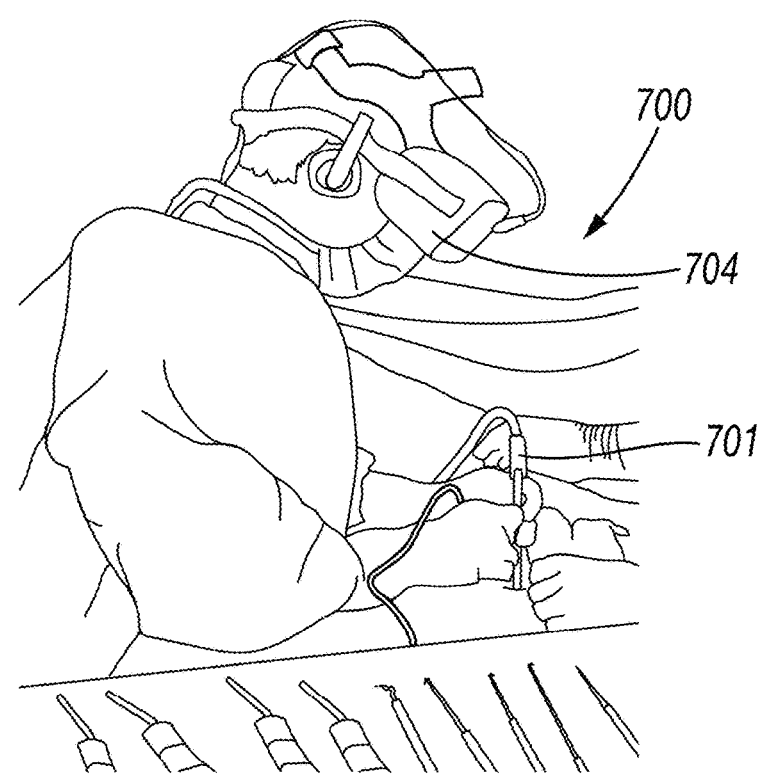
FIG. 10 illustrates the system of FIG. 8 in use to assist with inserting a medical device in a bone.
Figure 11:
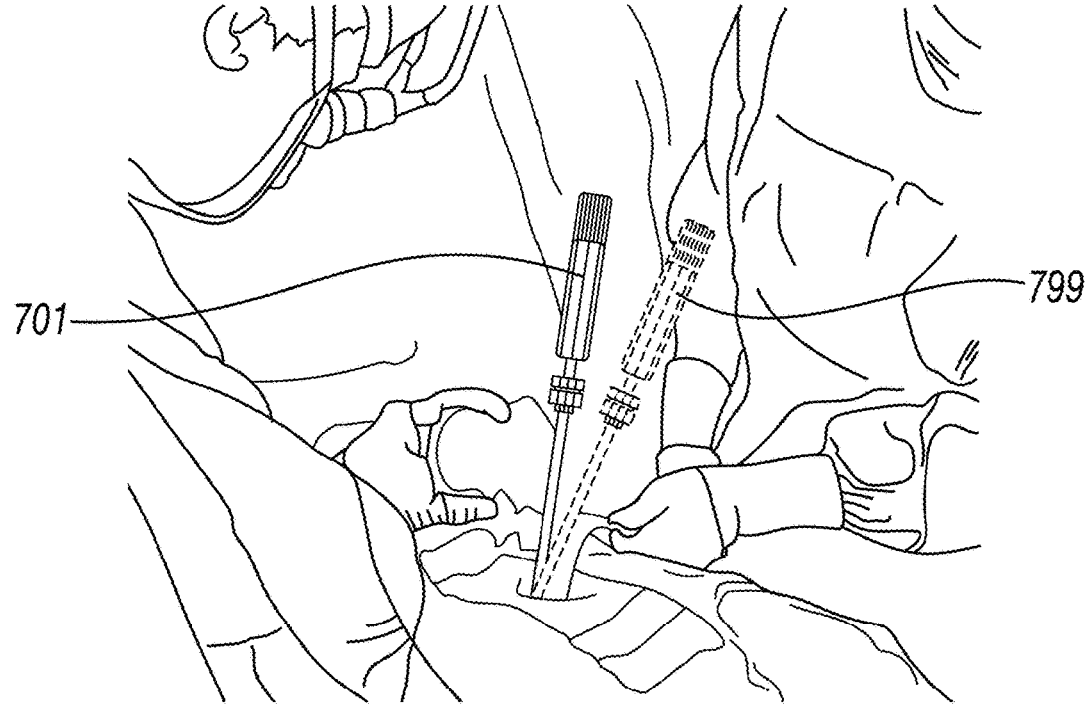
FIG. 11 illustrates an augmented reality display presented by the system of FIG. 8 showing an orientation angle for an instrument for inserting a medical device in a bone.

Then, the surgery itself may be performed. During surgery, virtual reality based or augmented reality based device 704 is worn by the operating physician or surgeon, as shown in FIG. 10. Here, the virtual reality or augmented reality based electronic device 704 is used to align an instrument or tool 701 for inserting a surgical hardware installation at a desired orientation through an insertion point of the bone by displaying visual indicia indicating the insertion point and the orientation of the simulated surgical hardware installation (Block 803). This visual indicia can be shown superimposed over the bone itself, such as shown in FIG. 11 by the virtual representation of the tool 799. It should be appreciated that the visual indicia need not be a virtual representation of the tool 799 as shown, and may instead be an arrow, a line, or any other suitable visual representation.

In some instances, cameras, position detectors, or other devices situated about the surgery site may be used to gather real time information about the actual position of the tool 701, so that feedback may be presented to the surgeon. For example, the visual indicia may change when the tool 701 is properly aligned, or may inform the surgeon that the tool 701 is not properly aligned. Likewise, additional visual indicia may be displayed when the tool 701 is properly aligned, or when the tool 701 is not properly aligned. Similarly, an audible response may be played by the virtual reality based or augmented reality based device 704 either when the tool

701 is properly aligned, or when the tool 701 is not properly aligned, or to guide the surgeon in moving the tool 701 into the proper position. In some cases, a position detector may be associated with or collocated with the tool 701, and the position detector such as an accelerometer may be used in determining whether the tool 701 is properly aligned, or when the tool 701 is not properly aligned.

In some instances, based on the above feedback, if the patient moved or the bone is moved, the visual indicia 799 is moved along with the bone by the virtual reality based or augmented reality based device 704 so that proper alignment is maintained during the surgery.

Figure 8:
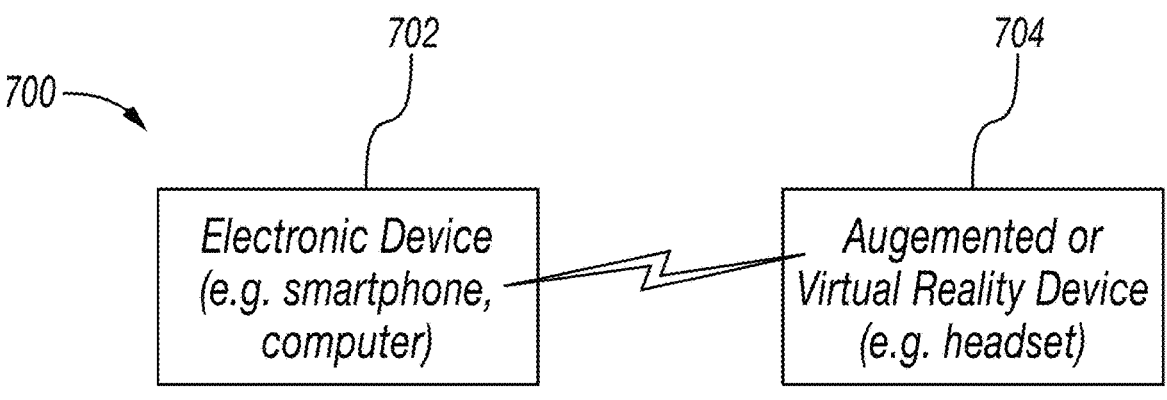
FIG. 8 presents a schematic diagram of a system used in accordance with an embodiment to define and verify an insertion angle for a pilot hole in a vertebra.
Figure 12:
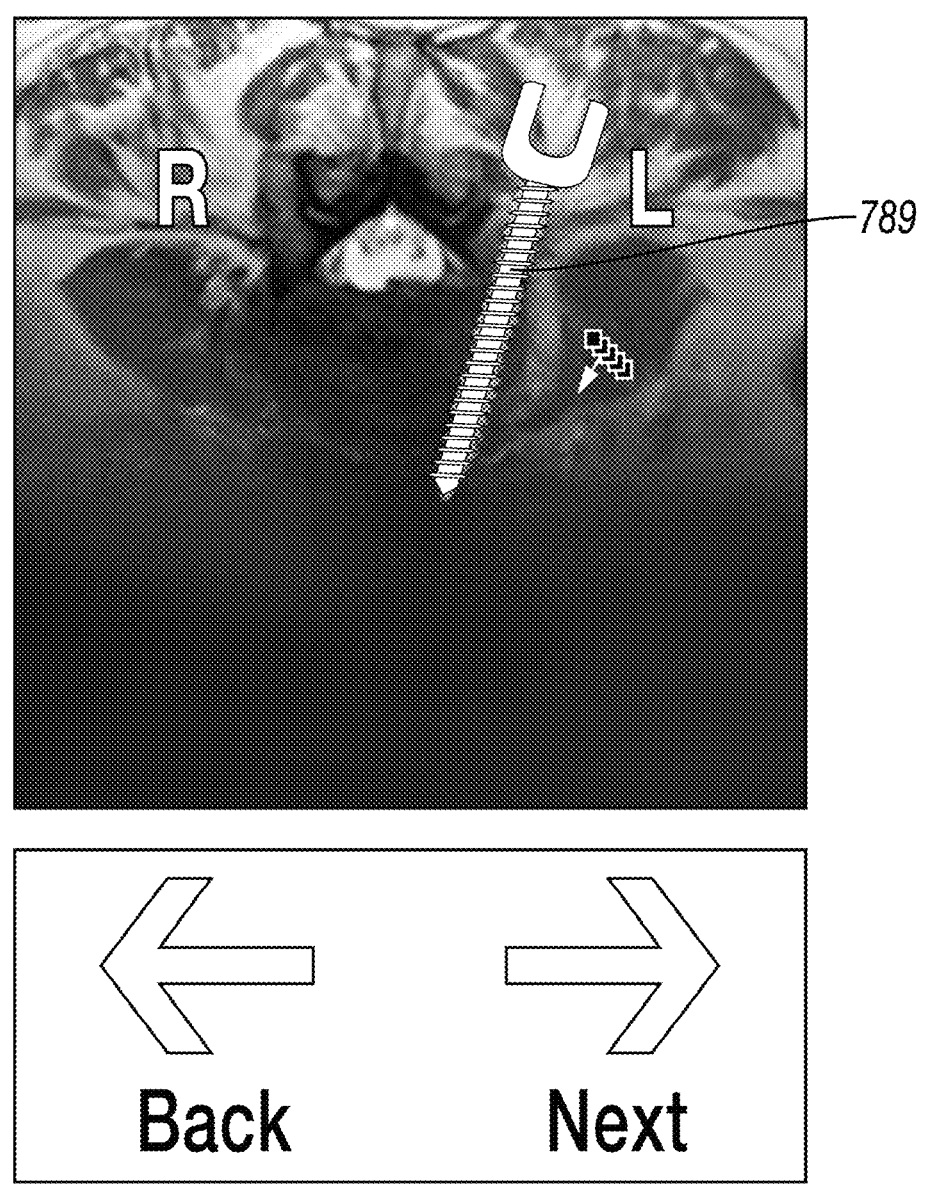
FIG. 12 illustrates a virtual representation presented by the system, such as the medical alignment device or electronic device of FIG. 8, showing an axial view of a vertebra with a proposed alignment position of a pedicle screw shown that includes an insertion point and alignment angle for insertion or installation of the medical device into the bone or vertebra in this plane.

FIG. 12 illustrates a virtual representation presented by the system, such as the medical alignment device or electronic device of FIG. 8, showing a diagnostic image of a vertebra in an axial view with a simulated pedicle screw 789 shown that can be manipulated and moved to set a desired insertion point or location, and a desired alignment angle. Once set, an insertion location and alignment angle are stored, such as by a medical alignment device 300, for this two-dimensional view of the vertebra or object in this plane.

Figures 13A, 13B:
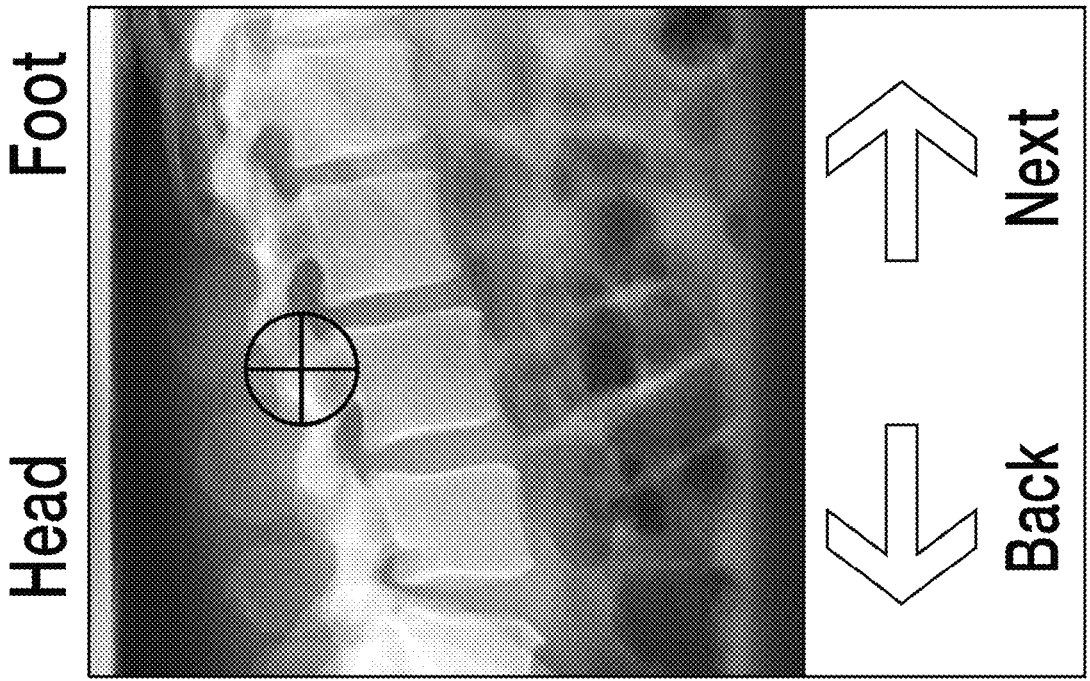
FIGS. 13A and 13B illustrate a virtual representation showing an orthogonal, lateral view of the vertebra and pedicle screw as set in the plane of FIG. 12, with the user able to establish the insertion location and alignment angle of the pedicle screw to be set in this plane so that the system, such as a medical alignment device, now has enough information as to the location of the pedicle screw in two orthogonal planes to determine a three-dimensional alignment angle for the installation of the pedicle screw in this vertebra.

FIGS. 13A and 13B illustrate a virtual representation showing an orthogonal, lateral view of the vertebra and pedicle screw as shown and as set in the plane of FIG. 12, with the user able to establish or set the insertion location and alignment angle of the simulated pedicle screw in this plane so that the system, such as a medical alignment device, now has enough information as to the location of the pedicle screw in two orthogonal planes to determine a three-dimensional alignment angle for the installation of the pedicle screw (or drilling of a pilot hole for the pedicle screw) in this vertebra. FIG. 13A illustrates the cross-hair to set the desired insertion point, while being constrained with the positioning of the pedicle screw as defined in the view of FIG. 12, and, similarly, the angle of the pedicle screw may be set as desired as shown in FIG. 13B, while also being constrained with the positioning of the pedicle screw as set in the view of FIG. 12.

The medical alignment device 300 may calculate a desired three-dimensional alignment angle based on the inputs as just described in connection with FIGS. 12 and 13. The medical alignment device 300, knowing its own orientation, may notify a user, such as a surgeon, when a side, surface, or portion of the medical alignment device 300 is oriented according to the desired three-dimensional alignment angle. Thus, the apparatus 300, which may be referred to as a medical alignment device 300 in certain implementations, may be positioned relative to a tool (such as adjacent to or abutted with) to align the tool to the desired three-dimensional alignment angle. The tool may include, for example, a drill or gear shift probe to create a pilot hole for installing a pedicle screw. The tool, of course, could be any tool to be aligned at a desired three-dimensional angle.

Figure 14:
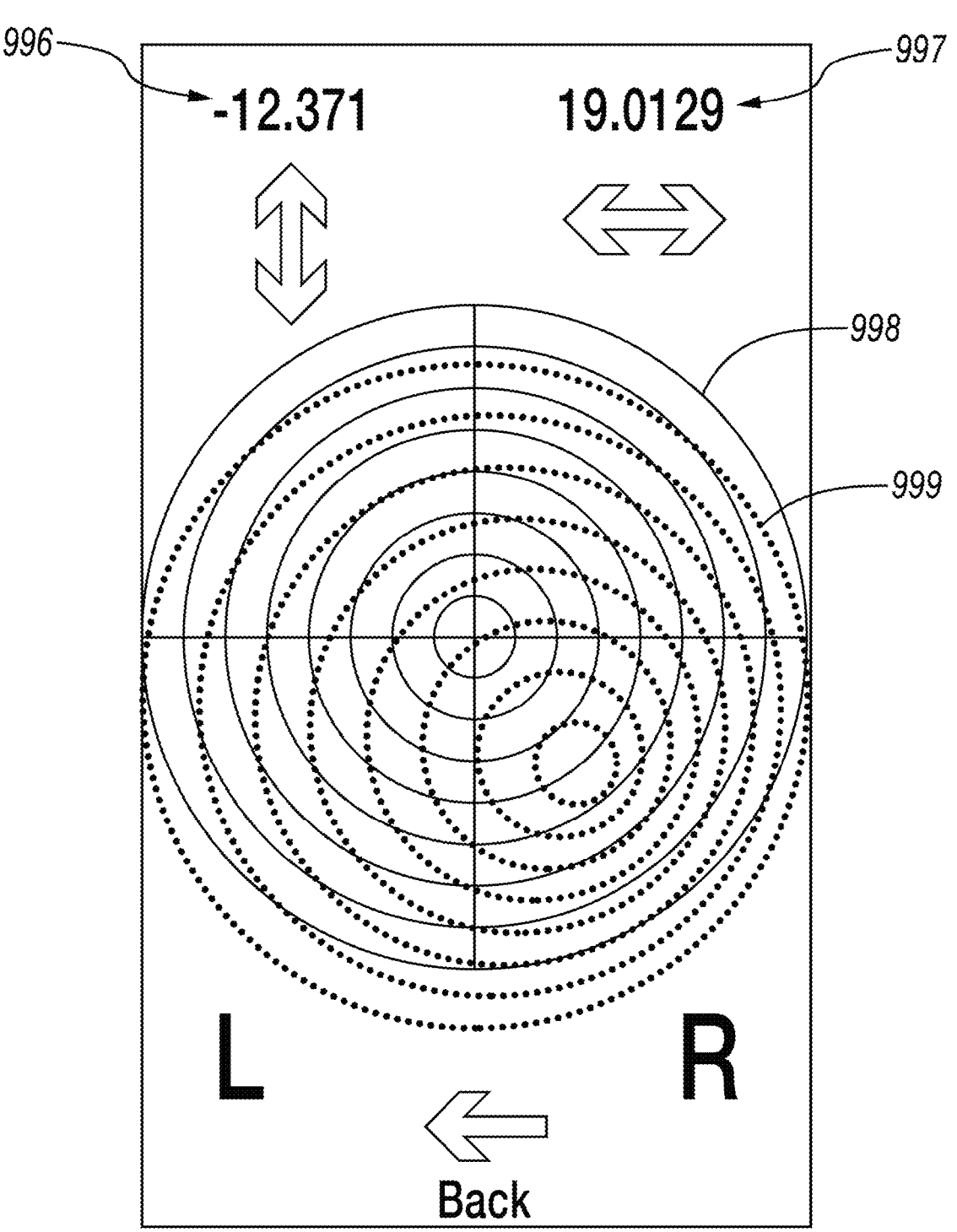
FIG. 14 illustrates an example application of the aligning method presented in FIG. 5A in which the medical device is not properly angled for insertion into the bone.
Figure 15:
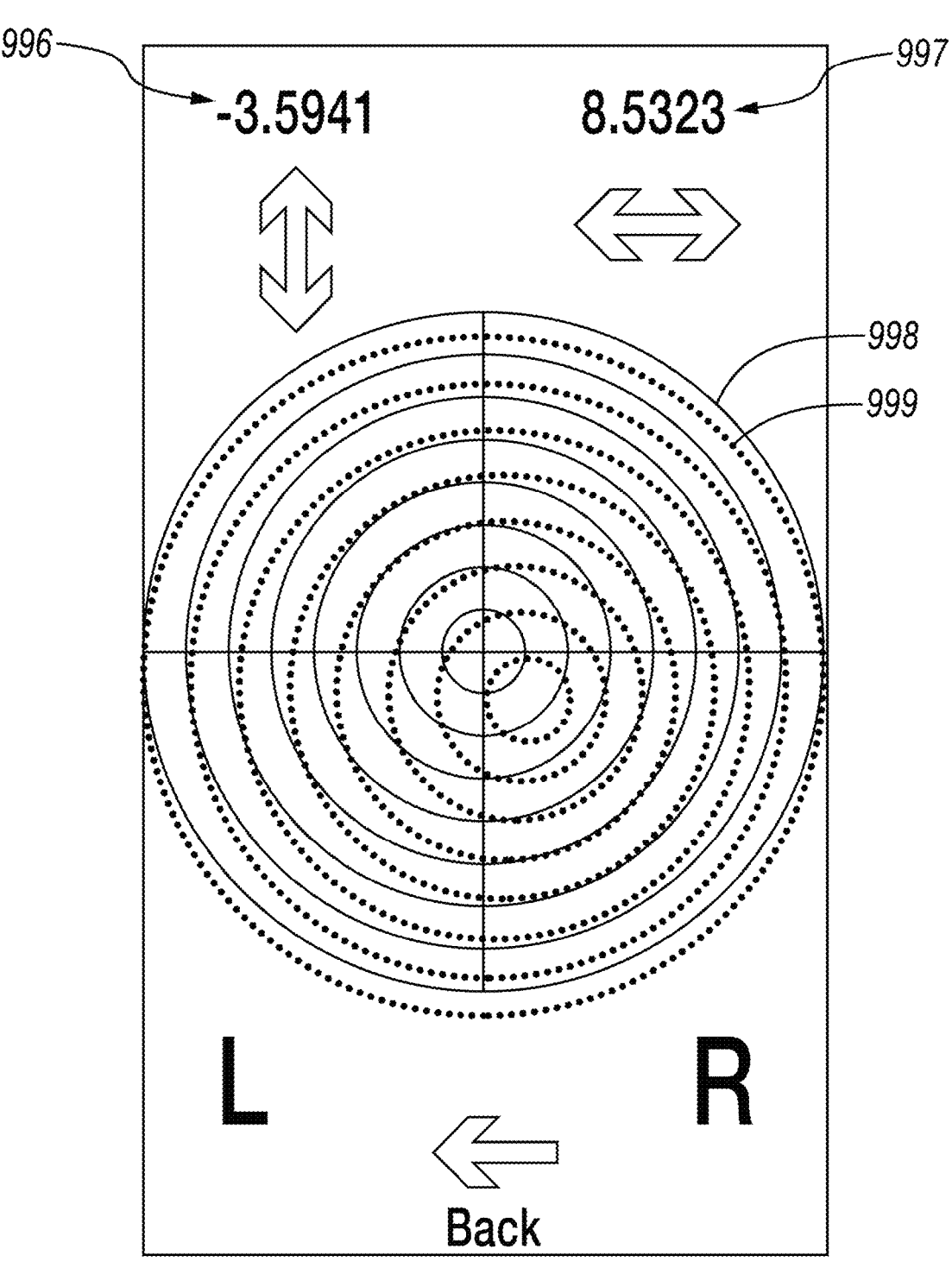
FIG. 15 illustrates an example application of the aligning method presented in FIG. 5A in which the medical device is not properly angled for insertion into the bone, yet is more properly aligned than it was in FIG. 14.
Figure 16:
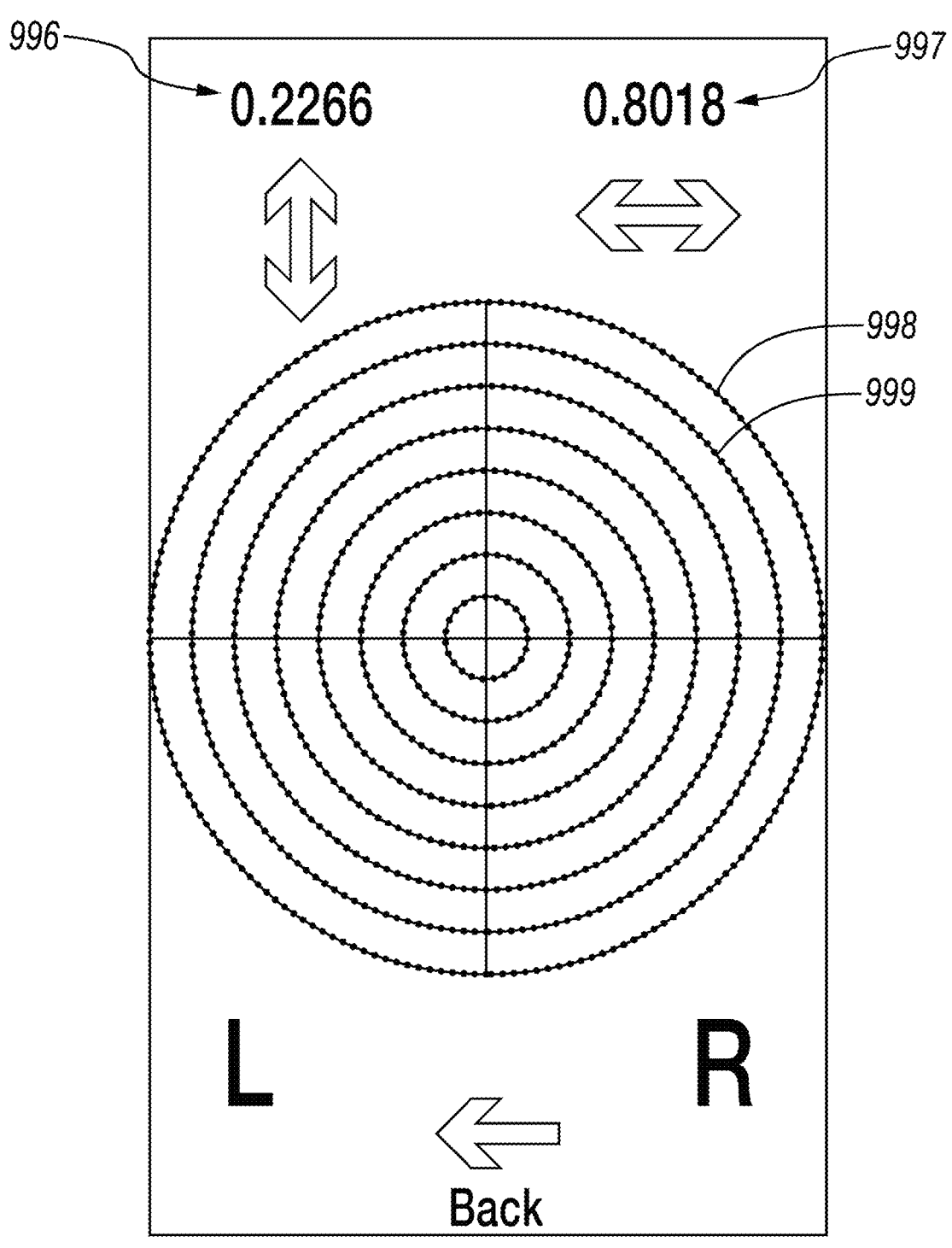
FIG. 16 illustrates an example application of the aligning method presented in FIG. 5A in which the medical device is properly angled for insertion into the bone.

FIGS. 14-16 illustrate a series of two-sets of concentric circles illustrating one embodiment of a graphical indicator or notification showing how the current position of the apparatus 300 is oriented relative to the desired alignment angle. As the orientation of the apparatus 300 is moved or aligned more closely to the desired three-dimensional alignment angle, as illustrated when looking at FIGS. 14-16 consecutively, the concentric circles are moved closer to one another providing a graphical indication or feedback to assist a user or surgeon to align the apparatus 300, and hence an attached or adjacent tool, to the desired alignment angle. Once the apparatus 300 is oriented within a desired threshold close to the three-dimensional alignment angle, an auditory, visual, and/or tactile notification may be provided to alert the user.

Numerical indicators 996 and 997 may also be provided as shown in FIGS. 14-16, along with double arrows adjacent the numerical indicators to denote alignment in each such plane. The apparatus 300 may display numerical differences (or errors) in each of the two planes of the desired alignment angles. The numerical indicators 996 and 997 show how close and in what direction the orientation of the apparatus 300 is positioned relative to the desired alignment angles in each of the two planes or two-dimensions as previously set and stored in the apparatus 300.

For example, FIG. 14 is a sample display of the apparatus 300 with two sets of concentric circles 998 and 999. In one implementation, the set of concentric circles 998 represents the desired three-dimensional alignment angle or orientation, such as the orientation of a pilot hole for a pedicle screw, while the set of concentric circles 999 represents the current three-dimensional orientation of the apparatus 300 showing the current orientation of the apparatus 300. As the apparatus 300 is oriented closer and closer to the desired three-dimensional alignment angle in FIGS. 15 and 16, the set of concentric circles 999 moves closer to the set of concentric circles 998 until the sets of circles are positioned over one another, or within a specified threshold, as illustrated in FIG. 16, to indicate that the apparatus 300 is aligned according to the desired three-dimensional alignment angle.

Similarly, the numerical indicators 996 and 997 in each of their respective planes are shown moving closer to zero, or within a specified threshold, as the apparatus 300 is moved closer and closer to the three-dimensional alignment angle when viewing FIGS. 14-16.

In one implementation, FIG. 15 is a sample display of the apparatus 300 in generating an indicator on the display 310 that indicates a degree of alignment between a tool aligned with a pedicle screw (or pilot hole or tool to install the pedicle screw) and the desired alignment angle, which may include an insertion sagittal angle, transverse angle, and/or coronal angle between an axis of the apparatus 300 and the sagittal plane, transverse plane, or coronal plane of the vertebra. As can be seen in FIG. 15, the indicator is in the form of a first set of concentric circles 998 and a second set of concentric circles 999. As the degree of alignment between the pedicle screw and the insertion sagittal angle, transverse angle, or coronal angle between an axis of the apparatus and the sagittal plane, transverse plane, or coronal plane of the vertebrae changes, the position of the first set of concentric circles 998 and position of the second set of concentric circles changes 999, or the position of one of the sets of the concentric circles 998 or 999 changes with respect to the other.

For example, as shown in FIG. 15, the set of concentric circles 999 is moved and positioned downward and to the right with respect to the set of concentric circles 998. This indicates that the proper alignment has not been found. By reorienting the apparatus 300, which it is noted would be directly or indirectly coupled to the pedicle screw or pilot hole location, in the appropriate direction, the set of concentric circles 999 moves closer to alignment with the set of concentric circles 998, as shown in FIG. 16. Once the proper alignment of the pedicle screw and the desired three-dimensional insertion angle between an axis of the apparatus and the vertebra has been reached, the sets of concentric circles 998 and 999 overlap one another, becoming one and the same, as shown in FIG. 16.

It can be noted that the color of the concentric circles 998 and 999 may be changed to further illustrate the degree of alignment between apparatus 300 and the desired alignment angle. For example, the misalignment indicated in FIG. 14 could be indicated by the set of concentric circles 999 being red, with the set of concentric circles 998 being blue; the better, but still not ideal, alignment indicated in FIG. 15 could be indicated by the set of concentric circles changing from red to yellow; and the ideal alignment indicated in FIG. 16 can be shown with both sets of concentric circles 998 and 999 being green.

It should be appreciated that although concentric circles have been shown, any concentric shapes can be used instead. In addition, concentric shapes need not be used, and any two individual shapes of the same size, or of a different size, may be used. Furthermore, it should be appreciated that in some instances one set of shapes may deform with respect to one another, in other instances both sets of shapes may remain at their original dimensions during operation.

In addition, in some instances, numerical indicators 996 and 997 may indicate the degree of alignment between the apparatus and a desired angle in a plane, a two-dimensional angle, such as the desired insertion sagittal angle, transverse angle, or coronal angle.

Figure 17:
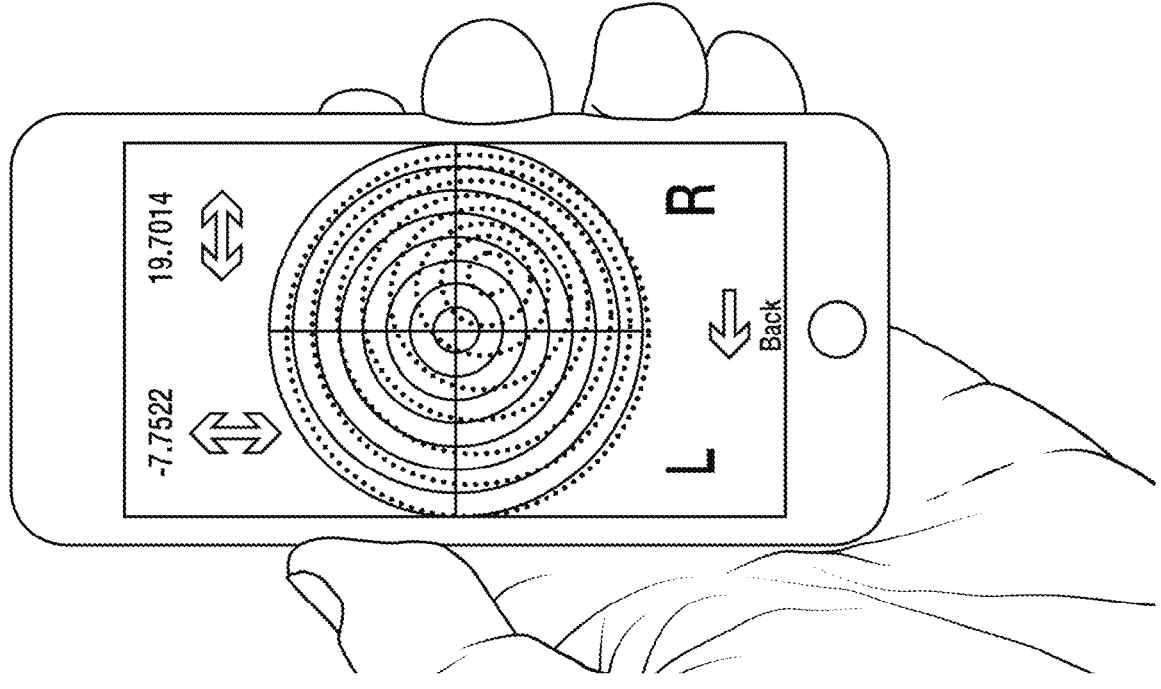
FIG. 17 illustrates the example applications shown in FIGS. 14-16 in operation on a smartphone.

FIG. 17 illustrates the example of implementing the apparatus 300 as a smartphone or smart device application, with the sets of concentric circles and numerical indicators displayed and showing relative alignment of the apparatus 300 with a desired alignment angle, such as was shown in FIGS. 14-16. The apparatus 300 includes orientation circuitry/apparatus, such as a gyroscope, to know its three-dimensional orientation.

Figure 18:
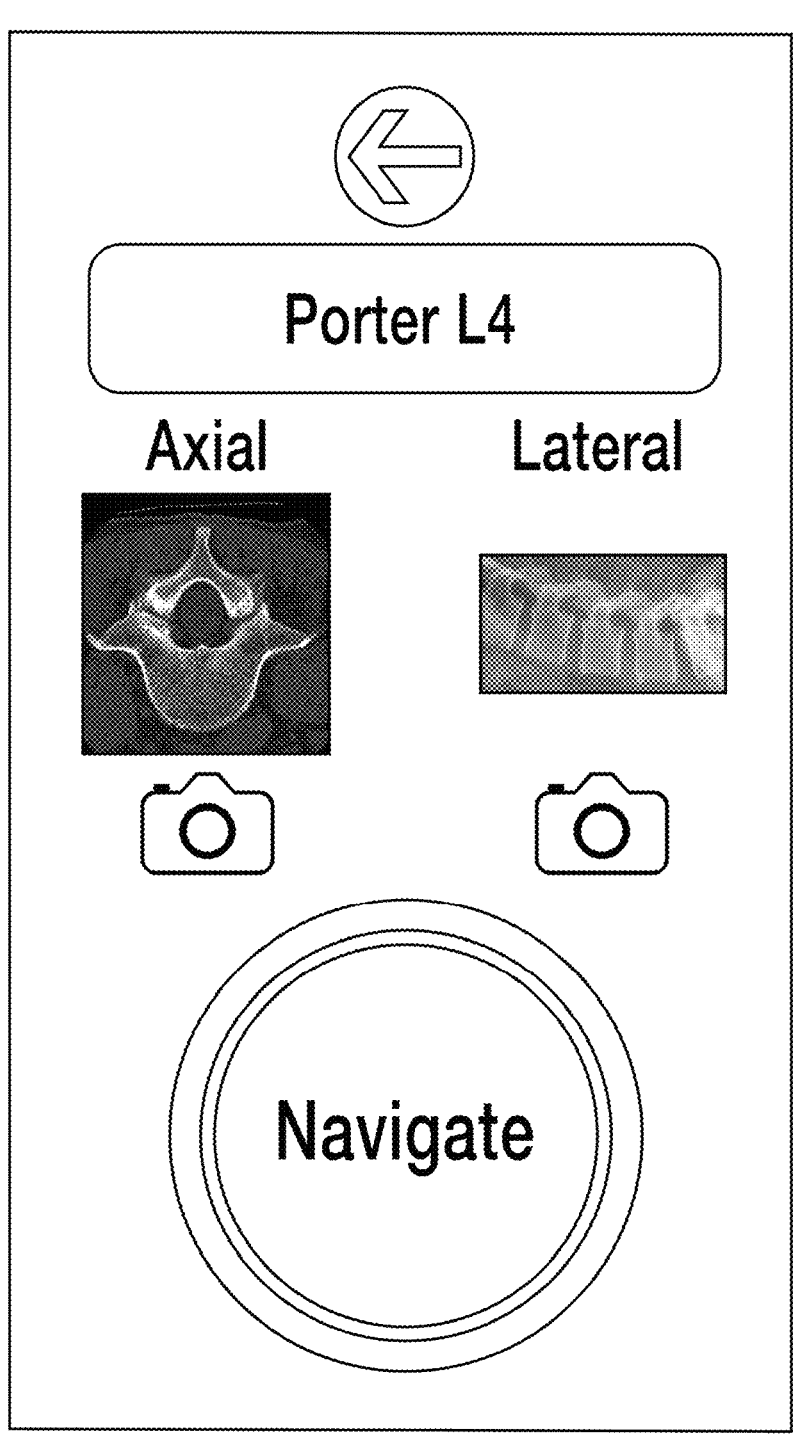
FIG. 18 illustrates a user interface of the device of FIG. 3A in operation when selecting different views of a bone.

Shown in FIG. 18 is a user interface of the apparatus 300 of FIG. 3A in operation when selecting different diagnostic image views of a vertebra that are orthogonal to one another in preparation for establishing desired alignment angles so that the three-dimensional alignment angle may be determined to install a pedicle screw. Also, a patient may be identified, as well as the specific vertebra is identified. The diagnostic images may be provided to the apparatus 300 by digital transmission, or by using a camera of the apparatus 300 to capture these two images of the vertebra that are orthogonal to one another.

Figure 25:
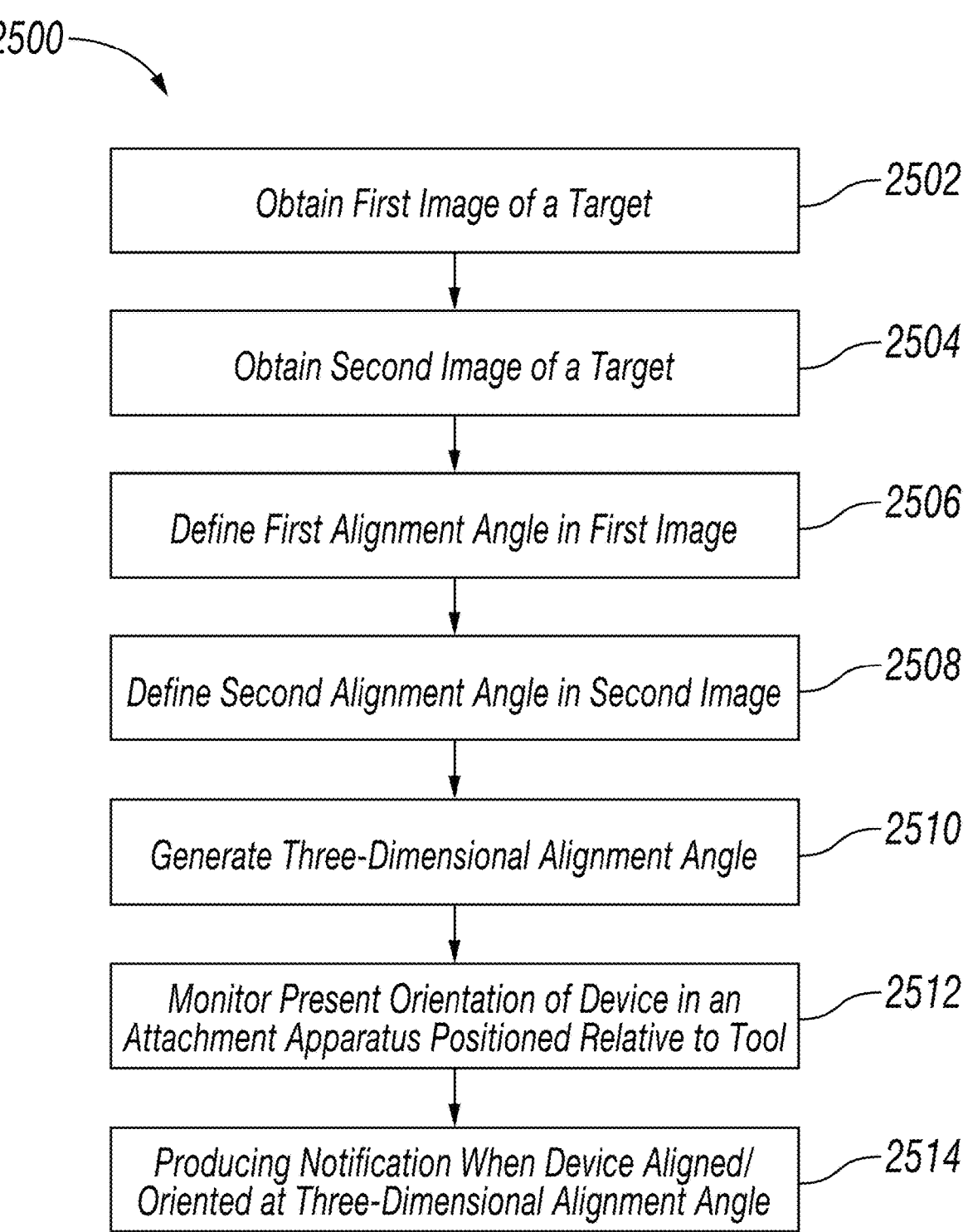
FIG. 25 is an example flowchart illustrating a method for providing a three-dimensional alignment angle to align a tool.

Referring now to FIG. 25, a flowchart 2500 is provided that illustrates an example method for providing a three-dimensional alignment angle to align a tool. At block 2502 a first image of a structure or target, such as a bone or vertebra, is obtained, and, at block 2504, a second image is obtained or acquired that is an orthogonal view (in an orthogonal plane) of the structure or target in the first image. The structure or target may be, for example, diagnostic images of a bone. The images are received by, for example, a medical alignment device, either through electronic receipt of the transmission of such images or by taking a picture of such images displayed on a monitor or display.

At block 2506, a first alignment angle of an object is simulated or superimposed on the structure or target in the first image at a first insertion point, and at a desired first alignment angle. The user may select and move the object to define the first insertion point and the first alignment angle of the object. The first alignment angle of the object may include, for example, the alignment of the axis of a pilot hole or a pedicle screw being installed in a pedicle of a vertebra in the first image. This information may be saved at or by an electronic device, such as a medical alignment device or other alignment device.

At block 2508, a second alignment angle of the object is superimposed and simulated on the structure or target in the second image, which is an orthogonal image of the structure in the first image. With the constraints of the first insertion point and the first alignment angle constraining the complete movement of the second insertion point and second alignment angle of the object, a user may, subject to these constraints, move the object to define the second insertion point and the second alignment angle of the object. This information may be saved as well.

At block 2510, a three-dimensional alignment angle is generated based on the saved information that includes the first and second insertion points and alignment angles. At block 2512, an electronic device, which may be a medical alignment device or an alignment device, that includes orientation sensors or devices, such as a three-axis gyroscope, that knows its orientation in space is used to abut or align with a tool. The tool may be, for example, a drill or gear shift pedicle probe used to make a pilot hole in a vertebra to install a pedicle screw. Because the electronic device has the three-dimensional alignment angle determined previously, the electronic device is aware when it is positioned relative to the tool such that the tool either is or is not positioned in the desired three-dimensional alignment angle. Notifications and/or feedback tools, such as the graphical concentric circles may be used to precisely position the electronic device so that the tool is positioned as desired. These feedback tools may include one or more of a visual, auditory, and tactile response.

At block 2514, when the electronic device is positioned relative to the tool such that the tool is provided at the desired three-dimensional alignment angle, a notification is produced, which may be one or more of a visual, auditory, and tactile notification.

Figure 26:
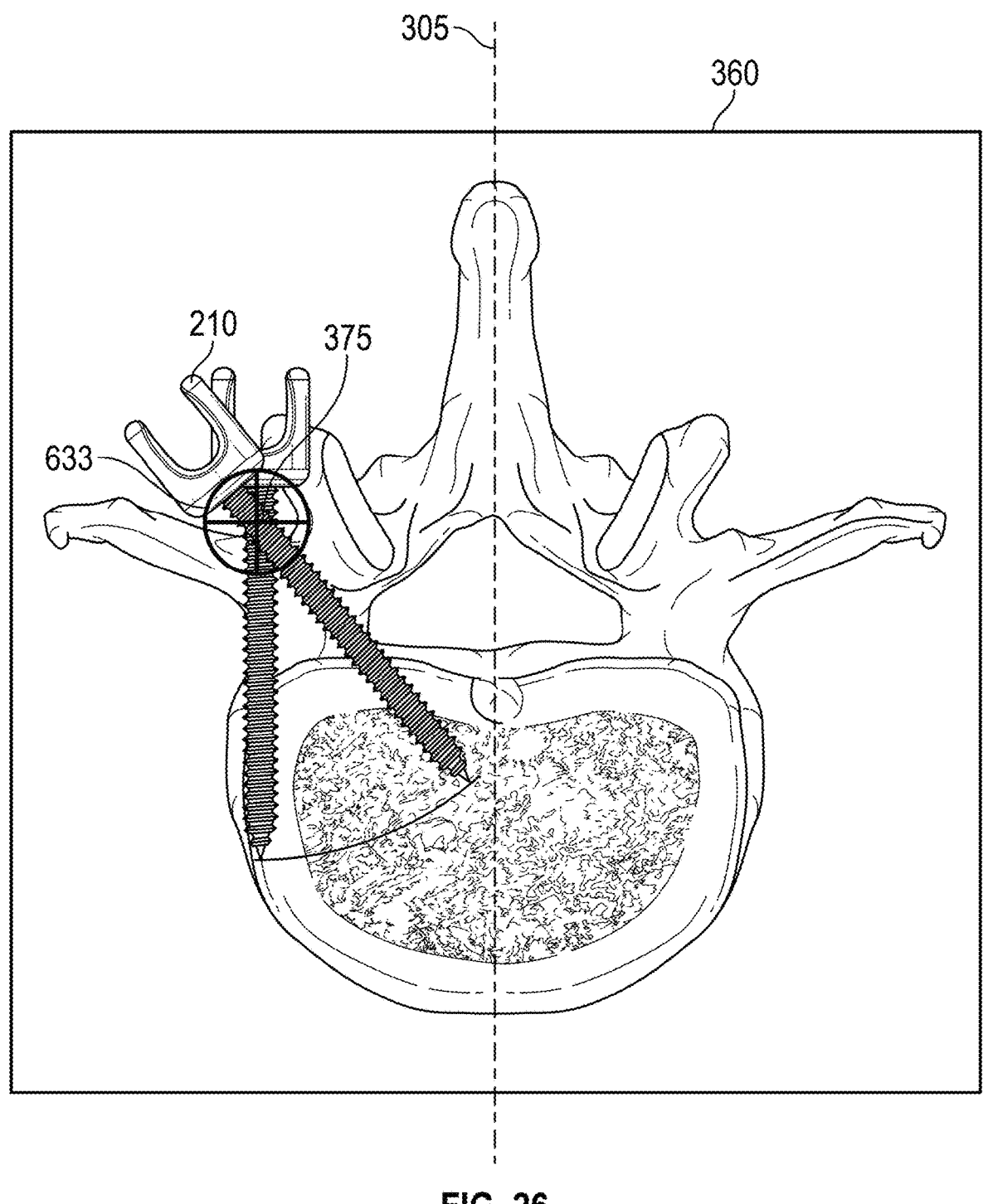
FIG. 26 illustrates a schematic diagram of a transverse view of a vertebra for defining an alignment or insertion angle for a pilot hole in the vertebra in this plane.
Figure 27:
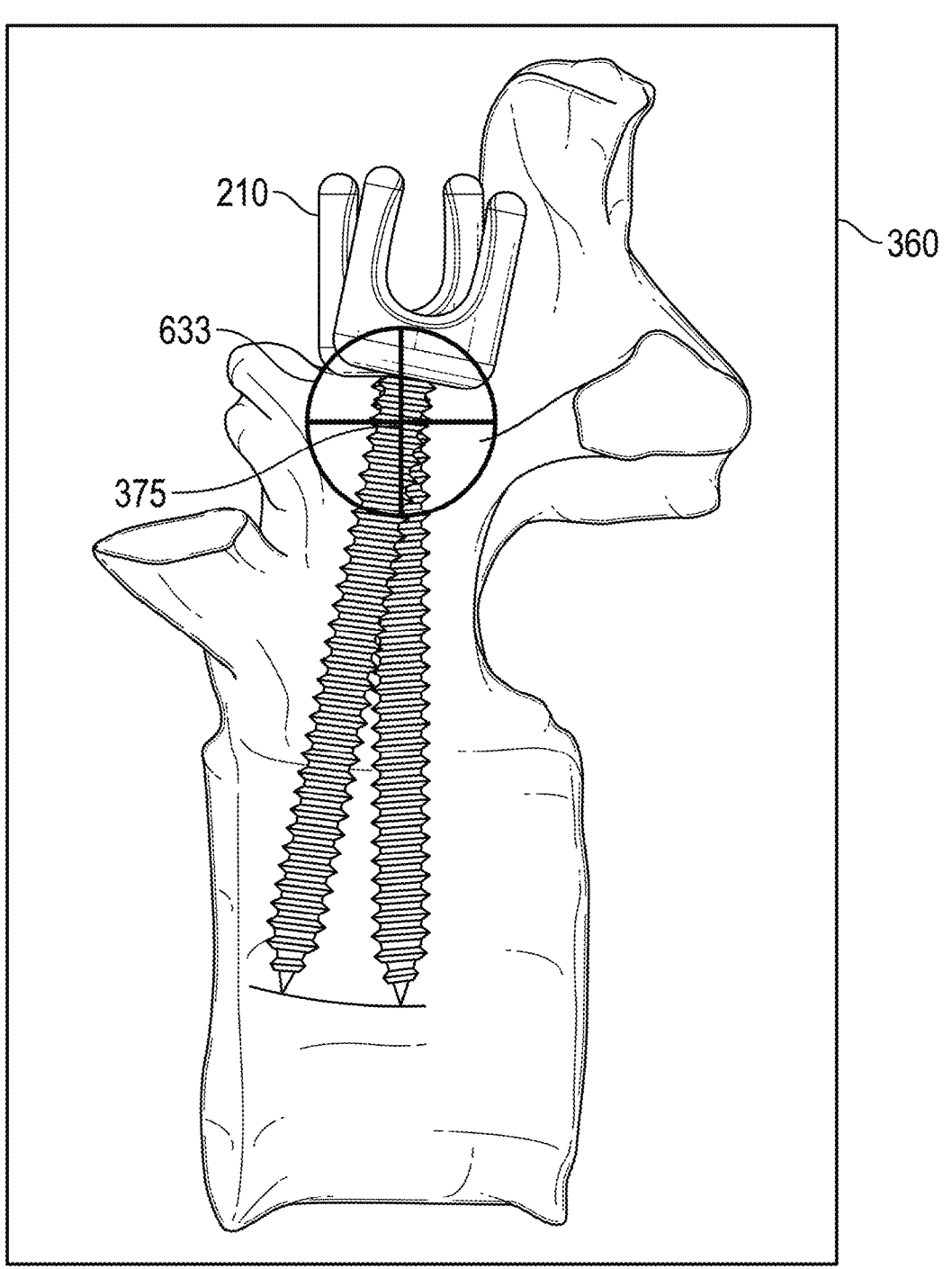
FIG. 27 illustrates a schematic diagram of a lateral view of the vertebra for defining the alignment or insertion angle for the pilot hole in the vertebra as shown in FIG. 24.

Referring now to FIGS. 26 and 27, a schematic diagram of a transverse view and a lateral view, respectively, of a vertebra defining an alignment or insertion angle for a pilot hole in the vertebra (e.g., any bone) in this plane for insertion or installation of a pedicle screw is provided. For instance, if the vertebrae in FIG. 26 was rotated 90 degrees about axis 305, the same vertebrae with the same insertion angle for the same pedicle screw can be viewed in FIG. 27. These views or diagnostic images of the vertebra may be electronically transmitted to the medical alignment device 300, or the views or images may be captured from a monitor or display of the diagnostic images using the image acquisition unit 320 of the medical alignment device 300 (sometimes referred to as apparatus 300). The display 360 shows the field of view of the view captured by the image acquisition unit 320, assuming that was how the images were acquired, and allows a user to align the axis 305 of the apparatus 300 with the desired plane. For instance, the user may view the image (e.g., a still image previously captured and communicated to the apparatus 300) with respect to the axis 305 such that the provided image is aligned with the axis 305. The views as displayed in FIGS. 26-27 are each fixed images provided along different planes. In other words, FIGS. 26/27 are not meant to illustrate a user rotating the views.

Simulating the insertion point 375 (e.g., the initial position, the insertion location, etc.) and the orientation of the simulated surgical hardware installation on the diagnostic representation of the bone includes acquiring the diagnostic representation of the bone, providing the diagnostic representation of the bone with a reference point (e.g., the crosshairs 633), and designating the insertion point of the simulated surgical hardware installation on the diagnostic representation of the bone with the reference point.

As explained above, definitions of the insertion angle of the pilot hole 220 and the initial position 375 of the pilot hole 220 (e.g., see FIG. 3B) are provided or specified by a user. For instance, the insertion location or initial position 375 of the pilot hole 220 for the installation of a pedicle screw are established by locating (or simulating) graphically the insertion location on the displayed diagnostic image, and the applicable alignment angle for the displayed plane may be defined by moving or locating (or simulating) the desired position of the alignment angle of the pilot hole/pedicle screw. Further, the user next selects the optimal pedicle screw position by selecting the navigation button 644 (e.g., FIG. 6C) to move the simulated pedicle screw to a desired location by moving the crosshairs 633 (e.g., a movable marker; see FIG. 6C) to the cortical entry point of the screw, for example, by tapping the entry point button 632 to confirm, and then tapping the trajectory button 634 and rotate the screw to its desired position 635. The crosshairs 633 specify the insertion position 375.

Simulating the orientation of the simulated surgical hardware installation further includes rotating the simulated surgical hardware installation about the insertion point on the diagnostic representation of the bone, and designating the orientation of the simulated surgical hardware installation on the diagnostic representation of the bone relative to the insertion point. Once inserted, the surgical hardware device (e.g., the pedicle screw 210) is shown in the simulated position in the vertebra through the insertion point 375, the pedicle screw 210 may be moved or rotated in this view about the insertion point 375. Rotating the simulated surgical pedicle screw 210 about the insertion point 375 includes rotating the pedicle screw 210 from left and right from the transverse view, or up and down (i.e., left and right from the lateral view). For instance, once the angle relative to the transverse plane is set as in FIG. 26, the user may view the image as in FIG. 27 (e.g., a view of the same vertebra in FIG. 26 rotated 90 degrees to the lateral view) of the patient bone by selecting a Next button to determine where the pedicle screw would reside in a third dimension. In other words, the first plane is a first fixed image to adjust the simulated pedicle screw in a first angle at which point the pedicle screw can be rotated in that direction, and the second plane is a second fixed image to adjust the simulated pedicle screw in a second angle at which point the pedicle screw can be rotated in that direction. Thus, the pedicle screw can be adjusted via a three-dimensional orientation as rotation is simulated about the entry point.

It should be understood that there is a single, rotating pedicle screw illustrated in each of FIGS. 26 and 27. For instance, separate images are shown in FIG. 26 and FIG. 27 illustrating the same pedicle screw rotated in different angles relative to the insertion point at different planes. The retake button 624 allows the user to go back to retake an image to ensure the alignment is proper.

Referring now to FIG. 28, a method 2600 for simulating a three-dimensional position of a surgical hardware device in a bone using a diagnostic representation of the bone is shown. At block 2602, the diagnostic representation of the bone (e.g., vertebrae) is displayed. The diagnostic representation may be a pictorial view of the bone, an x-ray of the bone, a radiograph of the bone, a computed tomography scan of the bone, a magnetic resonance image of the bone, or any known or available diagnostic image. At blocks 2604-2606, a movable marker, such as crosshairs 633 described above, to represent an insertion point in the bone along with the diagnostic representation of the bone is displayed and moved to the insertion point in the bone as represented by the diagnostic representation of the bone. At block 2608, the surgical hardware device to be positioned in the bone along with the diagnostic representation of the bone is displayed. At block 2610, the simulated surgical hardware device is displayed and aligned with the insertion point. At block 2612, the simulated surgical hardware device is rotated about the insertion point to a desired location within the vertebra. Rotating the simulated surgical hardware device about the insertion point includes rotating the surgical hardware device from left and right in a transverse view and left and right in a lateral view (see e.g., FIGS. 26-27). Thus, at block 2614, the orientation of the simulated surgical hardware device on the diagnostic representation of the bone is designated relative to an insertion point.

In various embodiments, the method 2600 may implement an augmented reality based electronic device to assist with the process described above (e.g., aligning the simulated surgical hardware device at a desired orientation through the insertion point of the bone by displaying visual indicia indicating the insertion point and the orientation of the simulated surgical hardware device). For instance, the visual indicia (e.g., a line representing the insertion point and the desired orientation angle) indicating the insertion point and the orientation of the simulated surgical hardware device are displayed superimposed on the bone. The desired orientation is a desired angle between the electronic device and a plane of the bone represented in the diagnostic representation of the bone.

Figure 29:
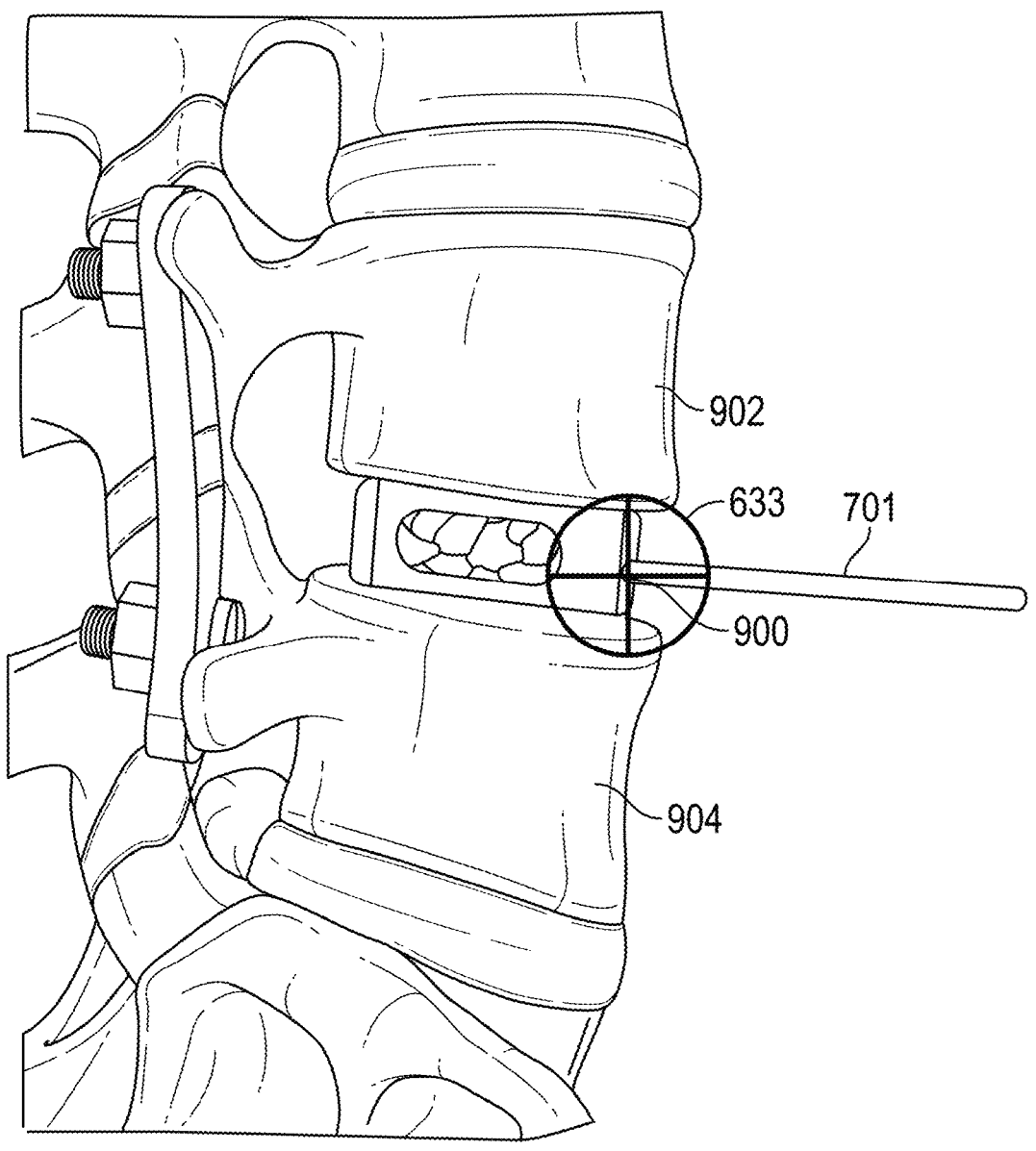
FIG. 29 illustrates a schematic diagram of a lateral view of vertebral bodies for defining the installation of a medical device between the vertebral bodies.

Referring now to FIG. 29, an alternative embodiment of a medical device installed in a body is illustrated. Particularly, an image of a medical device 900, such as an interbody cage or artificial disc, is depicted. The interbody cage can be seen disposed between two vertebral bodies 902, 904 of a spine. Although exemplary embodiments of the disclosure have been described for installing a medical device, such as a pedicle screw, into a bone, the device may be used to install, position, or align any surgical/medical hardware and assemblies into or adjacent to any part of a body. The device may be used on both human and non-human bodies (e.g., other mammals, reptiles, etc.). For instance, the device may be used to simulate positioning a medical device (e.g., an interbody cage) within a body (e.g., implanted between vertebral bodies of the spine). This operation is performed when a disc is removed and an interbody cage, or other device, is needed to be placed where the disc once was. The process of clear out the disc space can be approached from the front, back, or side of the patient. The disc space is cleaned out with a variety of instruments. Specifically, the interbody cage can be coupled to an instrument 701 (e.g., an inserter; see also FIGS. 10 and 11) to facilitate installation of the interbody cage into the disc space. For instance, the interbody cage may include a threaded opening configured to threadably couple to an end of the instrument 701. As such, when the instrument 701 is aligned as desired, as described further herein, the interbody cage will be properly aligned as desired.

Similarly, to FIGS. 26 and 27, an axial and a lateral view may be provided for the simulated alignment of the medical device (e.g., interbody cage) on a diagnostic image of at least a portion a patient's body. These views or diagnostic images of the vertebra (or other portions of a body in which a medical device may be installed or implanted) may be electronically transmitted to the medical alignment device 300, or the views or images may be captured from a monitor or display of the diagnostic images using the image acquisition unit 320 of the medical alignment device 300 (sometimes referred to as apparatus 300). The display 360 shows the field of view of the view captured by the image acquisition unit 320, assuming that was how the images were acquired, and allows a user to align the axis 305 of the apparatus 300 with the desired plane (see FIG. 3A). For instance, the user may view the image (e.g., a still image previously captured and communicated to the apparatus 300) with respect to the axis 305 such that the provided image is aligned with the axis 305.

Simulating the orientation and installation of the simulated medical device, also referred to as the surgical hardware, on a diagnostic representation of at least a portion of a body (e.g., a spine) includes acquiring the diagnostic representation, providing the diagnostic representation of the at least a portion of the body with a reference point (e.g., the crosshairs 633 representing a desired location within the body), and designating the insertion point of the simulated surgical hardware on the diagnostic representation with the reference point. In some embodiments, the insertion point need not be designated.

As explained above, definitions of the insertion angle of the pilot hole 220 and the initial position 375 (insertion or entry location) of the pilot hole 220 (e.g., see FIG. 3B) are provided or specified by a user. For instance, the insertion location or initial position 375 of the pilot hole 220 for the installation of a medical device are established by locating (or simulating) graphically the insertion location on the displayed diagnostic image, and the applicable alignment angle for the displayed plane may be defined by moving or locating (or simulating) the desired position of the alignment angle of the pilot hole for the instrument 701. For instance, the alignment angle corresponds with the inserter 701 coupled to the interbody cage to simulate the installation of the interbody cage. Further, the user can select the optimal interbody cage position by selecting the navigation button 644 (e.g., FIG. 6C) to move the simulated interbody cage to a desired location by moving the crosshairs 633 (e.g., a movable marker; see FIG. 6C) by tapping the entry point button 632 to confirm, and then tapping the trajectory button 634 and rotate the inserter 701 to its desired position 635. The crosshairs 633 specify the installation position 375. The crosshairs 633 may indicate the target location of the inserter 701, where the inserter 701 is coupled to the medical device 900, or the crosshairs 633 may be used to indicate the desired location of the medical device 900 separately.

Once the angle relative to the axial view is set (similarly to FIG. 26, the user may view the image as in FIG. 29 (e.g., a view of the same portion of the body rotated 90 degrees to the lateral view) of the body by selecting a Next button to determine where the medical device would reside in a third dimension. In other words, the first plane is a first fixed image to adjust the simulated interbody cage in a first angle at which point the interbody cage can be positioned in that direction, and the second plane is a second fixed image to adjust the simulated interbody cage in a second angle at which point the interbody cage can be rotated in that direction. Thus, the interbody cage can be adjusted via a three-dimensional orientation as rotation is simulated about the entry point with the instrument, or inserter. The rotation of the inserter 701 coupled to the interbody cage can allow adjustment of the interbody cage until one or more surfaces of the interbody cage, or one or more edges of the interbody cage, align with one or more surfaces of one or more vertebrae as desired. However, as previously stated, installing an interbody cage between two vertebral bodies is an exemplary embodiment, whereas the apparatus 300 described herein may be used to install any medical hardware at any desired location within a body.

Referring now to FIG. 30, a method 1000 for determining orientation of an instrument for positioning a medical device in a body is illustrated. At 1002, a user can simulate an orientation of a simulated medical device 900 on a diagnostic representation of at least a portion of the desired location (e.g., using the crosshairs 633) in the body. In various embodiments, this may include simulating a positioning of the medical device between vertebral bodies. However, the at least a portion of the body may be one or more portions of the body from a spine, a joint, a rib cage, a cranium, an artery, a lung, or other portion of the body to receive an implant. For instance, the medical device may be any medical hardware that includes an interbody cage, a pedicle screw, a steel rod, a stent, a bone graft, or other implant. At 1004, the user can align the instrument 701 for positioning the medical device 900 at the desired location in the body, according to the simulation of the simulated medical device 900, through an insertion point of the body by indicating when an orientation is within a threshold of the simulated orientation. In various embodiments, the method 1000 may further include capturing an image of the representation of the vertebra, generating an angle-indicative line on a display of the electronic device, wherein the angle-indicative line adjusts in response to rotation and orientation of the simulated medical device, and generating a notification when the instrument is at the correct angle for positioning the medical device. An augmented reality based electronic device may be used to assist with aligning the simulated medical device at a desired orientation through the insertion point of the body by displaying visual indicia indicating the insertion point and the orientation of the simulated surgical hardware device. For instance, the visual indicia indicating the insertion point and the orientation of the simulated medical device are displayed superimposed on the diagnostic representation of the at least a portion of the body.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:

1. An apparatus for use with an electronic device for alignment of a medical tool for positioning a surgical hardware device, the apparatus comprising:

a case to secure the electronic device such that the electronic device is secured to the case and does not move relative to the case, and wherein the case includes an opening to couple with at least a portion of the medical tool;

wherein the electronic device is secured relative to the medical tool through the coupling of the case to the at least the portion of the medical tool, the medical tool is positioned at a known angle to the case in at least one plane;

wherein the electronic device simulates a three-dimensional position of the surgical hardware device in a body using a diagnostic representation of at least a portion of the body, and wherein the electronic device secured in the case and coupled to the medical tool assists with the alignment of the medical tool using the simulated three-dimensional position of the surgical hardware device;

wherein electronic device couples to the medical tool using a holding mechanism to be received by the opening and to secure the case to the medical tool, wherein the medical tool is positioned at the known angle that is perpendicular to the case;

wherein the holding mechanism is a spring-biased plunger, wherein the spring-biased plunger is to apply a force to the medical tool against the case to secure the medical tool relative to the case; and wherein the spring-biased plunger comprises:

a main body movably coupled to the case;

a main body opening disposed on the main body such that the main body opening aligns at least partially with the opening on the case when the main body is moved from a first position to a second position, wherein the main body opening and the opening of the case are to receive the medical tool when the main body is in the second position to couple with the portion of the medical tool; and a biasing member to apply a force to the main body such that the main body is biased toward the first position.

2. The apparatus of claim 1, wherein the holding mechanism is to apply a force to the medical tool against the case to secure the medical tool relative to the case via at least one of a magnetic fit and a mechanical friction fit.

3. The apparatus of claim 1, wherein the spring-biased plunger comprises at least one slot disposed on the main body, the at least one slot corresponding with a protrusion on an inner surface of the case wherein the protrusion is received by the slot and to facilitate alignment of the main body within the case as the main body moves within the opening.

4. The apparatus of claim 1, wherein the spring-biased plunger comprises a protrusion to correspond with an elongated opening of the case to prevent the main body from vacating the case.

5. The apparatus of claim 1, wherein the electronic device is at least one of a smartphone, an iPod™, or an iPad™.

6. The apparatus of claim 1, wherein the case further includes at least one friction fit tab to eliminate movement of the electronic device within the case.

7. The apparatus of claim 1, wherein the case further includes indicators to indicate the orientation of the electronic device.

8. The apparatus of claim 1, wherein the case further includes a front opening to facilitate interaction between a user and a display screen of the electronic device.

9. The apparatus of claim 1, wherein the apparatus further comprises a sanitary drape to cover the electronic device and fit between the electronic device and the case.

10. The apparatus of claim 1, wherein the case further includes a hinged door to be opened such that the electronic device is positioned and secured within the case when the hinged door is closed, wherein the hinged door is secured to the case via a snap lock.

\* \* \* \* \*